US010093921B2

(12) United States Patent
Uppalapati et al.

(10) Patent No.: US 10,093,921 B2
(45) Date of Patent: Oct. 9, 2018

(54) SCAFFOLDED PEPTIDIC LIBRARIES AND METHODS OF MAKING AND SCREENING THE SAME

(71) Applicant: The Governing Council of the University of Toronto, Toronto (CA)

(72) Inventors: Maruti Uppalapati, Toronto (CA); Sachdev S. Sidhu, Toronto (CA); Aaron Kerman, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 367 days.

(21) Appl. No.: 14/767,891

(22) PCT Filed: Mar. 14, 2014

(86) PCT No.: PCT/IB2014/001088
§ 371 (c)(1),
(2) Date: Aug. 13, 2015

(87) PCT Pub. No.: WO2014/140882
PCT Pub. Date: Sep. 18, 2014

(65) Prior Publication Data
US 2015/0376604 A1    Dec. 31, 2015

Related U.S. Application Data

(60) Provisional application No. 61/804,982, filed on Mar. 25, 2013, provisional application No. 61/784,077, filed on Mar. 14, 2013.

(51) Int. Cl.
*C12N 15/10* (2006.01)
*C40B 40/10* (2006.01)

(52) U.S. Cl.
CPC .......... *C12N 15/1044* (2013.01); *C40B 40/10* (2013.01)

(58) Field of Classification Search
None
See application file for complete search history.

(56) References Cited

U.S. PATENT DOCUMENTS

| 5,780,221 A | 7/1998 | Schumacher et al. |
| 6,040,133 A | 3/2000 | Kent et al. |
| 6,548,279 B1 | 4/2003 | Kent et al. |
| 7,118,856 B2 | 10/2006 | Kent et al. |
| 7,408,026 B1 | 8/2008 | Kent et al. |
| 2010/0093624 A1 | 4/2010 | Low et al. |

FOREIGN PATENT DOCUMENTS

| WO | WO9201047 A1 | 1/1992 |
| WO | WO9220791 A1 | 11/1992 |
| WO | WO9306213 A1 | 4/1993 |
| WO | WO9311236 A1 | 6/1993 |
| WO | WO9319172 A1 | 9/1993 |
| WO | WO0034784 A1 | 6/2000 |
| WO | WO0074728 A1 | 12/2000 |
| WO | WO2009016043 A2 | 2/2009 |
| WO | WO2010014830 A2 | 2/2010 |
| WO | WO2010141329 A1 | 12/2010 |
| WO | WO2012003484 A2 | 1/2012 |
| WO | WO2012078313 A2 | 6/2012 |
| WO | WO2012177398 A2 | 11/2013 |
| WO | WO2014064237 A1 | 5/2014 |

OTHER PUBLICATIONS

Nord et al (Nature Biotechnology 15:772-7) (Year: 1997).*
Wiesehan et al (ChemBioChem 4:811-5) (Year: 2003).*
Ahlgren, Selection of CEA and VEGFR2 Binding Affibody® Molecules Using Phage Display, Jan. 1, 2007, XP55177554, Retrieved from the Internet: URL:http://clamator.its.uu.se/uploader/ibg.uu.se/76869_ahlgren_sara_arbete.pdf [retrieved on Mar. 18, 2015], 63 pages.
Zoller et al., Miniproteins as phage display-scaffolds for clinical applications, Molecules. Mar. 14, 2011;16(3):2467-85.
Nygren, Alternative binding proteins: affibody binding proteins developed from a small three-helix bundle scaffold, FEBS J. Jun. 2008;275(11):2668-76.
Wahlberg et al., An affibody in complex with a target protein: structure and coupled folding, Proc Natl Acad Sci U S A. Mar. 18, 2003;100(6):3185-90.
Nord et al., Ligands selected from combinatorial libraries of protein A for use in affinity capture of apolipoprotein A-1M and taq DNA polymerase, Biotechnol. Jun. 9, 2000;80(1):45-54.
Gunneriusson et al., Affinity maturation of a Taq DNA polymerase specific affibody by helix shuffling, Protein Eng. Oct. 1999;12(10):873-8.
Nord et al., A combinatorial library of an α-helical bacterial receptor domain, Protein engineering 8(6):601-8, Jul. 1995.
Grönwall et al., Selection and characterization of Affibody ligands binding to Alzheimer amyloid beta peptides, J Biotechnol. Jan. 30, 2007;128(1):162-83.
Löfblom et al., Affibody molecules: engineered proteins for therapeutic, diagnostic and biotechnological applications, FEBS Lett. Jun. 18, 2010;584(12):2670-80.
Tolmachev et al., Affibody molecules: potential for in vivo imaging of molecular targets for cancer therapy, Expert Opin Biol Ther. Apr. 2007;7(4):555-68.

(Continued)

*Primary Examiner* — Christopher M Gross
(74) *Attorney, Agent, or Firm* — Glenn J. Foulds; Bozicevic, Field & Francis LLP

(57) ABSTRACT

Scaffolded peptidic libraries and methods of screening the same for specific binding to a target protein are provided. Each library includes distinct peptidic compounds that include a scaffold domain and a distinct variable domain. A variety of libraries are provided where each library is based on an underlying peptidic scaffold having a structural motif. In some embodiments, the peptidic scaffold is a small protein having a protein-protein interaction surface. Libraries of polynucleotides that encode a variety of peptidic compounds are provided. These libraries find use in a variety of applications in which specific binding to target molecules, e.g., target proteins is desired. Also provided are methods of making the libraries and methods of screening the libraries for binding to a target.

20 Claims, 35 Drawing Sheets

(56) References Cited

OTHER PUBLICATIONS

Hosse et al., A new generation of protein display scaffolds for molecular recognition, Protein Sci. Jan. 2006; 15(1): 14-27.
Alexander et al., A minimal sequence code for switching protein structure and function, PNAS (2009), 106(50): 21149-21154.
Baker et al., Computer-based redesign of a protein folding pathway, Nature Structural Biology (2001), 8(7):602-605.
Baker et al., Crystal structures and increased stabilization of the protein G variants with switched folding pathways NuG1 and NuG2, Protein Science (2002), 11:2924-2931.
Binz et al., Engineering novel binding proteins from nonimmunoglobulin domains, Nature Biotechnology (2005), 23:1257-1268.
Byeon et al., A Protein Contortionist: Core Mutations of GB1 that Induce Dimerization and Domain Swapping, J. Mol. Biol. (2003), 333:141-152.
Cochran et al., Phage-display as a tool for quantifying protein stability determinants, Eur. J. Biochem. (2004), 271:1623-1629.
Degrado et al., Thermodynamic Genetics of the Folding of the B1 Immunoglobulin-Binding Domain From Streptococcal Protein G, Proteins: Structure, Function, and Genetics (1995), 21(1):11-21.
Dintzis et al.,A Comparison of the Immunogenicity of a Pair of Enantiomeric Proteins Proteins: Structure, Function, and Genetics (1993), 16:306-308.
Funke et al., Mirror image phage display—a method to generate D-peptide ligands for use in diagnostic or therapeutical applications, Mol. BioSyst. (2009), 5:783-786.
Ghosh et al., A Minimalist Approach toward Protein Recognition by Epitope Transfer from Functionally Evolved β-Sheet Surfaces, J. Am. Chem. Soc. (2006), 128(44):14356-14363.
Ghosh et al., Inhibition of β-Amyloid Fibrillization by Directed Evolution of a β-Sheet Presenting Miniature Protein, J. Am. Chem. Soc. (2006), 128(45):14456-14457.
Gronenborn et al., A Novel, Highly Stable Fold of the Immunoglobulin Binding Domain of *Streptococcal* Protein G,12 Science (1991), 253:657-61.
Gronenborn et al., Core mutants of the immunoglobulin binding domain of streptococcal protein G: stability and structural integrity, FEBS Letters (1996), 398:312-316.
Kim et al., Measurement of the β-sheet-forming propensities of amino acids, Nature (1994), 367:660-663.
Kim et al., Identification of D-peptide ligands through mirror-image phage display, Science (1996), 271:1854-1857.
Mayo et al., Design, structure and stability of a hyperthermophilic protein variant, Nature Structural Biology (1998), 5(6): 470-475.
Mayo et al., Probing the role of packing specificity in protein design, Proc. Natl. Acad. Sci. USA (1997), 94:10172-10177.
Rajashekhar et al., Anti-proliferative Properties of novel D-Peptide-VEGF-Antagonists: Plausible Role in Antiangiogenic and Antitumor Formation, FASEB J. (2009), vol. 23 (Meeting Abstract Supplement) 634.5.
Regan et al., A Thermodynamic Scale for the Beta-Sheet Forming Tendencies of the Amino Acids, Biochemistry (1994), 33:5510-5517.
Regan et al., Guidelines for Protein Design: The Energetics of Beta-Sheet Side Chain Interactions, Science (1995), 270:980-982.
Regan et al., Novel metal-binding proteins by design, Structural Biology (1995), 2(5):368-373.
Willbold et al., Mirror-image phage display: aiming at the mirror, ChemBioChem (2003), 4:811-815.
Wunderlich et al., In Vitro Evolution of a Hyperstable Gβ1 Variant, J. Mol. Biol. (2006), 363:545-557.

Blanco et al., Exploring the conformational properties of the sequence space between two proteins with different folds: an experimental study, J Mol Biol (1999), 285(2):741-753.
Fellouse et al., High-throughput generation of synthetic antibodies from highly functional minimalist phage-displayed libraries, J Mol Biol (2007), 373(4):924-940.
Mandal et al., Chemical synthesis and X-ray structure of a heterochiral {D-protein antagonist plus vascular endothelial growth factor} protein complex by racemic crystallography, Proc Natl Acad Sci USA (2012),109 (37):14779-14784.
Pasupuleti et al., Preservation of antimicrobial properties of complement peptide C3a, from invertebrates to humans, J Biol Chem (2007), 282(4):2520-2028.
Tonikian et al., Identifying specificity profiles for peptide recognition modules from phage-displayed peptide libraries, Nat Protoc (2007), 2(6):1368-1386.
Nord et al., Binding proteins selected from combinatorial libraries of an alpha-helical bacterial receptor domain, Nat Biotechnol (1997), 15(8):772-777.
Van Groen et al., Reduction of Alzheimer's disease amyloid plaque load in transgenic mice by D3, A D-enantiomeric peptide identified by mirror image phage displa, ChemMedChem (2008), 3(12):1848-1852.
Van Groen et al., Reduction of Alzheimer's disease amyloid plaque load in transgenic mice by D3, a D-enantiomeric peptide identified by mirror image phage displa, ChemMedChem (2008), 3(12):1848-1852.; supporting information.
Dennis et al., Potent and Selective Kunitz Domain Inhibitors of Plasma Kallikrein Designed by Phage Display, J Biol Chem (1995), 270(43):25411-25417.
Schlatter et al., Generation, characterization and structural data of chymase binding proteins based on the human Fyn kinase SH3 domain, MAbs (2012), 4(4):497-508.
Mouratou et al., Chapter 18, Ribosome Display for the Selection of Sac7d Scaffolds, Ribosome Display and Related Technologies: Methods and Protocols, Methods in Molecular Biology (2012), 805:315-331.
Speck et al., Efficient phage display of intracellularly folded proteins mediated by the TAT pathway, Protein Eng Des Sel (2011), 24(6):473-84.
Nilvebrant et al., The albumin-binding domain as a scaffold for protein engineering, Comput Struct Biotechnol J. Sep. 1, 2013;6:e201303009.
Nilvebrant et al., Engieering bispecificity into a single albumin-binding domain, PLoS One. 2011;6(10):e25791.
Ahmad et al., Novel high-affinity binders of human interferon gamma derived from albumin-binding domain of protein G, Proteins. Mar. 2012;80(3):774-89.
Alm et al., A small bispecific protein selected for orthogonal affinity purification, Biotechnol J. Jun. 2010;5(6):605-17.
Lejon et al., Crystal structure and biological implications of a bacterial albumin binding module in complex with human serum albumin, J Biol Chem. Oct. 8, 2004;279(41):42924-8.
Johansson et al., Structure, specificity, and mode of interaction for bacterial albumin-binding modules, J Biol Chem. Mar. 8, 2002;277(10):8114-20.
Oshiro et al., Imparting Albumin-Binding Affinity to a Human Protein by Mimicking the Contact Surface of a Bacterial Binding Protein, ACS Chem. Biol., 2014,9 (4), pp. 1052-1060.
Nilvebrant et al., Development and characterization of small bispecific albumin-binding domains with high affinity for ErbB3, Cell Mol Life Sci. Oct. 2013;70(20):3973-85.

* cited by examiner

SCF2-DGCR8 dimerization domain-56aa

PDB 3le4

PPTEPLPDGWIMTFHNSGVPVYLHRESRVVTWSRPYFLGTGSIRKHDPPLSSIPCL

Bolded residues randomized with (B1)HT codon

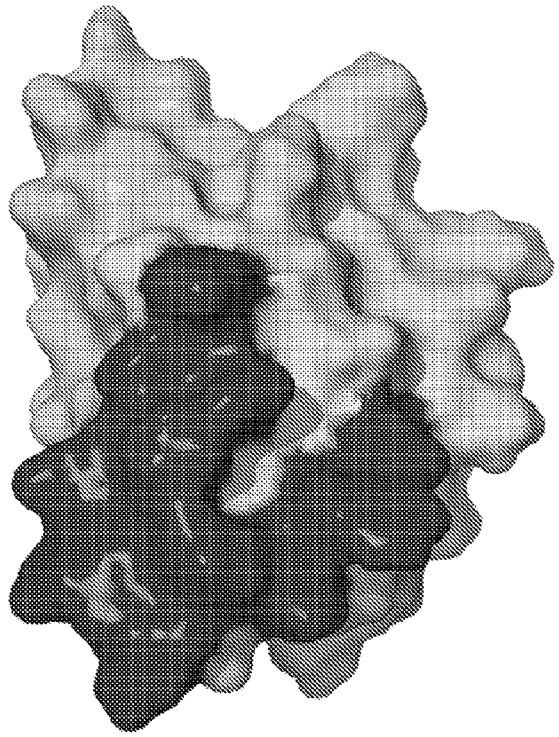
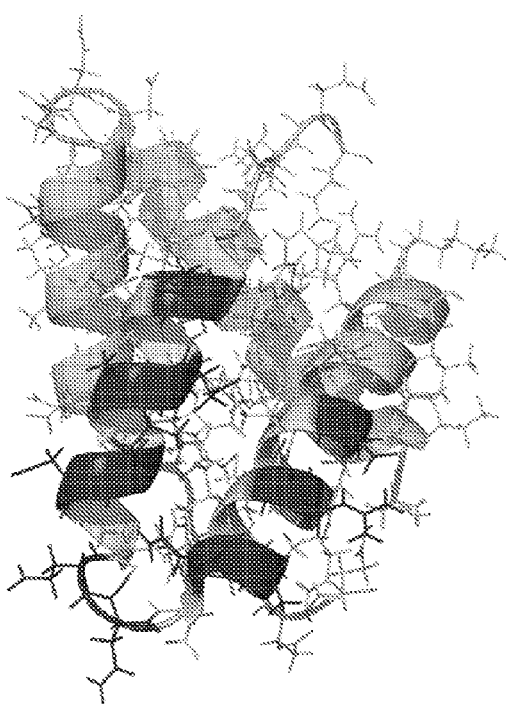
SCF3-*Get5 C-terminal domain-41aa*
PDB 2lnz
PQELTVPWDDIEALLKNNFENDQAAVRQVMERLQKGWSLAK
Bolded residues randomized with (B1)HT codon
FIG. 2

SCF4-*H-NS domain from e.coli.-46aa*

PDB 1ni8

SEALKILNNIRTLRAQARECTLETLEEMLEKLEVVVNERREEESAA

Bolded residues randomized with (B1)HT codon

Bolded residues randomized with (B1)HT codon
<u>Underlined</u> residues randomized with YWT encoding Y/F/L/H

SCF15-Symfoil 4P (designed beta-trefoil)-42aa

PDB 3ol0

PVLLKSTETGQYLRINPDGTVDGTRDRSDPHIQFQISPEGNG

Bolded residues randomized with (B1)HT codon

SCF28 - *C-terminal domain of Ku-51aa*

PDB 1jeq

YSEEELKTHISKGTLGKFTVPMLKEACRAYGLKSGLKKQELLEALTKHFQD
1         10        20        30        40        50

Bolded residues randomized with (B1)HT codon

SCF 32-GA domain of Protein G-53aa

PDB 1tf0

TIDQWLLKNAKEDAIAELKKAGITSDFYFNAINKAKTVEEVNALKNEILKAHA

Bolded residues randomized with (B1)HT codon

SCF38-*Fasciculin2-61aa*
PDB 1b41
1 10 20 30 40 50 60
TMCYSHTTTSRAILTNCGENSCYRKSRRHPPKMVLGRGCGCPPGDDNLEVKCCTSPDKCNY
Bolded residues randomized with (B1)HT codon

SCF40- *Nucleotide exchange factor C-terminal domain-60aa*

PDB 1dkg

GVEVIAETNVPLDPNVHQAIAMVESDDVAPGNVLGIMQKGYTLNGRTTIRAAMVTVAKAKA

Bolded residues randomized with (B1)HT codon

SCF44- *This protein-65aa*
PDB 1zud
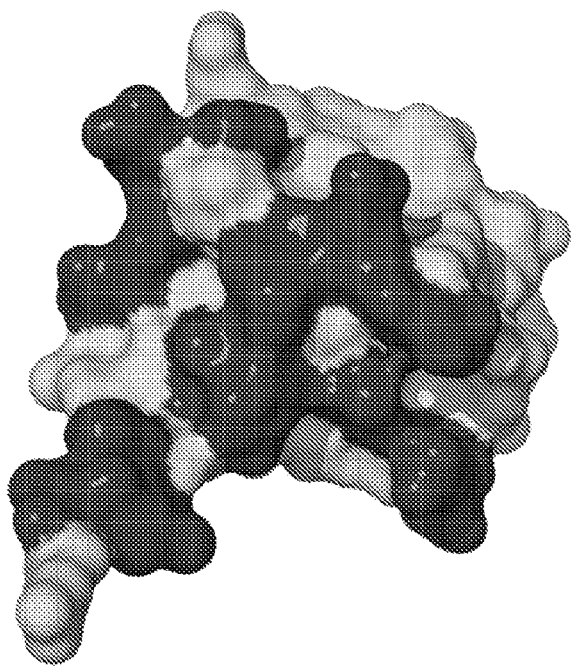
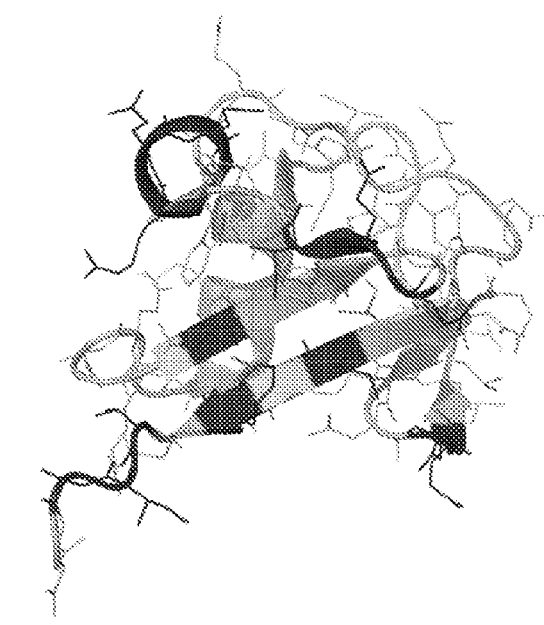
QILFNDQAMQCAAGQTVHELLEQLDQRQAGAALAINQQI VPREQWAQHIVQDGDQILLFQVIAGG
1      10       20       30       40       50       60
Bolded residues randomized with (B1)HT codon
FIG. 18

SCF47-*GYF domain of cd2bp2*-62aa
PDB 1syx
```
1         10        20        30        40        50        60
|         |         |         |         |         |         |
```
DVMWEYKWENTGDAELYGPFTSAQMQTWVSEGYFPDGVYCRKLDPPGGQFYNSKRIDFDLYT
Bolded residues randomized with (B1)HT codon

SCF56- *TNF receptor17 (BCMA) -39aa*
PDB 1oqd
SubLibrary1
1 10 20 30
CSQNE<u>Y</u>FDSLLHAC<u>I</u>PCQLRCSSNTPPLTCQRYCNASVT
Bolded residues randomized with (B1)HT codon
<u>Underlined</u> residues randomized with NTT encoding F/I/L/V

SCF56- *TNF receptor17 (BCMA) -39aa*

PDB 1oqd
SubLibrary2

```
1        10        20        30
CSQNEYFDSLLHACIPCQLRCSSNTPPLTCQRYCNASVT
```

Bolded residues randomized with (B1)HT codon

SCF63- *Fyn SH3* -61aa
PDB 1m27

VTLFVALYDYEARTEDDLSFHKGEKFQILNSSEGDWWEARSLTTGETGYIPSNYVAPVDSI

Bolded residues randomized with (B1)HT codon

SCF64- E3 ubiquitin-protein ligase UBR5-65aa
PDB 3ntw

GPLGSHRQALGERLYPRVQAMQPAFASKITGMLLELSPAQLLLLLASEDSLRARVEEAMELIVAH

Bolded residues randomized with (B1)HT codon

SCF65- *DNA repair endonuclease XPF-63aa*

PDB 2a1j

MPQDFLLKMPGVNAKNCRSLMHHVKNIAELAALSQDELTSILGNAANAKQLYDFIHTSFAEVV

Bolded residues randomized with (B1)HT codon
Underlined residue mutated with WTK codon encoding F/I/L/M
Grey residue mutated with NTT codon encoding F/I/L/V

SCF66- rad23 hom.B, xpcb domain -61aa
PDB 2f4m
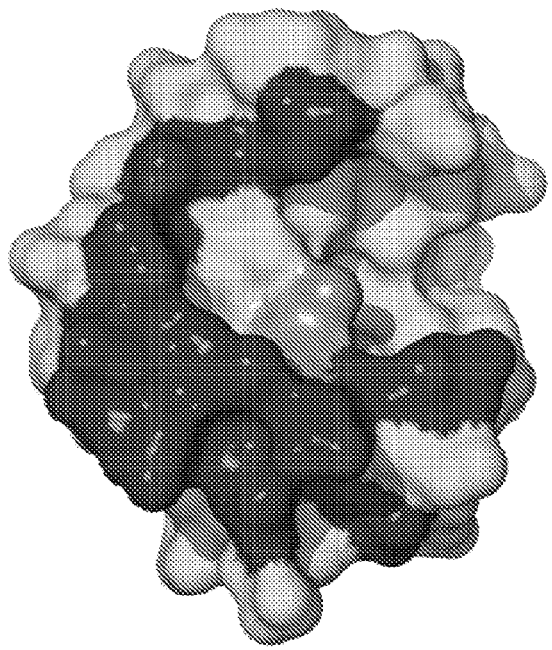
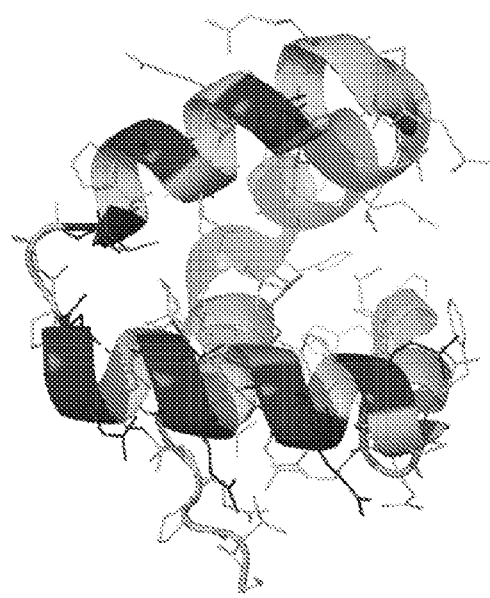
```
1         10        20        30        40        50        60
|         |         |         |         |         |         |
GHPLEFLRNQPQFQQMRQIIQQNPSLLPALLQQIGRENPQLLQQISQHQEHFIQMLNEPVG
```
Bolded residues randomized with (B1)HT codon
Underlined residue mutated with WTK codon encoding F/I/L/M
FIG. 27

SCF70- *LEM domain of Emerin-47aa*

PDB 2odg

HDNYADLSDTELTTLLRRYNIPHGPVVGSTRRLYEKKIFEYETQRRR

Bolded residues randomized with (B1)HT codon

SCF75- *GspC-68aa*
PDB 1oqd

```
GAMETRLNVVLRGIAFGARPGAVIEEGGKQQVYLQGERLDSHNAVIEEINRDHVMLRYQGKIERLSLA
|          |          |          |          |          |          |
1         10         20         30         40         50         60
```

Bolded residues randomized with (B1)HT codon

SCF95- *Protein Z -58aa*

PDB 2spz

VDNKFNKEQQNAFYEILHLPNLNEEQRNAFIQSLKDDPSQSANLLAEAKKLNDAQAPK

Bolded residues randomized with (B1)HT codon

FIG. 31

| ID# | Scaff # | SEQ ID NO. | PDB code | Name | Amino acid sequence (1-25) |
|---|---|---|---|---|---|
| SCF2 | 1 | 1 | 3le4 | DGCR8 | P P T E P L P D G W M T F H N S G V P V Y H R |
| SCF3 | 2 | 2 | 2lnz | Get5 C-terminal domain | P Q E L T V P W D D I E A L L K N N F E N D Q A A |
| SCF4 | 3 | 3 | 1ni8 | H-NS of E.Coli | S E A L K I L N N I R T L R A Q A R E C T L E T L |
| SCF7 | 4 | 4 | 1jgq | KorB -SH3 like domain | P D K L K K A I V Q V E H D E R P A R L I L N R R |
| SCF8 | 5 | 5 | 4e1p | Lsr2 dimerization domain | K V T V T L V D D E D G S G A D E T V E F G L D |
| SCF9 | 6 | 6 | 3im4 | PKA-Rlalpha (bovine) -D/D-domain | S M R E C E L Y V Q K H N I Q A L K D S V Q L |
| SCF10 | 7 | 7 | 2knv | UBA domain of p62 | G S P P E A D P R L E S L S C M L S M G E S D E |
| SCF12 | 8 | 8 | 2r05 | N-terminal domain of SpoVT | M K A T G I V R R I D D L G R V V I P K E I R T |
| SCF14 | 9 | 9 | 3n3f | Collagen XI trimerization | N L V T A F S N M D D M L Q K A T W V E G T F I |
| SCF15 | 10 | 10 | 3oi0 | symfoil-4P-beta trefoil | P V L L K S T E T G Q L L R I N P D G T V D G T R |
| SCF22 | 11 | 11 | 1z3eB00 | Orthogonal bundle-Cterm dom. RNA poly | K E K V L E M I E E L D L S V R S Y N C L K R A |
| SCF23 | 12 | 12 | 2ksoA00 | EphA2 SAM domain | T V S E W L E G I K M Q Q Y T E H F M A A G Y T A |
| SCF24 | 13 | 13 | 1r4aE00 | GRIP domain of Golgin245 | P T E F E Y L R K V L F E Y M M G R E T K T M A R |
| SCF27 | 14 | 14 | 2ftkA01 | Helix hairpin- SpoOB | I S D T A L T N E L I H L L G H S R H D W M N K L |
| SCF28 | 15 | 15 | 1jeqA05 | C-terminal domain of Ku | Y S E E S L K H I S K G L G K F Y V P M L K E |
| SCF29 | 16 | 16 | 1otrA00 | CUE domain of Cue2 protein | N D D H E S K L S L L M D M F P A I S K S K L Q V |
| SCF31 | 17 | 17 | 1ixsA00 | DNA helicase RuvA domain | E S E A A E S A V L A L A F L G F K E A Q A R A V |
| SCF32 | 18 | 18 | 1tf0B00 | GA domain of protein G | T I D Q W L L K N A K E D A I A E L K K A G I T S |
| SCF33 | 19 | 19 | 1hia | Hirustasin (kallikrein inhibitor) | T C G G E T C S A A Q V C L K G K C V C N E V H C |
| SCF35 | 20 | 20 | 1dx5 | Thrombomodulin (EGF type domain) | C N Q T A C P A D C D P N T Q A S C E C P E G Y |
| SCF36 | 21 | 21 | 2puq | Coagulation factor VIIa | Q C A S S P C Q N G G S C K D Q L Q S Y C F C L |
| SCF37 | 22 | 22 | 1mvf | PEM-1 like protein | S S V K R W G N S P A V R I P A T M Q A L N L N |
| SCF38 | 23 | 23 | 1b41 | Fasciculin-2 | T M C Y S H T T S R A I L T N C G E N S C Y R K |
| SCF39 | 24 | 24 | 2o39 | CD46 extracelluular domain | C E E P P T F E A M E L G K P K P Y Y E I G E R |
| SCF40 | 25 | 25 | 1dkg | Nucleotide exchange factor C-term. dom. | G V E V I A E T N V P D P N V H A A M V E S |
| SCF41 | 26 | 26 | 3pnw | tudor domain of TDRD3 | W K P G D E C F A L Y W E D N K F Y R A E V E A L |
| SCF42 | 27 | 27 | 2kvq | NusG transcription antitermination pro. | R P K T L F E P G E M V R V N D G P F A D I N G V |
| SCF43 | 28 | 28 | 2nz1 | CCL2 chemokine | P V T C C Y N F T N R K I S V Q R L A S Y R R I T |
| SCF44 | 29 | 29 | 1zud | ThiS protein in complex with ThiF | Q I L F N D Q A M Q C A A G Q T V H E L L E Q L D |
| SCF45 | 30 | 30 | 1tm1 | Chymotrypsin inhibitor | M K T H W P E L V G K S V E E A K K V I L Q D K P |
| SCF46 | 31 | 31 | 2abz | carboxypeptidase inhibitor | P D E S F R C N Q P D Q V C A F I C R G A A P L P |
| SCF47 | 32 | 32 | 1syx | GYF domain of cd2bp2 | D Y M W E Y K W E N T G D A E L Y G P F T S A Q M |
| SCF48 | 33 | 33 | 2ass | cdk regulatory subunit1 | Q I Y Y S D K Y D D E E F E Y R H V M L P K D I A |
| SCF49 | 34 | 34 | 2ybr | CN2 toxin | K E G Y L V D K N G G C K Y E C L K L G D N D Y C |
| SCF50 | 35 | 35 | 2i75 | CHD4 -PHD finger domain | D I H M E F C R V C K D G G E L L C C D T C P S S |
| SCF51 | 36 | 36 | 2vus | GATA type zinc finger | T T C T N C F T Q T T L W R R N P E G Q P L C N |
| SCF52 | 37 | 37 | 1ldt | Leech derived tryptase inhibitor | K K V C A C P K L K P V C G S D G R T Y A N S C |
| SCF53 | 38 | 38 | 1tbq | Rhodnin kazal inhibitor | E G G E P C P A C P H A V V C G S D G K T Y S N |
| SCF54 | 39 | 39 | 1icf | MHC ClassII p41 fragment | L T K C Q E E V S H I P A V H F G S F R P K C D E |
| SCF55 | 40 | 40 | 2zp9 | Anti-TRAP | T D D L E M A C P K C E R A G E I E G T P C P A C |
| SCF56 | 41 | 41 | 1oqd | TNF receptor17 (BCMA) | C S Q N E F D S L L H A C I P C Q L R C S S N |
| SCF57 | 42 | 42 | 3a9j | NZF zinc-finger domain | G T N G A Q W N C T A C E N H P A L I R C E Q |
| SCF58 | 43 | 43 | 1clv | AMARANTH ALPHA-AMYLASE INHIBITOR | C I P K W N R C G P K M D G V P C C E P Y T C T |
| SCF60 | 44 | 44 | 1wd1 | sac7d (nanofitins) | M V K V K F K Y K G E E K E V D T S K I K K V W R |
| SCF62 | 45 | 45 | 3l33 | APPI kunitz domain | V R E V C S E Q A E T G P C R A M I S R W Y F D V |
| SCF63 | 46 | 46 | 1m27 | Fyn SH3 (fynomers) | V T L F V A L Y D Y E A R T E D D L S F H K G E K |
| SCF64 | 47 | 47 | 3ntw | E3 ubiquitin-protein ligase UBR5 | G P L S S H R Q A L G E R L Y P R V Q A M Q P A F |
| SCF65 | 48 | 48 | 2a1j | DNA repair endonuclease XPF | M R Q D L L L M P G V N A K N C R S L M H H V K |
| SCF66 | 49 | 49 | 2f4m | rad23 hom.B, xpcb domain | G H P L E F L R N Q P Q F Q Q M R Q L I Q C N P S |
| SCF69 | 50 | 50 | 1wr1 | dsk2-uba domain | P G I S G G G G I L D P E E R Y E H L R Q L N |
| SCF70 | 51 | 51 | 2odg | LEM domain/emerin | H D N Y A D L S D T E L T T L L R R Y N I P H C P |
| SCF71 | 52 | 52 | 2g3q | Protein YBL047C UBA domain | T T P K S V A V E E L S C M G F T E E E A H N A L |
| SCF72 | 53 | 53 | 2izx | PKA docking/dimerization domain | E Q P P G E I E G Y T V E V F R Q Q P P D |
| SCF73 | 54 | 54 | 1wy3 | villin headpiece subdomain | L S D E D F K A V F G M T R S A F A N L P L W L Q |
| SCF75 | 55 | 55 | 3oss | GspC | G A M E T R L N V V L R G I A G G A R P G A W I E |
| SCF76 | 56 | 56 | 2x9a | phage IF1 attachment protein G3P | A T T D A E C L S K P A F D G L S N V W K E G D |
| SCF77 | 57 | 57 | 3u23 | cd2ap sh3 | G P L G S K K R Q C K V L E Y I P C N E D E L E |
| SCF78 | 58 | 58 | 2k2s | micronemal protein 6, EGF-like domain | M A N F V Q L S E T P A A C S S N P G P E A A G |
| SCF79 | 59 | 59 | 3qdr | colicin-A | G S K P G D S Y N T P W G K V I T N A A G Q T M |
| SCF80 | 60 | 60 | 2v3b | rubredoxin 2 | M R K W Q C V T C G F I Y D E A L G L P E E G I P |
| SCF81 | 61 | 61 | 2w2m | EGF domain of LDLR | N L Y F Q G A M G T E C D N G G C S H V C N |
| SCF82 | 62 | 62 | 3tvj | engineered protease inhibitor, SGPI scaf. | G S G E V T C P G T F L K D C N R C R C G S D |
| SCF83 | 63 | 63 | 3rea | engineered hck sh3 | M E D I I V V A L D Y V S W S P D D L S F Q K G |
| SCF89 | 64 | 64 | 1div | NTL9 (ribosomal protein L9, N-term dom) | M K V I F L K D V R G K G K K G E I K N V A D G Y |
| SCF90 | 65 | 65 | 2brz | Brazzein | E D K C K K V Y E N Y P V S K C Q L A N Q C N Y D |
| SCF91 | 66 | 66 | 1h59 | IGFBP | S A L A E G Q S C G V L T E R C A Q G L P C P R |
| SCF92 | 67 | 67 | 1ror | ovomucoid | V D C S E Y P K P A C T L E Y R P L C G S D N K T |
| SCF93 | 68 | 68 | 3c8p | Chromobox protein homolog 5 | E E Y V V E K V L D R R V V K G Q V E Y L L K W K |
| SCF94 | 69 | 69 | 3fdt | viscotoxin | K S C C P S T T G R N I Y N T C R L G G S S R E |
| SCF95 | 70 | 70 | 2spz | Protein Z | V D N K F N K E Q Q N A F Y E I L H L P N L N E E |

| ID # | Scaff# | PDB code | Name | Positions of mutations in numbered sequence | | | | | | | | | | | | | | | | |
|---|---|---|---|---|---|---|---|---|---|---|---|---|---|---|---|---|---|---|---|---|---|
| SCF2 | 1 | 3le4 | DGCR8 | 11 | 13 | 14 | 23 | 25 | 26 | 28 | 40 | 42 | 43 | 44 | 45 | | | | | |
| SCF3 | 2 | 2inz | Get5 C-terminal domain | 9 | 12 | 13 | 16 | 17 | 20 | 21 | 23 | 24 | 27 | 31 | | | | | | |
| SCF4 | 3 | 1ni8 | H-NS of E.Coli | 22 | 23 | 26 | 27 | 30 | 33 | 37 | 40 | 41 | 43 | 44 | | | | | | |
| SCF7 | 4 | 1igq | KorB -SH3 like domain | 13 | 14 | 15 | 16 | 31 | 36 | 38 | 39 | 41 | 43 | 44 | 46 | 48 | 49 | | | |
| SCF8 | 5 | 4e1p | Lsr2 dimerization domain | 10 | 11 | 13 | 36 | 37 | 39 | 40 | 43 | 44 | 46 | 47 | 50 | | | | | |
| SCF15 | 10 | 3oi0 | symfoil-4P-beta trefoil | 5 | 8 | 10 | 12 | 25 | 26 | 27 | 35 | 37 | 38 | 39 | 40 | | | | | |
| SCF23 | 12 | 2ksoA00 | EphA2 SAM domain | 7 | 8 | 10 | 12 | 13 | 43 | 44 | 45 | 46 | 47 | 49 | 50 | 53 | | | | |
| SCF24-1 | 13 | 1r4aE00 | GRIP domain of Golgin245 | 5 | 6 | 9 | 13 | 18 | 19 | 22 | 25 | 26 | | | | | | | | |
| SCF24-2 | 13 | 1r4aE00 | GRIP domain of Golgin245 | 2 | 3 | 5 | 6 | 9 | 22 | 25 | 26 | 29 | 30 | | | | | | | |
| SCF27 | 14 | 2ftkA01 | Helix hairpin- SpoOB | 19 | 22 | 23 | 26 | 27 | 29 | 30 | 41 | 45 | 48 | 52 | 55 | | | | | |
| SCF28 | 15 | 1jeqA05 | C-terminal domain of Ku | 1 | 2 | 4 | 5 | 8 | 9 | 12 | 13 | 14 | 17 | 19 | 22 | | | | | |
| SCF29 | 16 | 1otrA00 | CUE domain of Cue2 protein | 6 | 10 | 13 | 14 | 33 | 34 | 35 | 39 | 42 | 43 | 45 | | | | | | |
| SCF32 | 18 | 1tf0B00 | GA domain of protein G | 25 | 27 | 28 | 31 | 34 | 36 | 37 | 39 | 40 | 43 | 44 | 47 | | | | | |
| SCF37 | 22 | 1mvf | PEM-1 like protein | 5 | 16 | 17 | 20 | 21 | 23 | 25 | 26 | 33 | 34 | 35 | 36 | | | | | |
| SCF38 | 23 | 1b41 | Fasciculin-2 | 7 | 8 | 9 | 10 | 11 | 27 | 29 | 30 | 31 | 32 | 33 | 35 | 46 | 47 | 48 | | |
| SCF40 | 25 | 1dkg | Nucleotide exchange factor C-terminal dom. | 14 | 15 | 18 | 20 | 21 | 22 | 23 | 35 | 37 | 38 | 51 | 52 | 54 | | | | |
| SCF42 | 27 | 2kvq | transcription antitermination protein NusG | 16 | 17 | 18 | 19 | 22 | 42 | 43 | 45 | 47 | 55 | | | | | | | |
| SCF44 | 29 | 1zud | ThiS protein in complex with ThiF | 6 | 7 | 11 | 32 | 37 | 38 | 39 | 42 | 43 | 44 | 57 | 59 | 61 | 62 | 63 | | |
| SCF47 | 32 | 1syx | GYF domain of cd2bp2 | 42 | 45 | 46 | 47 | 48 | 49 | 51 | 55 | 57 | 59 | 60 | 61 | | | | | |
| SCF53 | 38 | 1tbq | Rhodnin kazal inhibitor | 9 | 10 | 12 | 13 | 21 | 22 | 26 | 28 | 32 | 46 | 49 | 51 | | | | | |
| SCF55 | 40 | 2zp9 | Anti-TRAP | 2 | 3 | 6 | 9 | 10 | 24 | 26 | 31 | 33 | 34 | 35 | 37 | 38 | 41 | | | |
| SCF56-1 | 41 | 1oqd | TNF receptor17 (BCMA) | 6 | 9 | 10 | 11 | 12 | 15 | 19 | 20 | 22 | 23 | 24 | 25 | 28 | | | | |
| SCF56-2 | 41 | 1oqd | TNF receptor17 (BCMA) | 9 | 10 | 11 | 12 | 19 | 22 | 23 | 25 | 28 | | | | | | | | |
| SCF63 | 46 | 1m27 | Fyn SH3 (fynomers) | 13 | 14 | 15 | 16 | 30 | 31 | 32 | 33 | 34 | 35 | 36 | 38 | 49 | | | | |
| SCF64 | 47 | 3ntw | E3 ubiquitin-protein ligase UBR5 | 4 | 7 | 8 | 12 | 15 | 27 | 28 | 31 | 32 | 35 | 36 | 54 | 57 | 61 | | | |
| SCF65 | 48 | 2a1j | DNA repair endonuclease XPF | 2 | 4 | 5 | 8 | 9 | 26 | 27 | 28 | 31 | 32 | 54 | 55 | 56 | 57 | 58 | 59 | 60 |
| SCF66 | 49 | 2i4m | rad23 hom.B, xpcb domain | 12 | 14 | 15 | 16 | 18 | 19 | 22 | 23 | 26 | 29 | 33 | | | | | | |
| SCF70 | 51 | 2odg | LEM domain/emerin | 22 | 23 | 24 | 25 | 27 | 29 | 30 | 33 | 34 | 36 | 37 | | | | | | |
| SCF75 | 54 | 3oss | GspC | 12 | 13 | 15 | 16 | 19 | 23 | 30 | 32 | 34 | 51 | 52 | 67 | 68 | | | | |
| SCF95 | 70 | 2spz | Protein Z | 10 | 11 | 13 | 14 | 17 | 18 | 23 | 24 | 25 | 27 | 28 | 31 | 32 | | | | | ial Application No. 61/784,077, filed Mar. 14, 2013, and U.S. Provisional Application No. 61/804,982, filed Mar. 25, 2013, which applications are incorporated herein by reference.

SCAFFOLDED PEPTIDIC LIBRARIES AND METHODS OF MAKING AND SCREENING THE SAME

CROSS REFERENCE TO RELATED APPLICATION

Pursuant to 35 U.S.C. § 119(e), this application claims priority to U.S. Provisional Application No. 61/784,077, filed Mar. 14, 2013, and U.S. Provisional Application No. 61/804,982, filed Mar. 25, 2013, which applications are incorporated herein by reference.

INTRODUCTION

Essentially all biological processes depend on molecular recognition mediated by proteins. The ability to manipulate the interactions of such proteins is of interest for both basic biological research and for the development of therapeutics and diagnostics.

Libraries of polypeptides can be prepared, e.g., by manipulating the immune system or via chemical synthesis, from which specificity of binding to target molecules can be selected. Molecular diversity from which specificity can be selected is large for polypeptides having numerous possible sequence combinations of amino acids. In addition, proteins can form large binding surfaces with multiple contacts to a target molecule that leads to highly specific and high affinity binding events. For example, antibodies are a class of protein that has yielded highly specific and tight binding ligands for various target antigens.

Because of the variety of target molecules of interest, and because of the binding properties of proteins, peptidic libraries and methods of screening the same to identify molecules with useful functions is of interest.

SUMMARY

Scaffolded peptidic libraries and methods of screening the same for specific binding to a target protein are provided. Each library includes distinct peptidic compounds that include an underlying scaffold domain and a distinct variable domain. A variety of libraries are provided where each library is based on a peptidic scaffold having a structural motif. In some embodiments, the peptidic scaffold is a small protein having a surface suitable for protein-protein interactions. Libraries of polynucleotides that encode a variety of peptidic compounds are provided. These libraries find use in a variety of applications in which specific binding to target molecules, e.g., target proteins is desired. Also provided are methods of making the libraries and methods of screening the libraries for binding to a target.

BRIEF DESCRIPTION OF THE DRAWINGS

FIGS. 1-31 illustrate the structural motifs and sequences of some scaffold domains of interest including the locations of mutations of interest. For each scaffold domain two alternate structural representations are depicted, where the darkened areas of the structures depict the variable domain of one embodiment of a library based on the scaffold, which corresponds to the locations of the mutations indicated in the sequences below. Polypeptide sequences are shown that may be utilized in preparing one embodiment of a peptidic library based on the scaffolds, where bolded, highlighted and grey residues denote positions of mutations of interest that may be randomized (e.g., with a B1(HT), WTK or NTT codon in a phage display library).

FIG. 1: SCF2, DGCR8 (DiGeorge syndrome critical region 8) dimerization domain (SEQ ID NO:1).

FIG. 2: SCF3, Get5 C-terminal domain (SEQ ID NO:2).

FIG. 3: SCF4, H-NS domain from *E. coli* (SEQ ID NO:3).

FIG. 4: SCF7, KorB c-terminal dimerization domain (SEQ ID NO:4).

FIG. 5: SCF8, Lsr2 dimerization domain (SEQ ID NO:5). The first 6 residues may be truncated.

FIG. 6: SCF15, Symfoil 4P trimer (designed beta-trefoil) (SEQ ID NO:10).

FIG. 7: SCF23, EphA2 SAM domain (SEQ ID NO:12).

FIG. 8: SCF24-1, GRIP domain of Golgin245, sub-library 1 (SEQ ID NO:13).

FIG. 9: SCF24-2, GRIP domain of Golgin245, sub-library 2 (SEQ ID NO:13).

FIG. 10: SCF27, SpoOB-Helix hairpin domain (SEQ ID NO:14).

FIG. 11: SCF28, C-terminal domain of Ku (SEQ ID NO:15).

FIG. 12: SCF29, CUE domain of Cue2 protein (SEQ ID NO:16).

FIG. 13: SCF32, GA domain of protein G (SEQ ID NO:18).

FIG. 14: SCF37, PEM-1 like protein (SEQ ID NO:22).

FIG. 15: SCF38, Fasciculin-2 (SEQ ID NO:23).

FIG. 16: SCF40, Nucleotide exchange factor C-terminal domain (SEQ ID NO:25).

FIG. 17: SCF42, Transcription antitermination protein NusG (SEQ ID NO:27).

FIG. 18: SCF44, ThiS protein in complex with ThiF (SEQ ID NO:29).

FIG. 19: SCF47, GYF domain of CD2bp2 (SEQ ID NO:32).

FIG. 20: SCF53, Rhodnin Kazal inhibitor (SEQ ID NO:38).

FIG. 21: SCF55, Anti-TRAP (SEQ ID NO:40).

FIG. 22: SCF56-1, TNF Receptor 17 (BCMA), sub-library 1 (SEQ ID NO:41).

FIG. 23: SCF56-2, TNF Receptor 17 (BCMA), sub-library 2 (SEQ ID NO:41).

FIG. 24: SCF63, Fyn SH3 domain (Fynomers) (SEQ ID NO:46).

FIG. 25: SCF64, E3 ubiquitin-protein ligase UBR5 (SEQ ID NO:47).

FIG. 26: SCF65, DNA repair endonuclease XPF (SEQ ID NO:48).

FIG. 27: SCF66, Rad23 homologue B, xpcb domain (SEQ ID NO:49).

FIG. 28: SCF70, LEM domain of emerin (SEQ ID NO:51).

FIG. 29: SCF75, GspC (SEQ ID NO:55).

FIG. 30: SCF95, Protein Z (SEQ ID NO:70).

FIGS. 31 and 32 shows a table of all scaffolds 1-70 of interest and show one embodiment each of a library based on these scaffold. For each scaffolded library, positions of interest for mutations are depicted by a black square around the residue. FIG. 31 shows amino acids 1-25 of scaffolds 1-70 and FIG. 32 shows amino acids 26 onwards.

FIGS. 33 and 34 shows a table including a subset of the scaffolds (i.e., those depicted in FIGS. 1-30). For each scaffolded library, positions of interest for mutations are depicted by either a black (e.g., may be randomized with a (B1)HT codon) or a grey square (e.g., may be randomized with a WTK or NTT codon) around the particular residue.

FIG. 31 shows amino acids 1-25 of scaffolds 1-70 and FIG. 32 shows amino acids 26 onwards.

FIG. 35 shows a table including a subset of the scaffolds (i.e., those depicted in FIGS. 1-30), where positions of mutations of interest are listed.

DEFINITIONS

Figure 1:
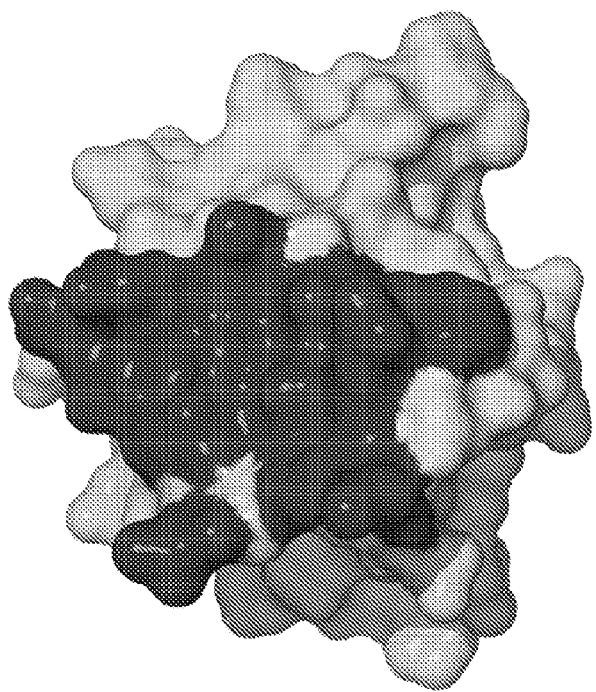

As used herein, the term "peptidic" refers to a moiety that is composed of amino acid residues. The term "peptidic" includes compounds or libraries of naturally occurring amino acids and compounds or libraries in which the conventional backbone has been replaced with non-naturally occurring (e.g., synthetic) backbones, and peptides in which one or more naturally occurring amino acids have been replaced with one or more non-naturally occurring (e.g., synthetic amino acids), or a D-amino acid. As used herein, the term "synthetic amino acid" refers to a non-naturally occurring amino acid. Any of the depictions of sequences found herein (e.g., using one-letter or three-letter codes) may represent a L-amino acid or a D-amino acid version of the sequence (e.g., the capital and small letter code conventions used in the art to refer to L- and D-amino acid residues do not strictly apply herein, for simplicity). In some cases, the subject peptidic libraries and peptidic compounds are L-peptidic. It is understood that, in other cases, the subject peptidic libraries and peptidic compounds are D-peptidic, and as such have structural motifs that are mirror image structures of a native underlying L-peptidic scaffold structural motif.

As used herein, the terms "polypeptide" and "protein" are used interchangeably. The term "polypeptide" also includes post translational modified polypeptides or proteins. The term "polypeptide" includes polypeptides in which one or more residue units of the naturally occurring backbone has been replaced with one or more residues having a non-naturally occurring (i.e., synthetic) backbones. A variety of peptidomimetic backbones and sidechains may be utilized in the subject polypeptides. In some instances, a polypeptide is a peptide. In some instances, polypeptides may be of any length, e.g., 2 or more amino acids, 4 or more amino acids, 10 or more amino acids, 20 or more amino acids, 25 or more amino acids, 30 or more amino acids, 35 or more amino acids, 40 or more amino acids, 45 or more amino acids, 50 or more amino acids, 55 or more amino acids, 60 or more amino acids, 100 or more amino acids, 300 or more amino acids, 500 or more or 1000 or more amino acids.

As used herein, the term "discontinuous sequence of residues" refers to a sequence of residues that is not continuous with respect to the primary sequence of a peptidic compound. A peptidic compound may fold to form a secondary or tertiary structure, where the amino acids of a discontinuous sequence of residues are adjacent to each other in space, i.e., contiguous. As used herein, the term "continuous sequence of residues" refers to a sequence of residues that is continuous in terms of the primary sequence of a peptidic compound.

As used herein, the term "linking sequence" refers to a continuous sequence of amino acid residues, or analogs thereof, that connect two peptidic motifs.

As used herein, the term "phage display" refers to a technique by which variant peptidic compounds are displayed as fusion proteins to a coat protein on the surface of phage, e.g. filamentous phage particles. The term "phagemid" refers to a plasmid vector having a bacterial origin of replication, e.g., ColE1, and a copy of an intergenic region of a bacteriophage. The phagemid may be based on any known bacteriophage, including filamentous bacteriophage. In some instances, the plasmid will also contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids that contain a phage coat protein gene or fragment thereof linked to a heterologous polypeptide gene as a gene fusion such that the heterologous polypeptide is displayed on the surface of the phage particle.

As used herein, the term "phage vector" refers to a double stranded replicative form of a bacteriophage that contains a heterologous gene and is capable of replication. The phage vector has a phage origin of replication allowing phage replication and phage particle formation. In some cases, the phage is a filamentous bacteriophage, such as an M13, f1, fd, Pf3 phage or a derivative thereof, a lambdoid phage, such as lambda, 21, phi80, phi81, 82, 424, 434, etc., or a derivative thereof, a Baculovirus or a derivative thereof, a T4 phage or a derivative thereof, a T7 phage virus or a derivative thereof.

As used herein, the term "stable" refers to a compound that is able to maintain a folded state under physiological conditions at a certain temperature (e.g., 25° C. or 37° C.), such that it retains at least one of its normal functional activities, for example binding to a target protein. The stability of the compound can be determined using standard methods. For example, the "thermostability" of a compound can be determined by measuring the thermal melt ("Tm") temperature. The Tm is the temperature in degrees Celsius of the temperature of midtransition between unfolded or denatured and structurally stable. In general terms, the higher the Tm, the more stable the compound.

The compounds of the subject libraries may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids and polypeptides. The present invention is meant to include all such possible isomers, as well as, their racemic and optically pure forms. When the compounds described herein contain olefinic double bonds or other centers of geometric asymmetry, and unless specified otherwise, it is intended that the compounds include both E and Z geometric isomers. Likewise, all tautomeric forms are also intended to be included.

DETAILED DESCRIPTION

Figure 3:
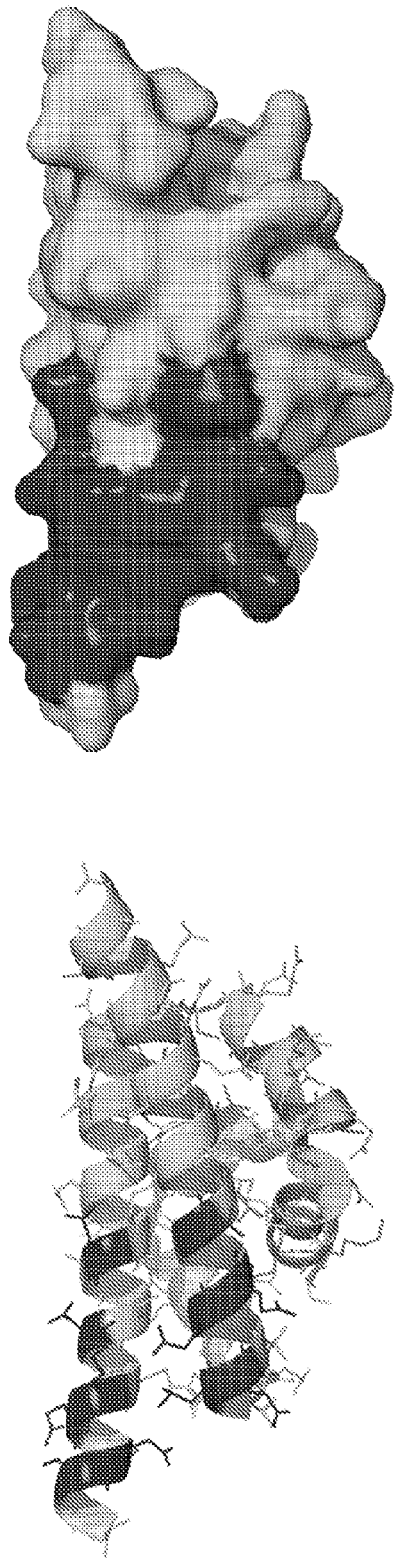
Figure 4:
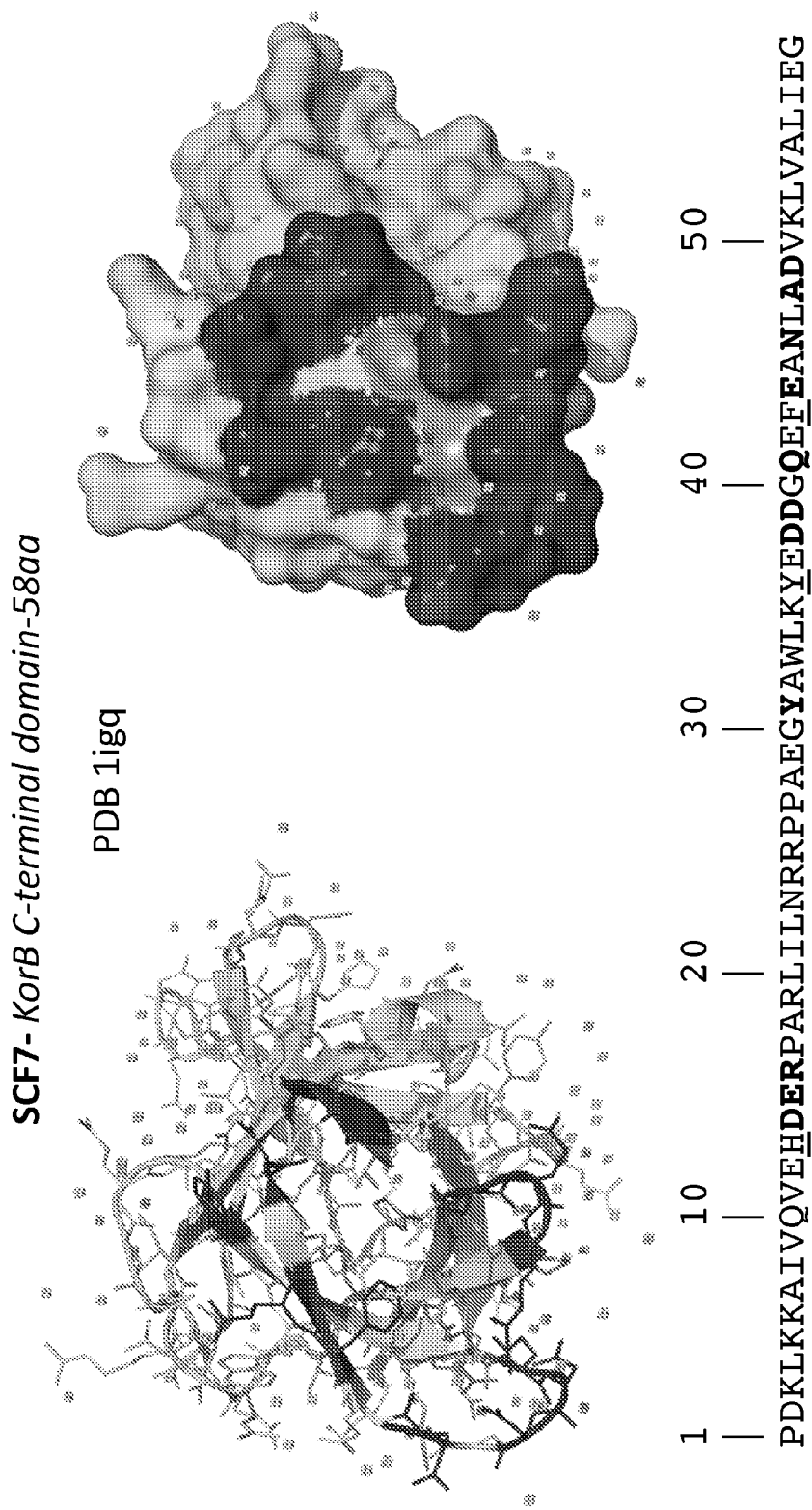
Figure 5:
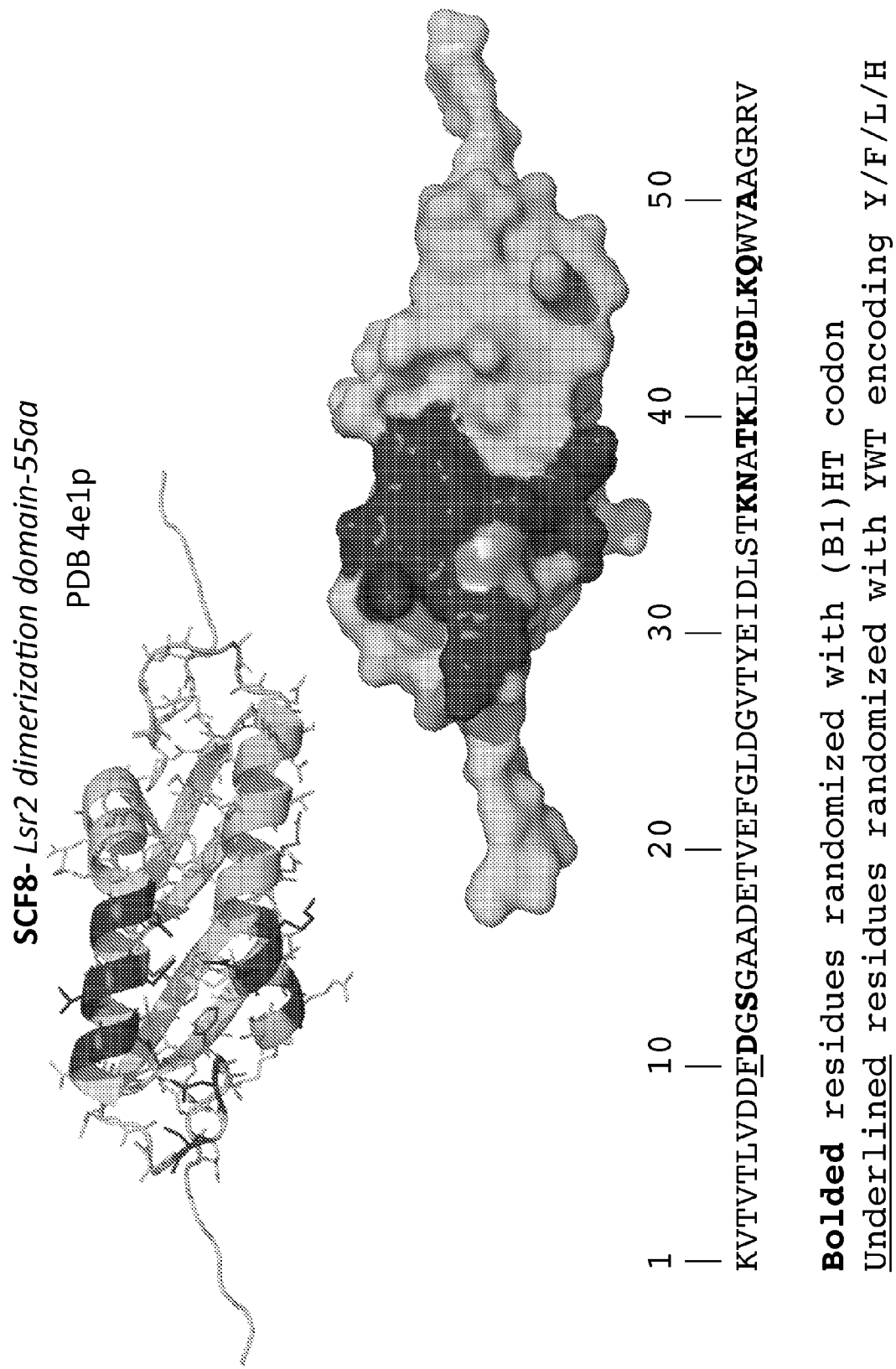
Figure 6:
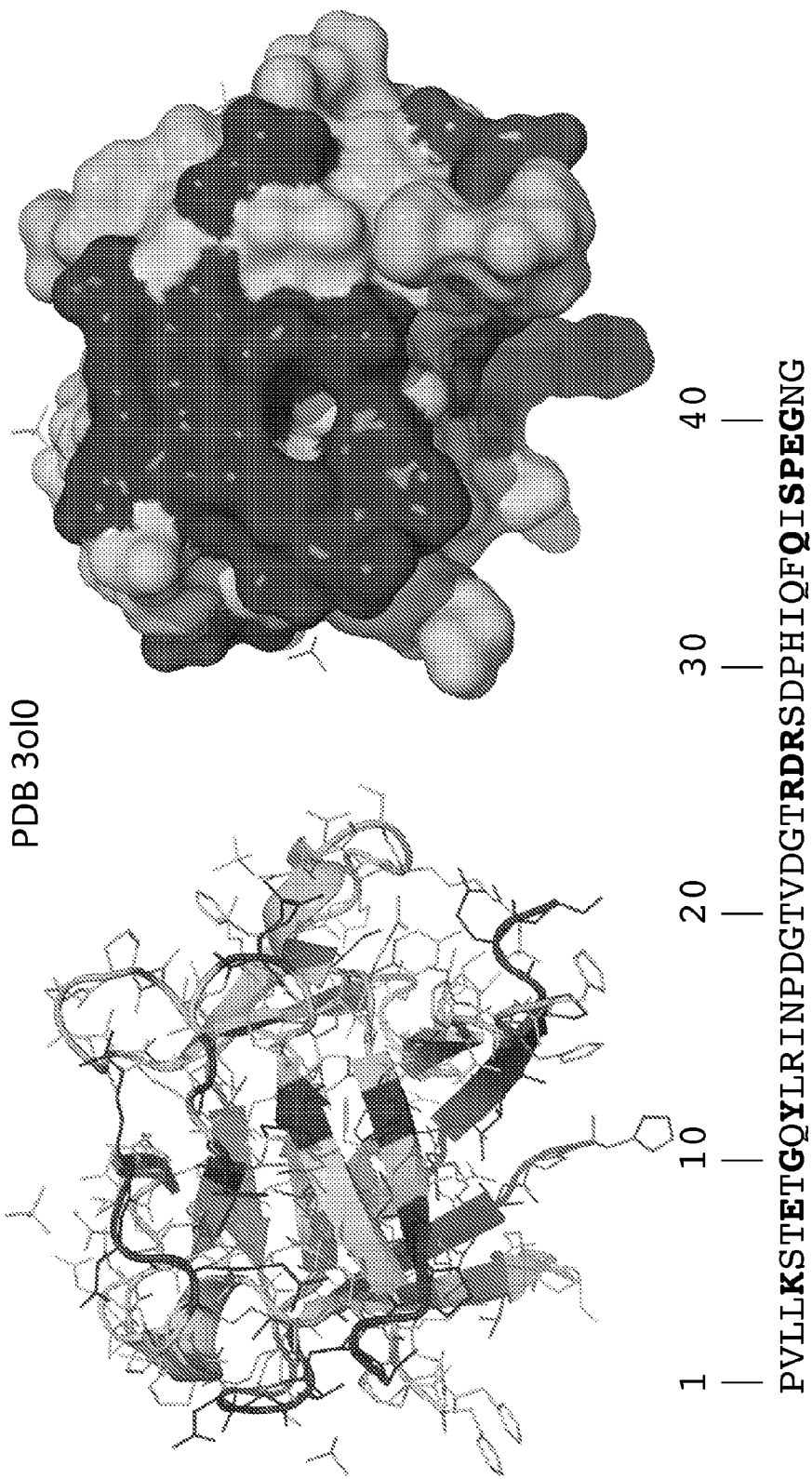
Figure 7:
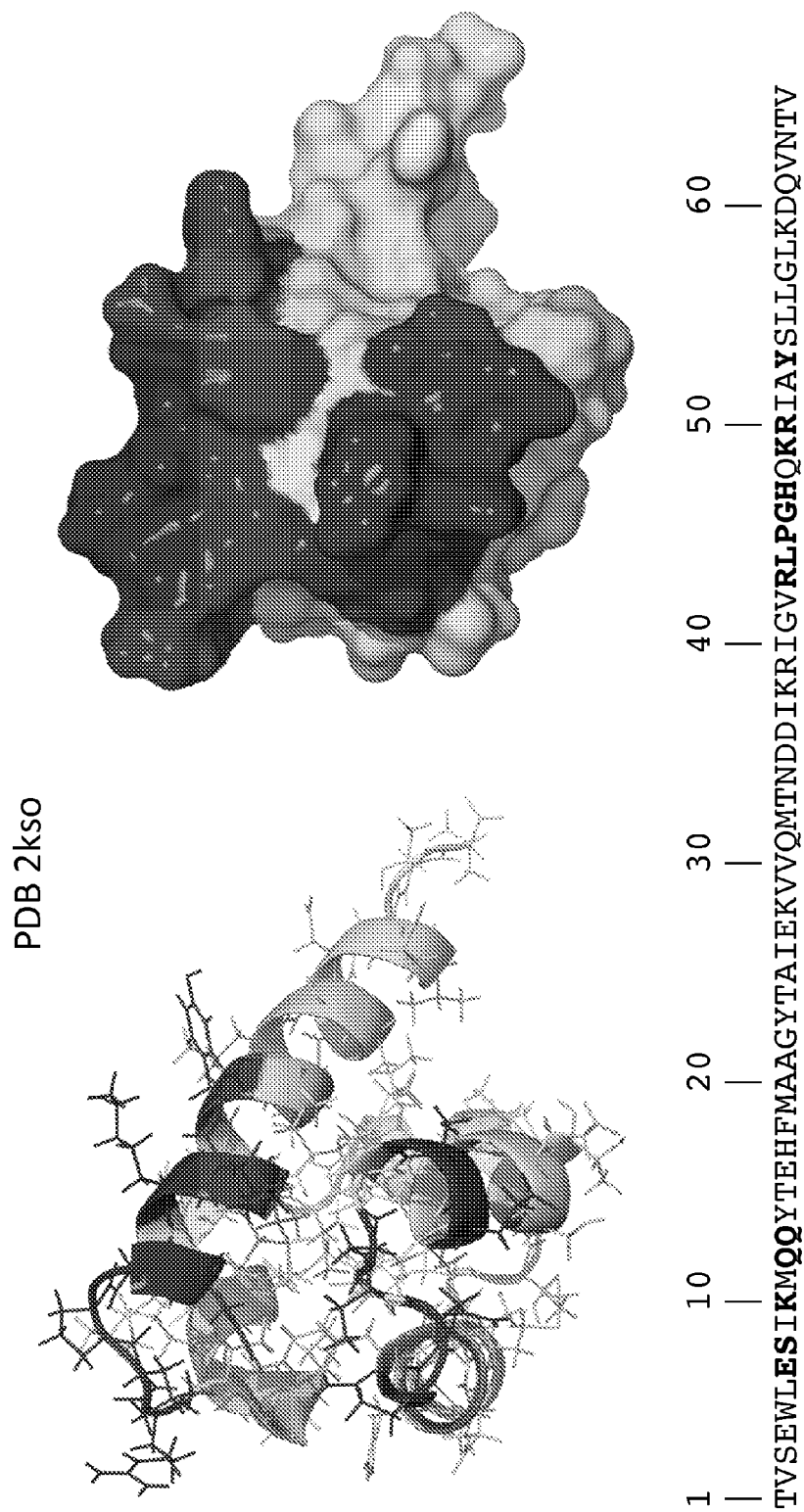
Figure 8:
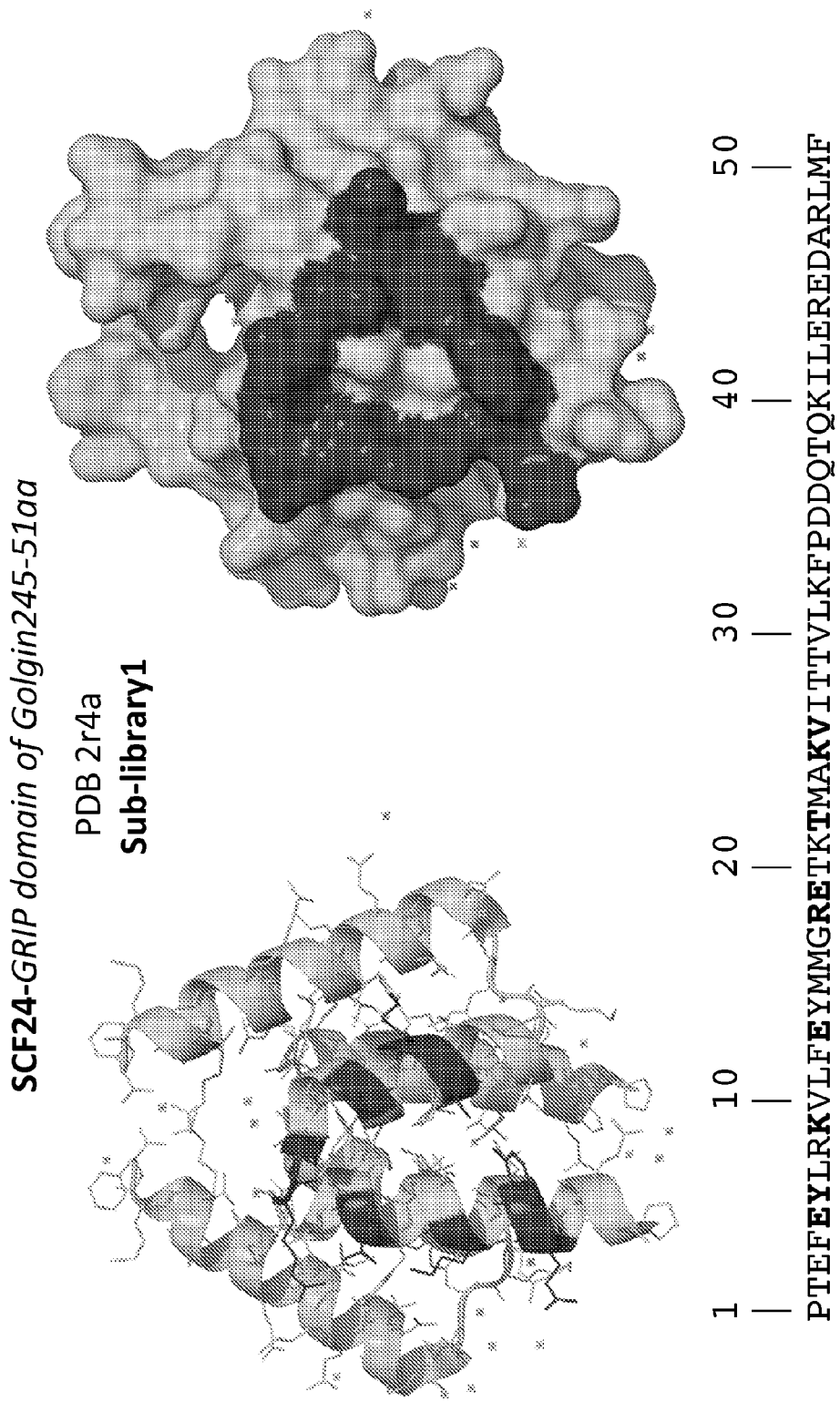
Figure 9:
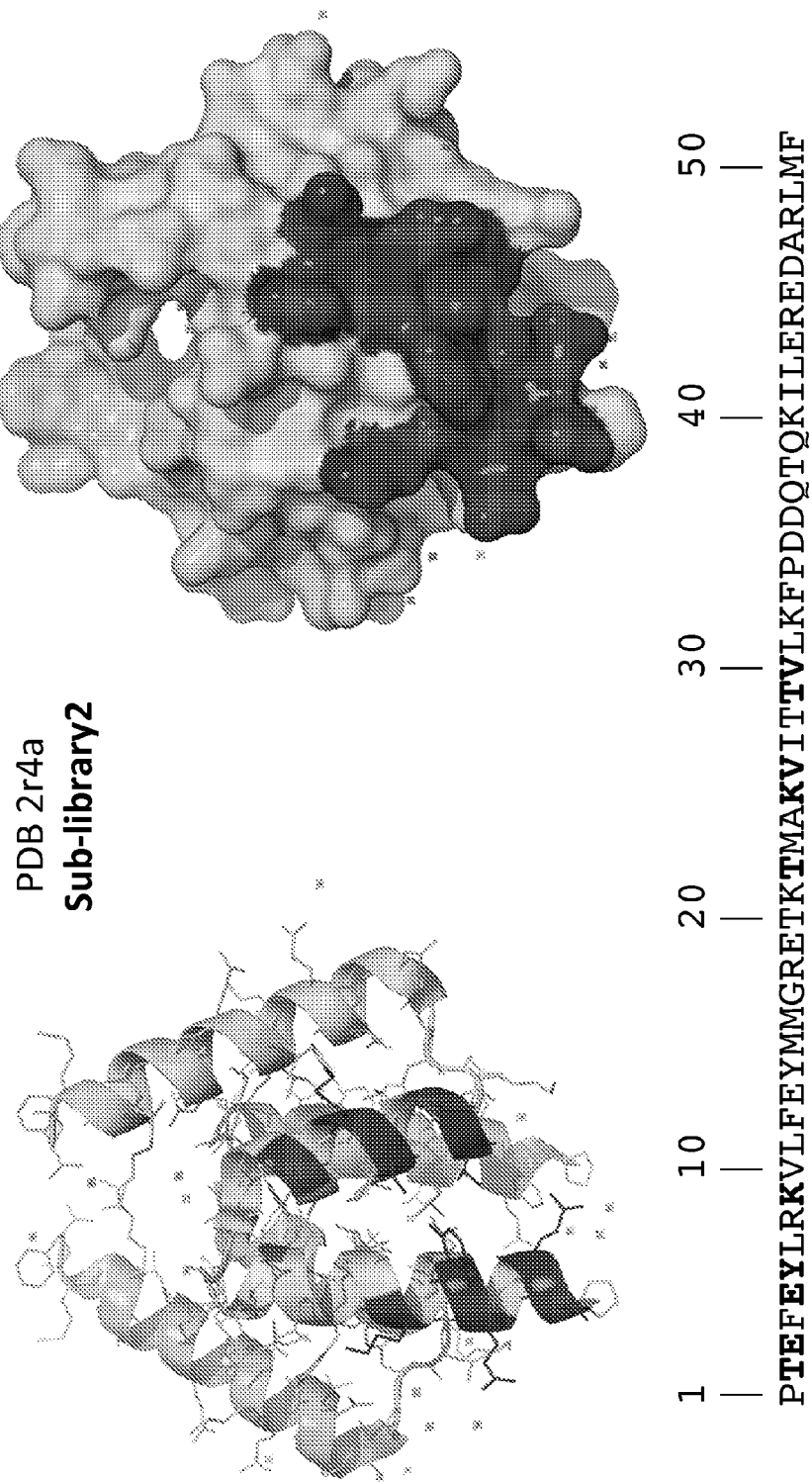
Figure 10:
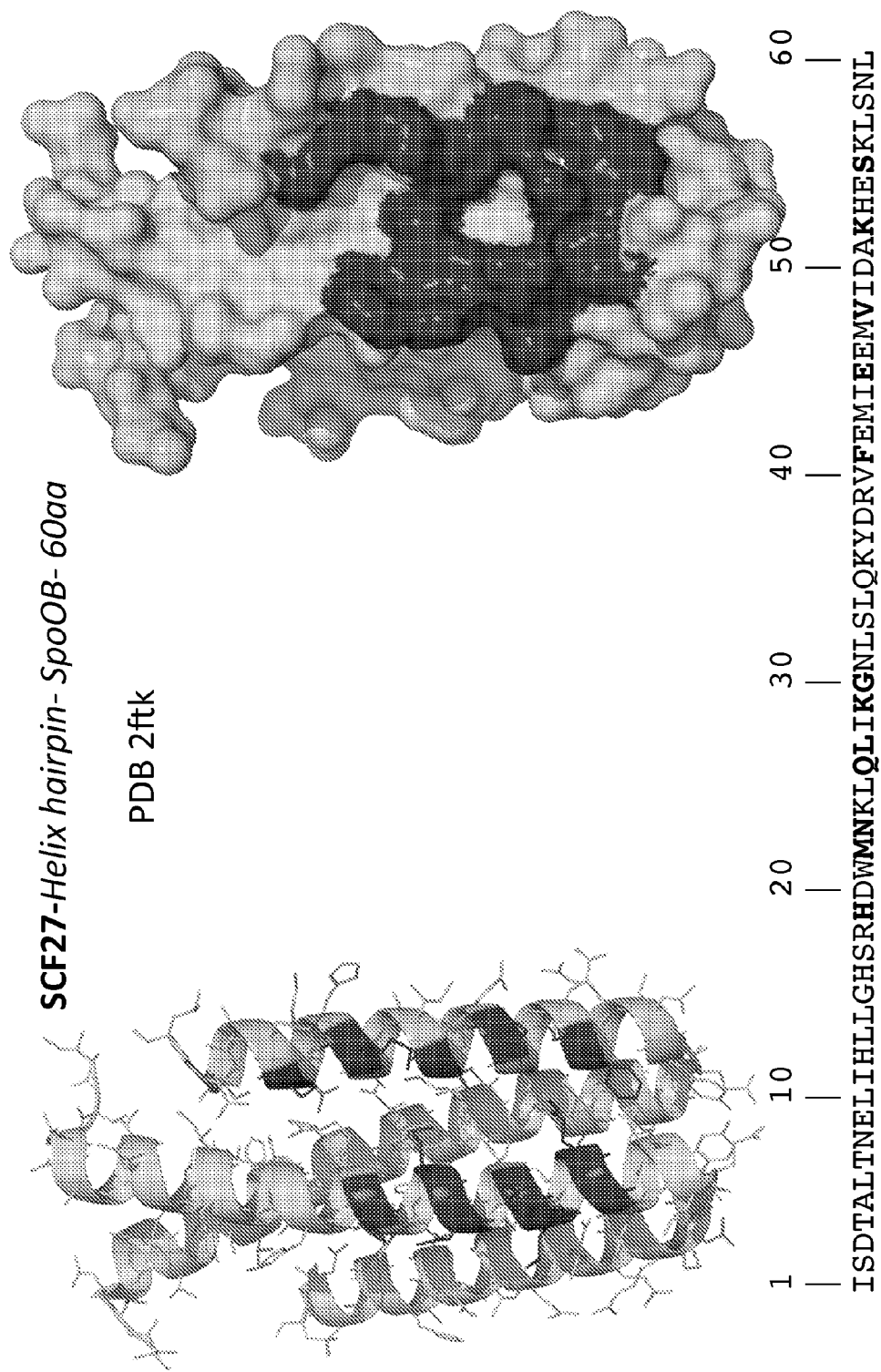
Figure 11:
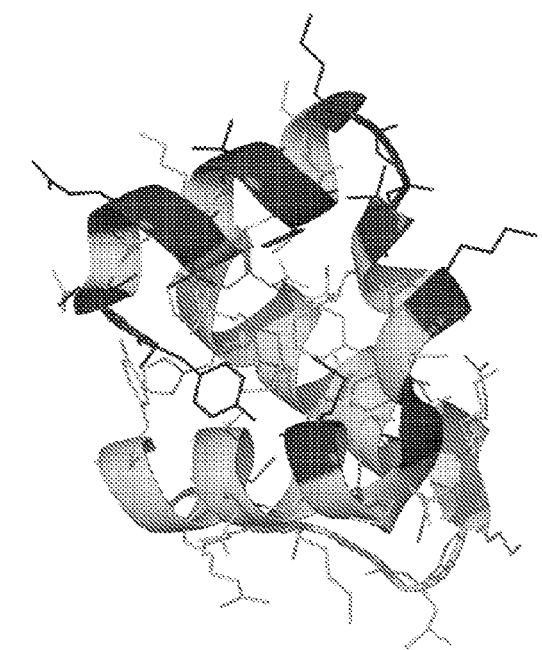
Figure 12:
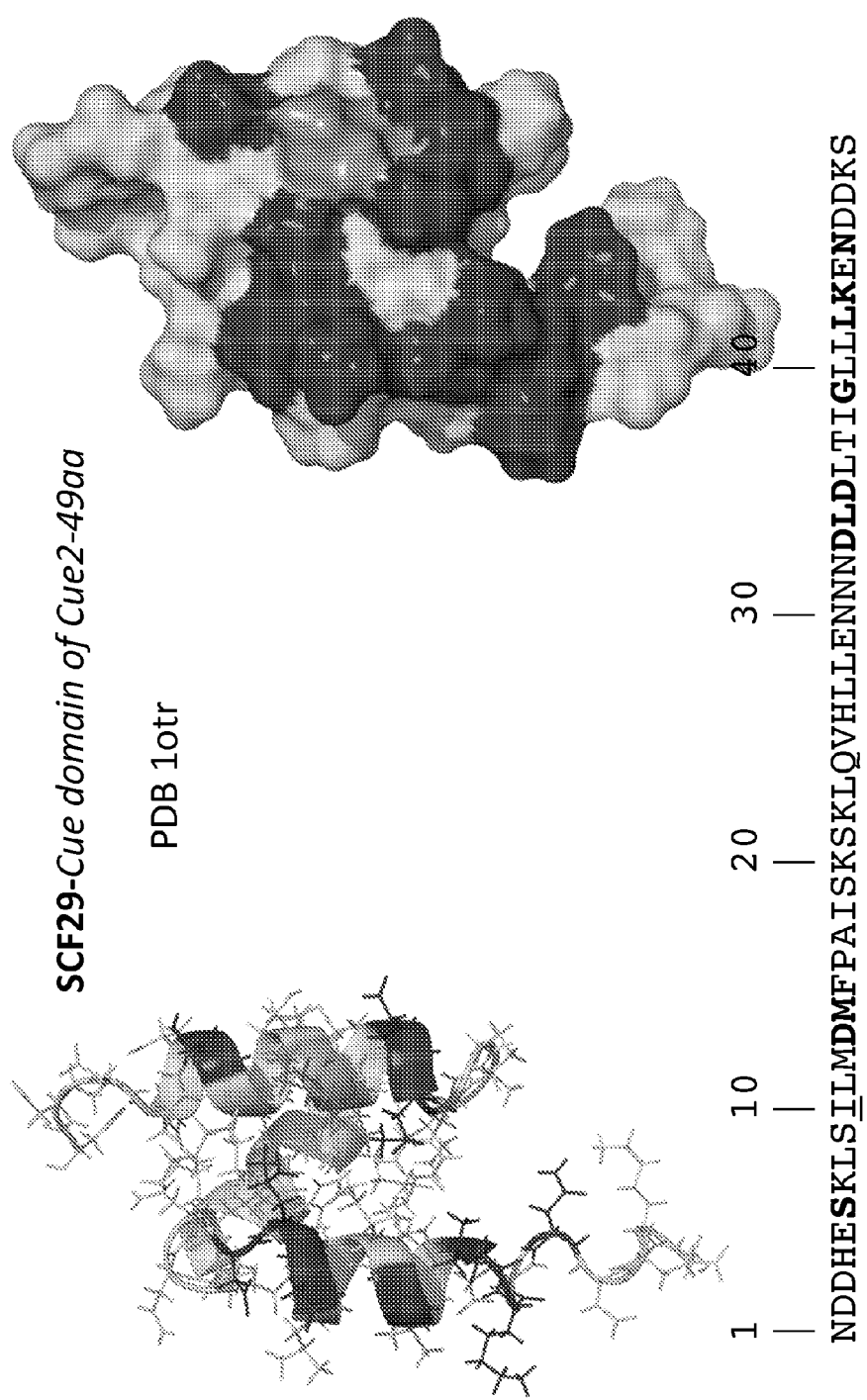
Figure 13:
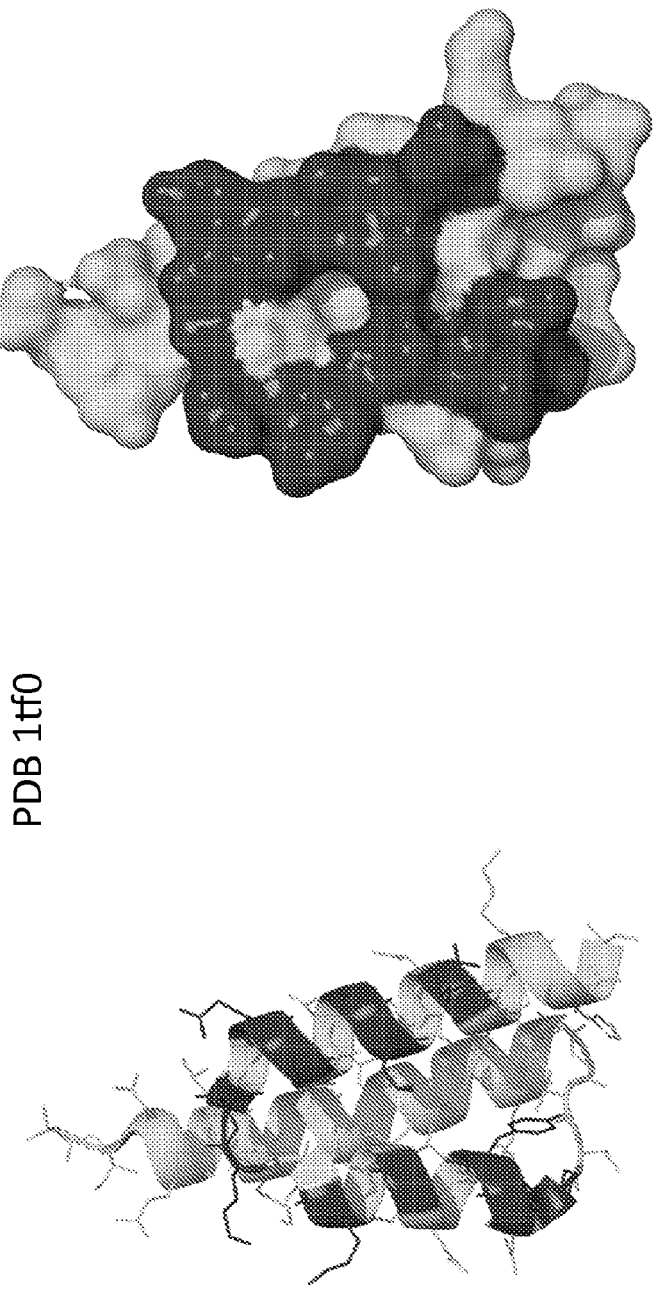
Figure 14:
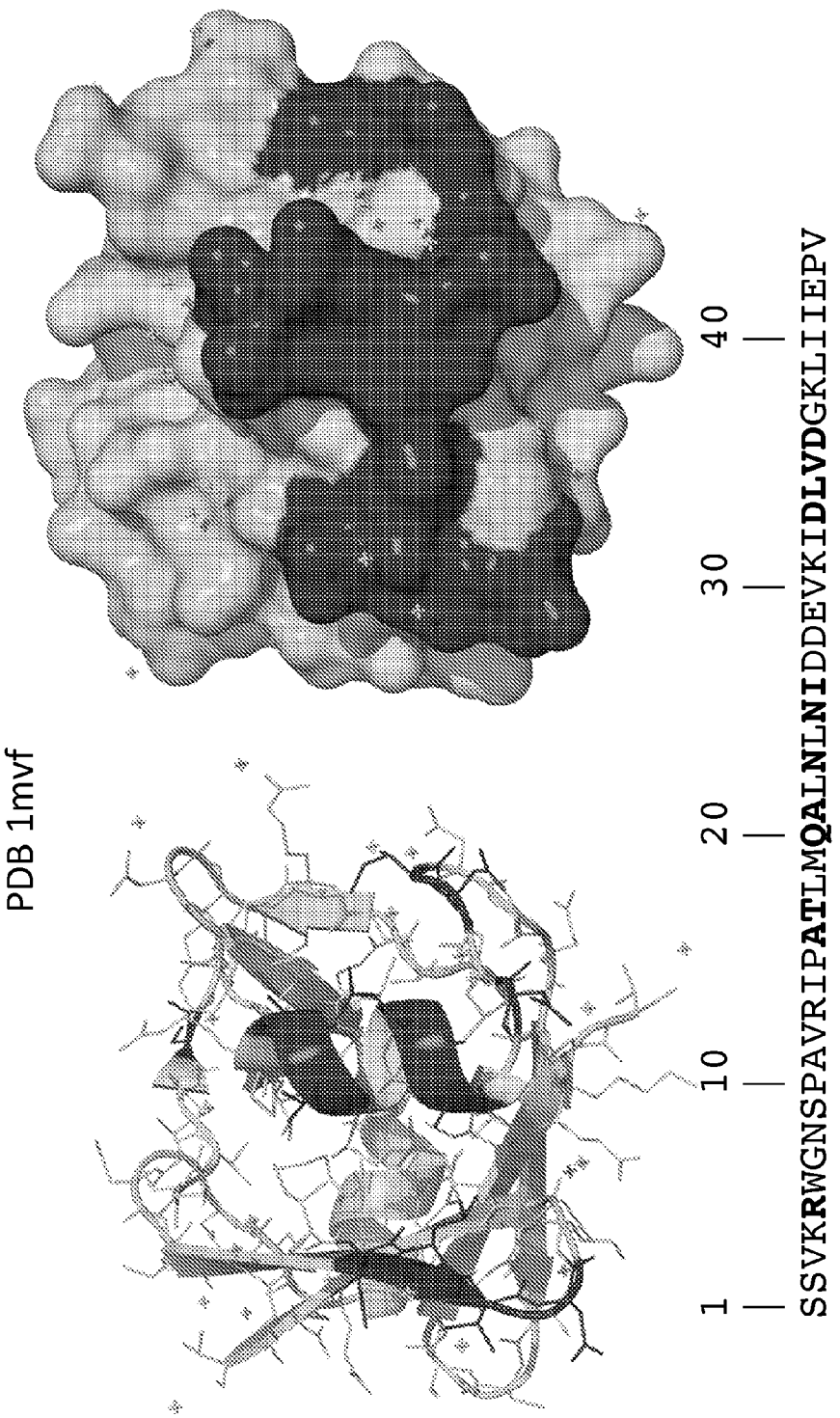
Figure 15:
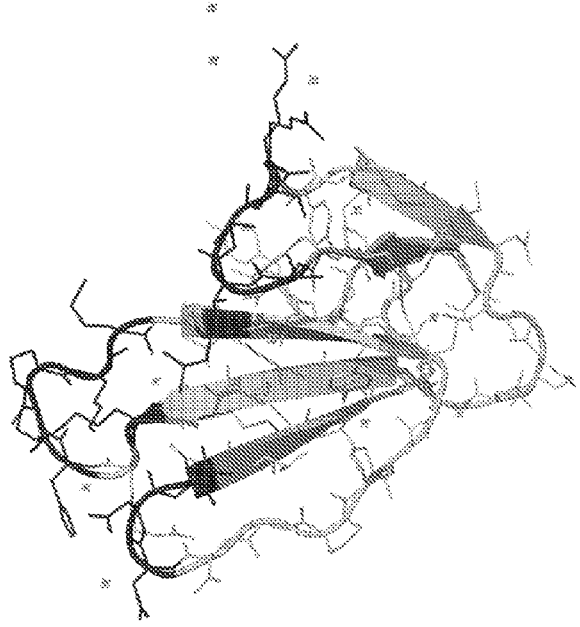
Figure 16:
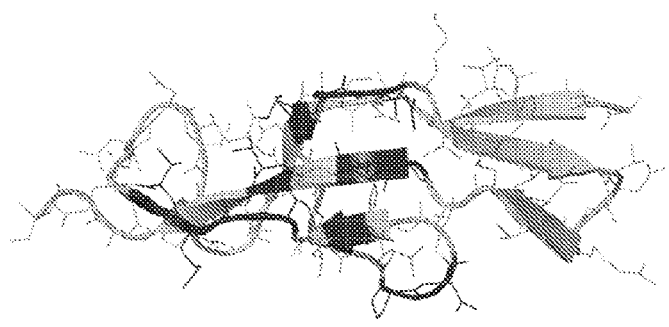
Figure 17:
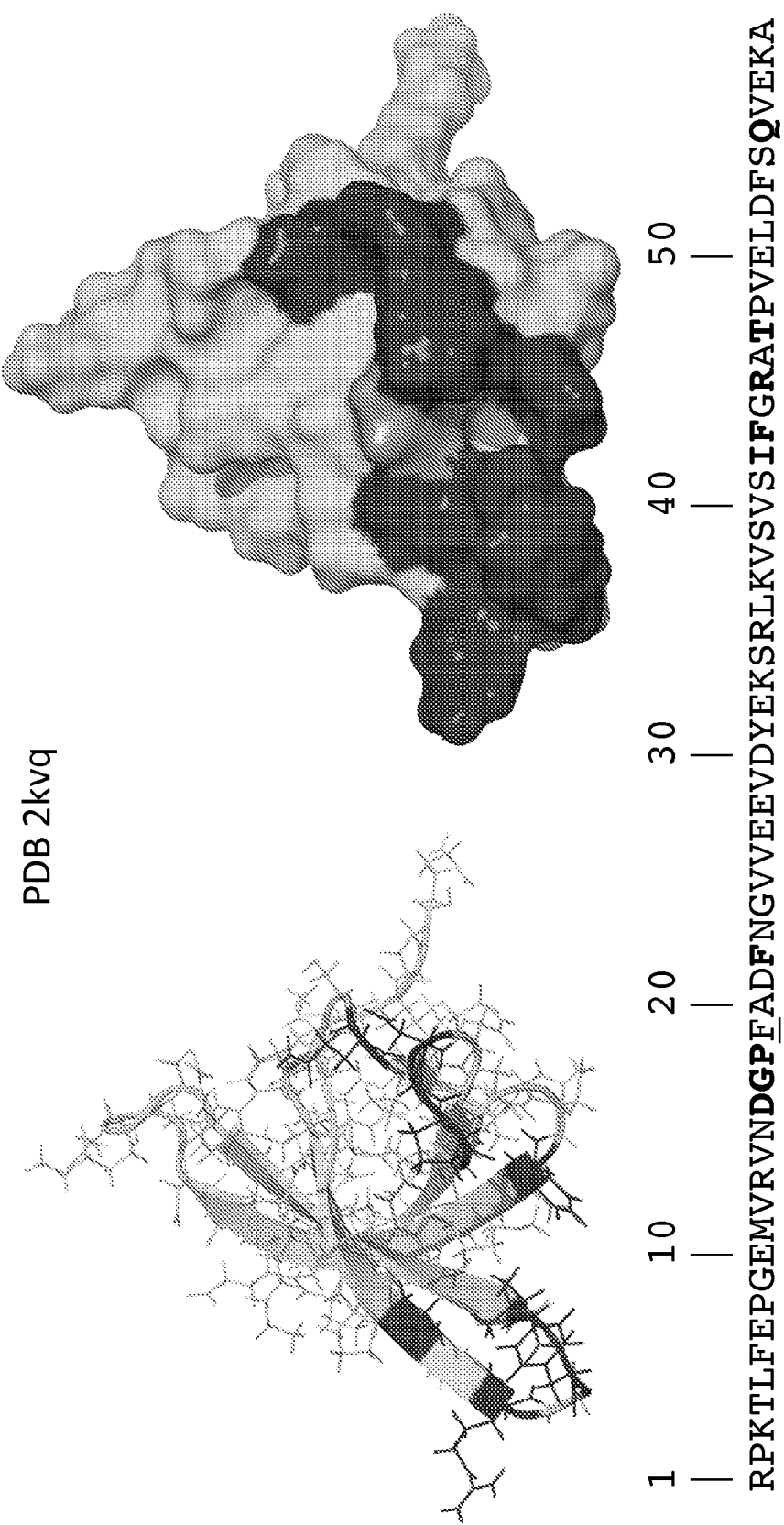
Figure 19:
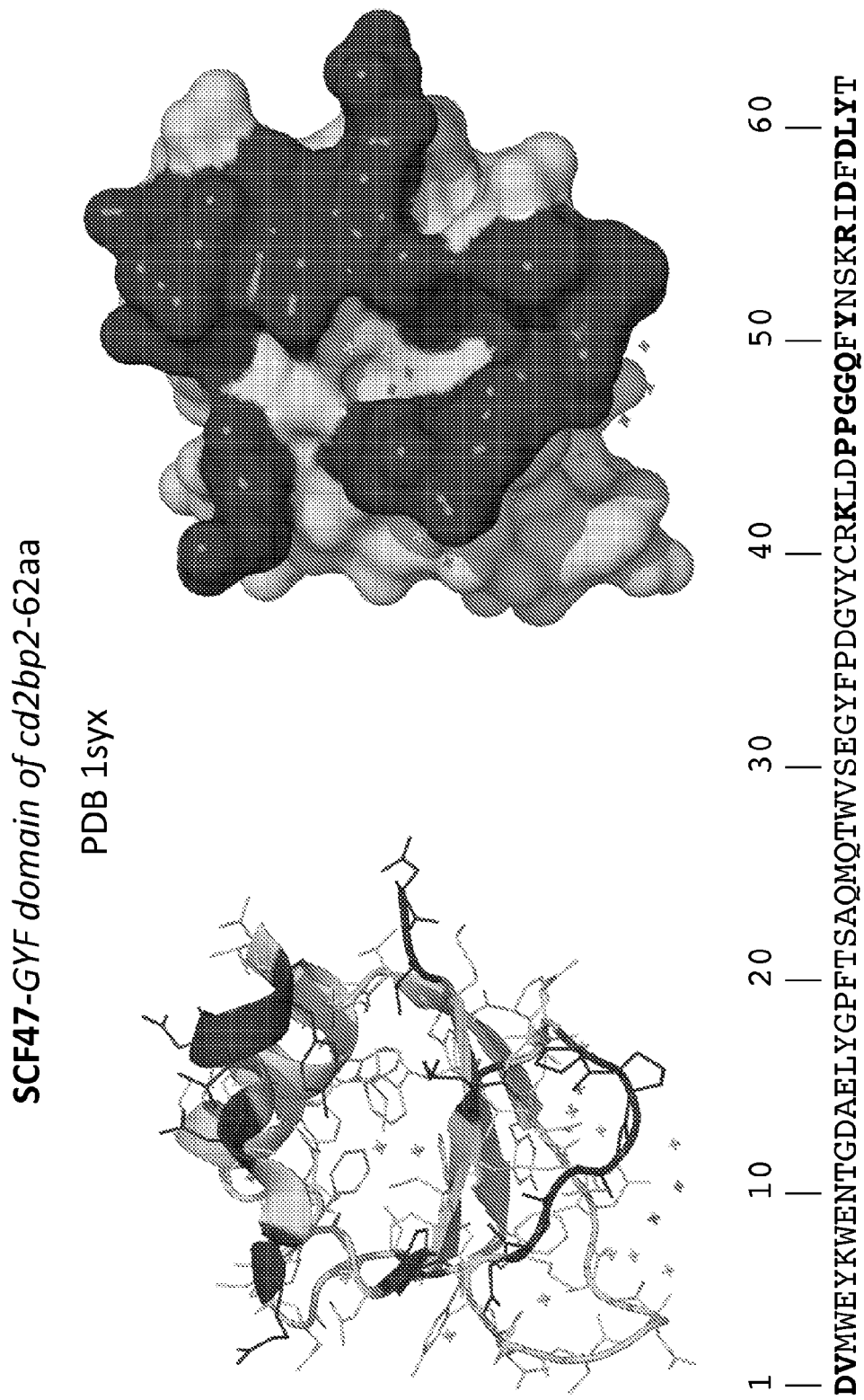
Figure 20:
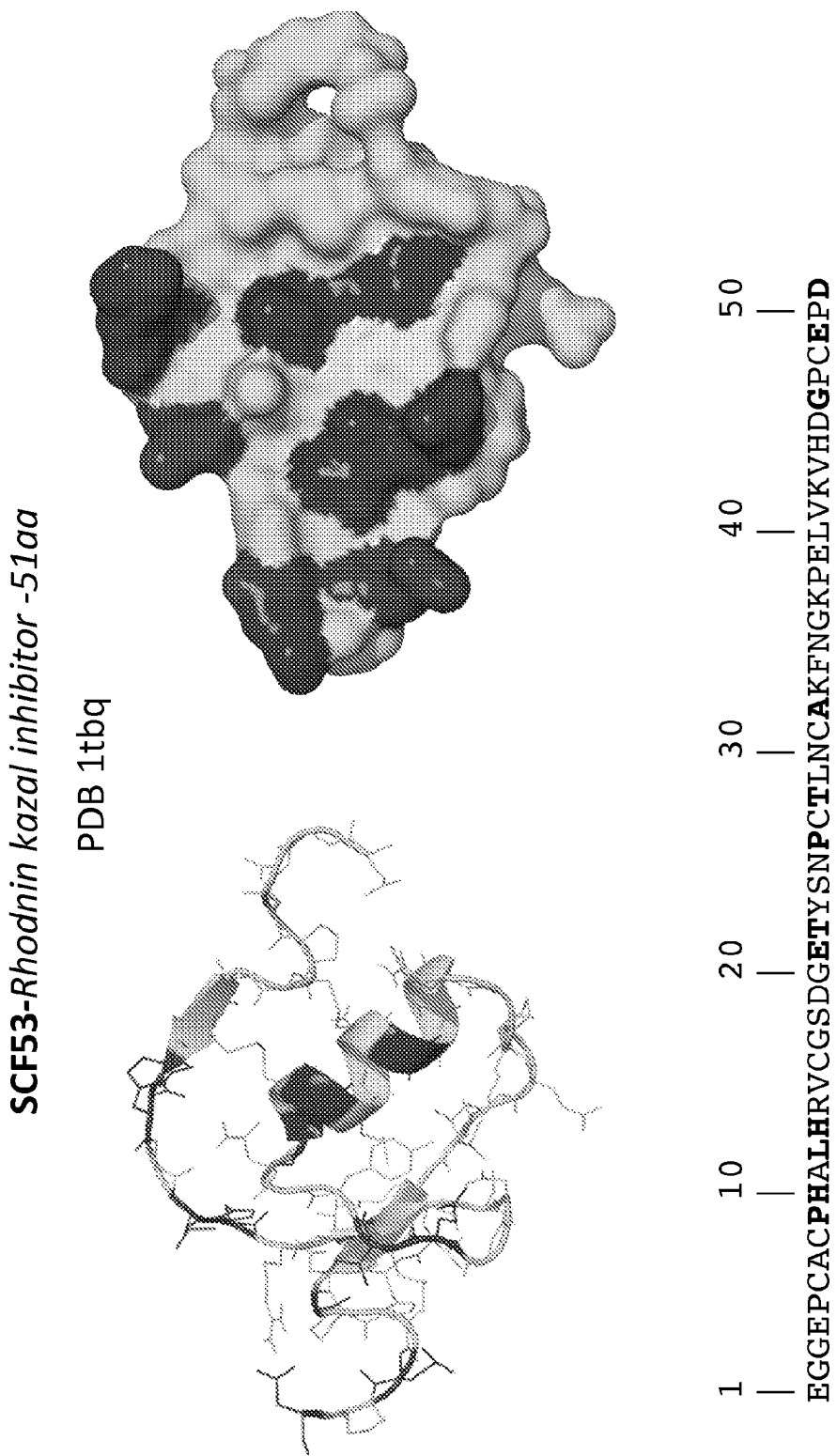
Figure 21:
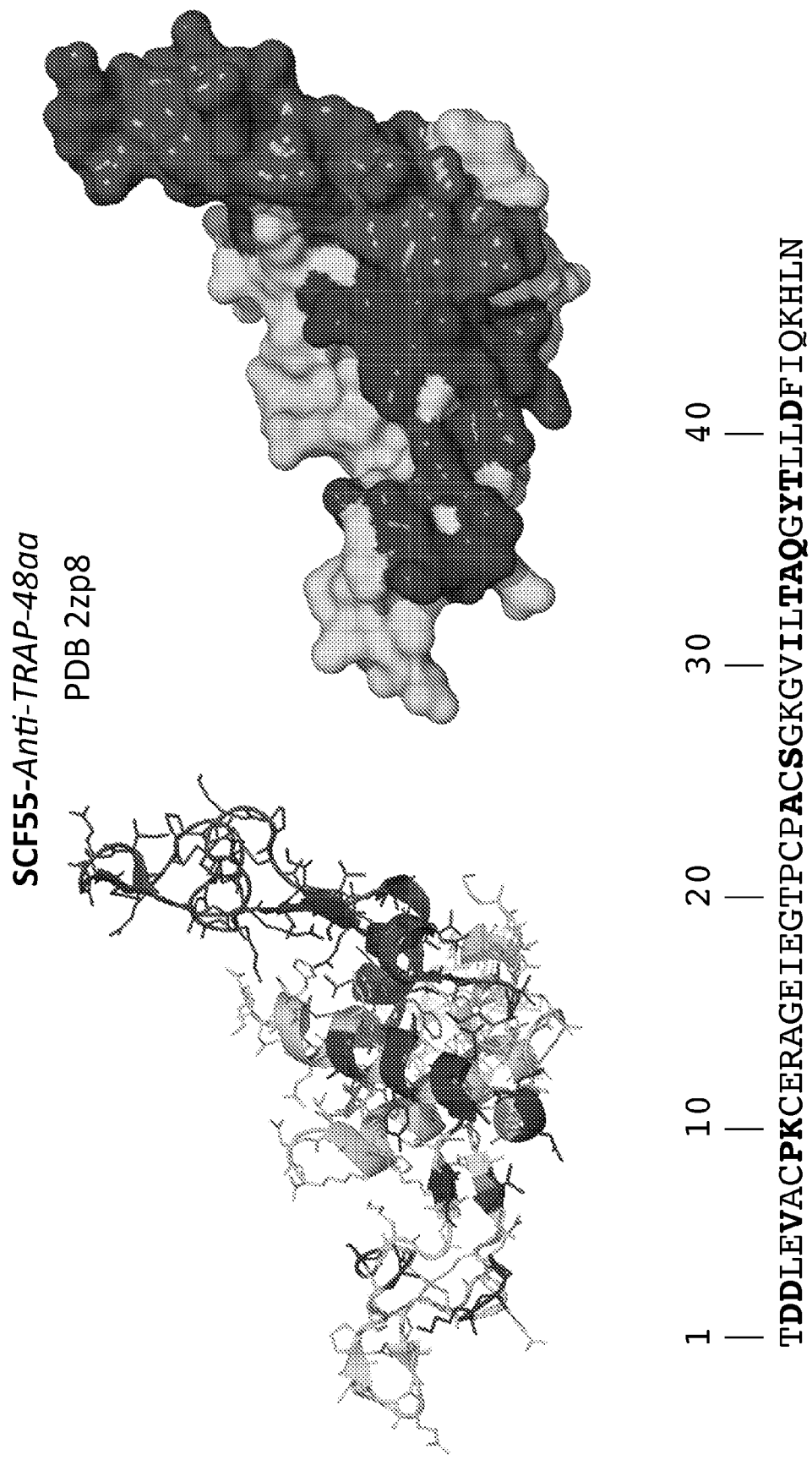
Figure 22:
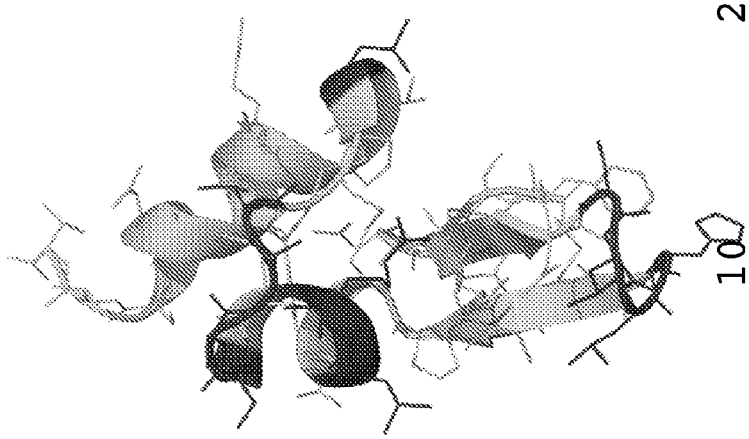
Figure 23:
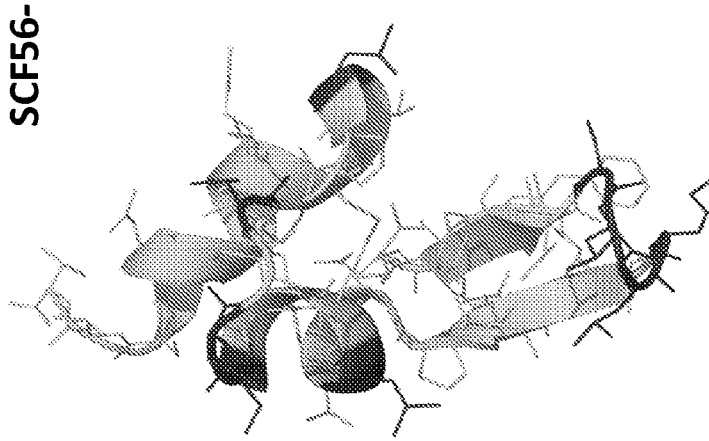
Figure 24:
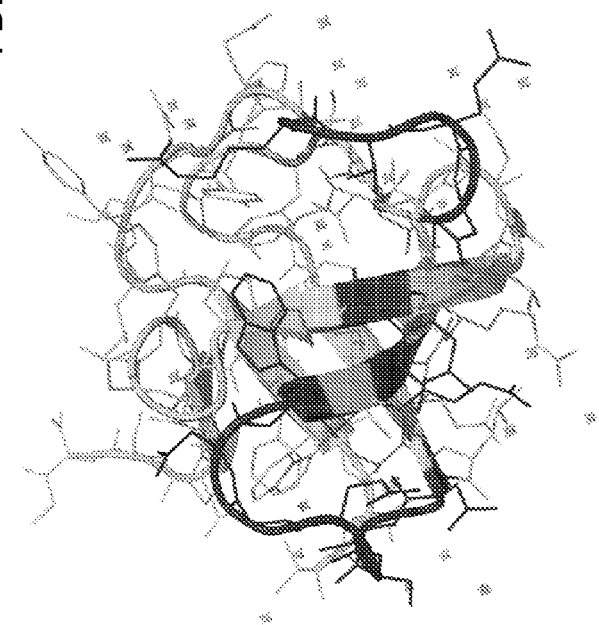
Figure 25:
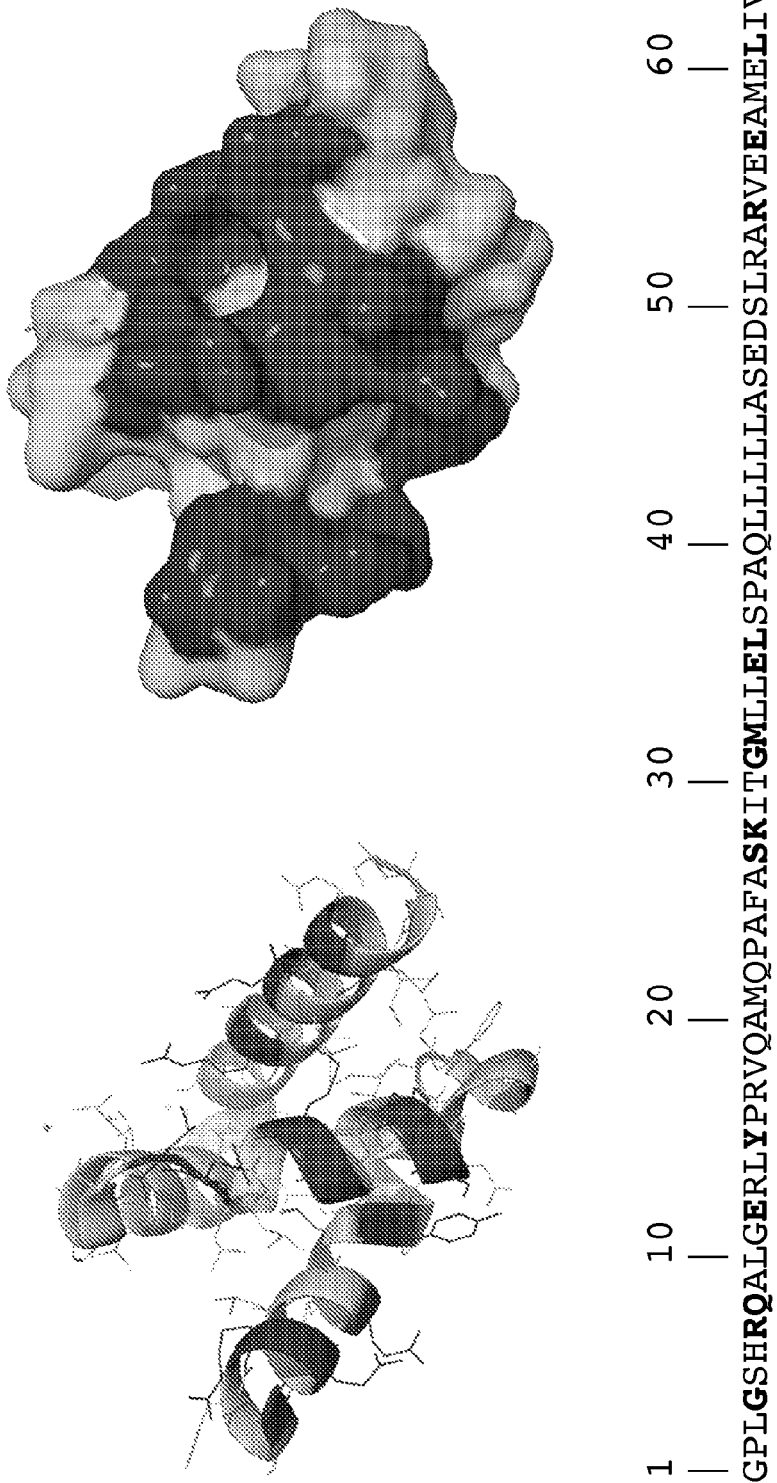
Figure 26:
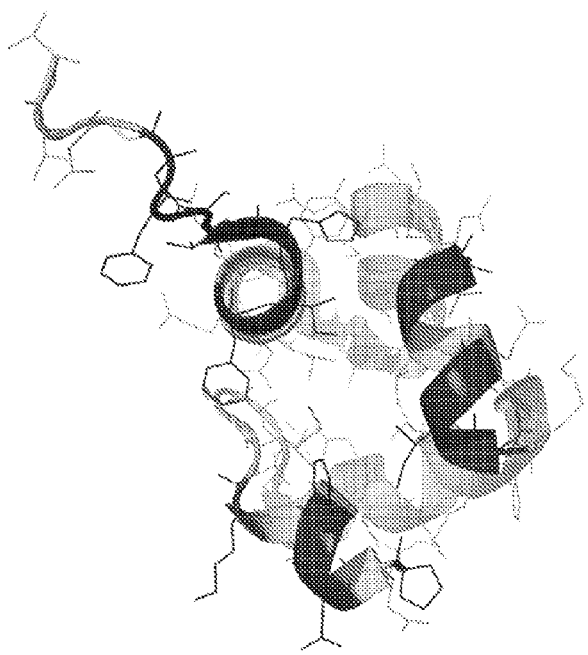
Figure 28:
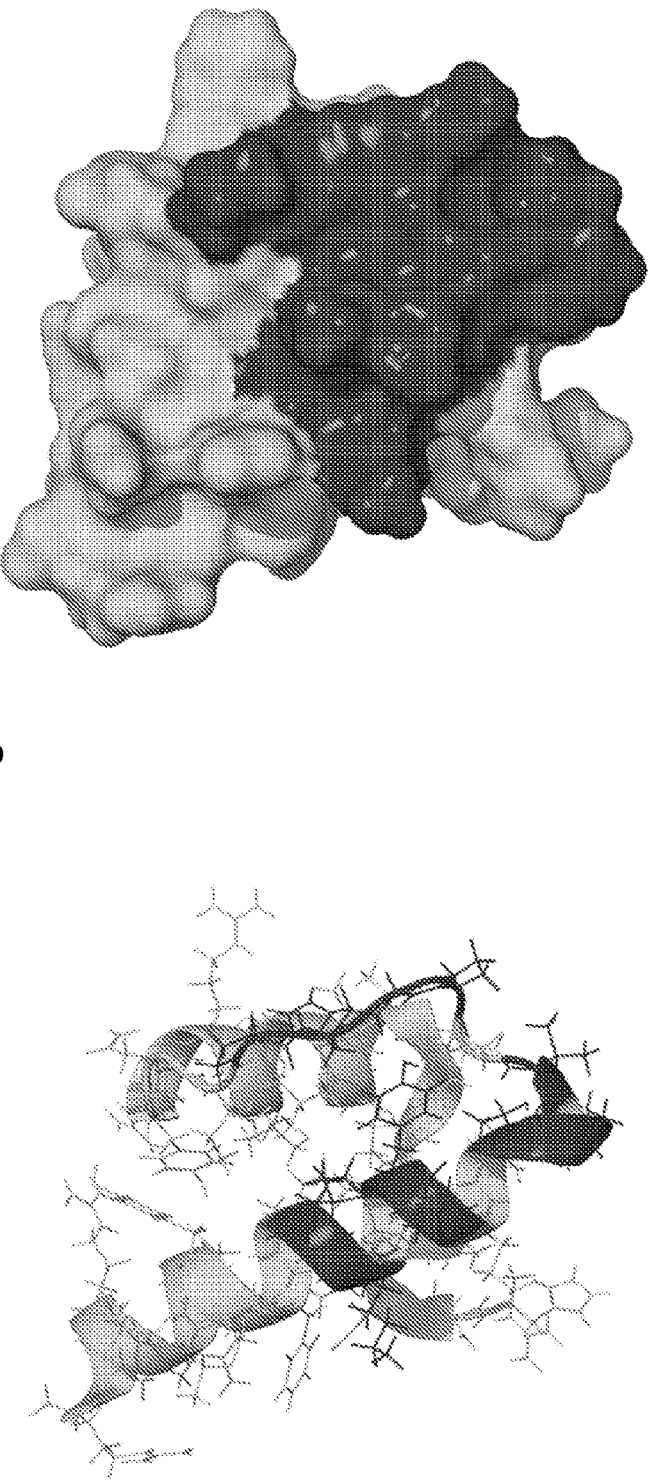
Figure 29:
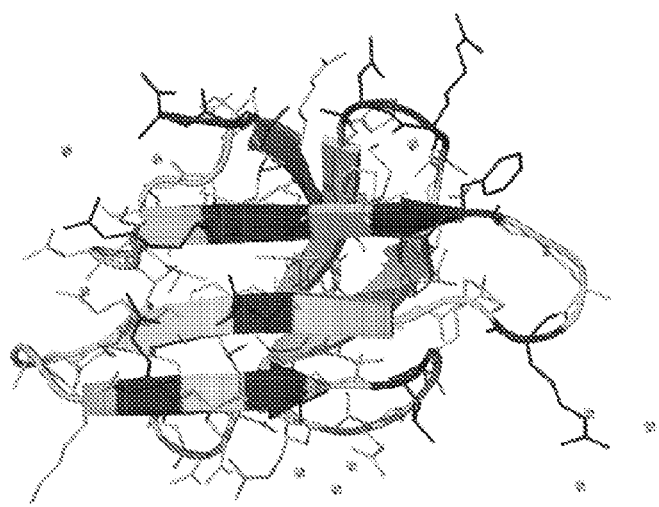
Figure 30:
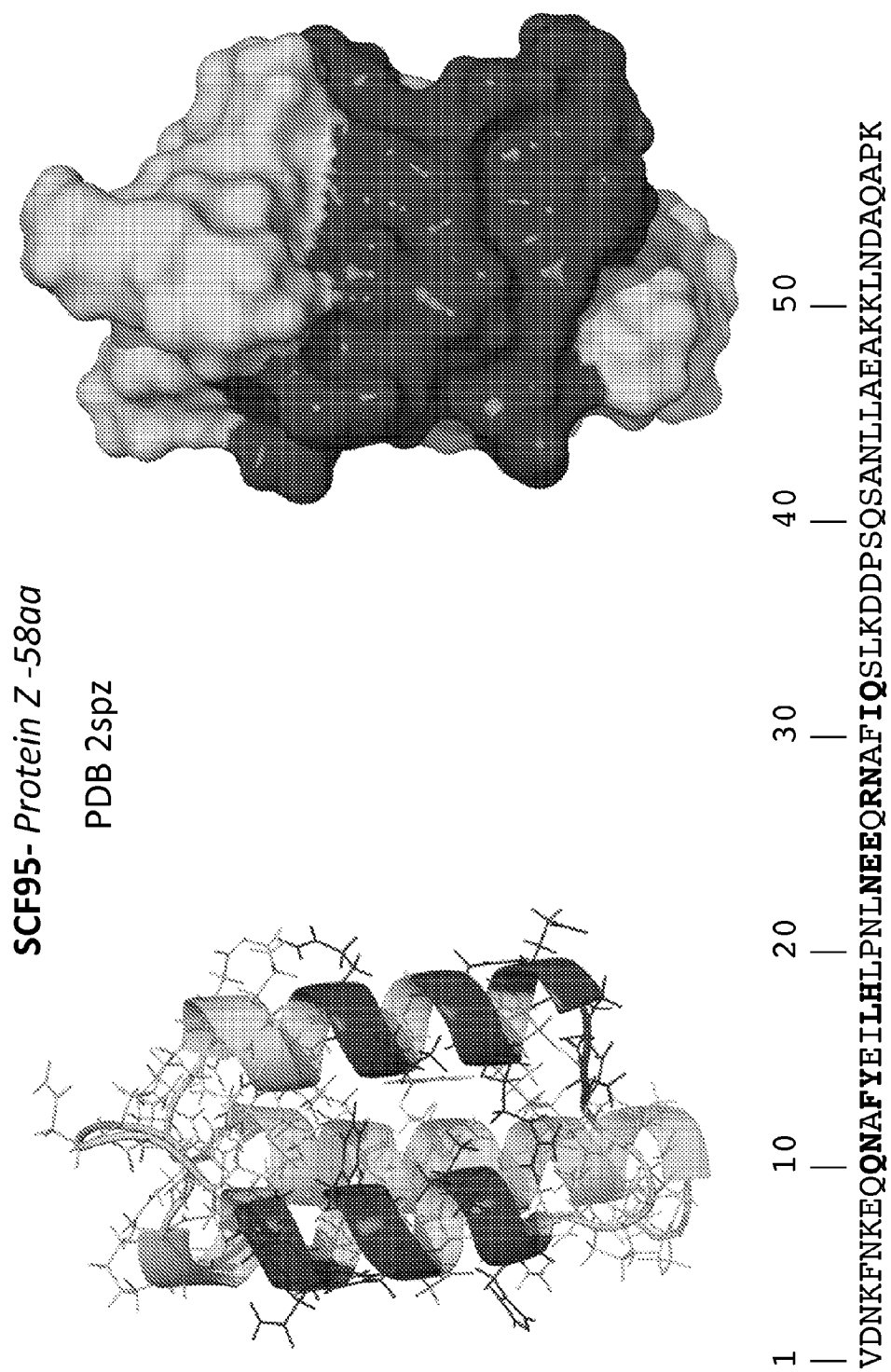

Scaffolded peptidic libraries and methods of screening the same for the identification of compounds that specifically bind to target proteins are provided. The subject libraries each include a plurality of peptidic compounds, where each peptidic compound has a scaffold domain of the same structural motif as the underlying parent scaffold of the library of interest. The scaffolded peptidic libraries are designed to include mutations at a variety of positions. e.g., variant amino acids at positions within a parent scaffold domain. The number and types of mutations define the size and diversity of the library. In some embodiments, the peptidic compounds of the scaffolded peptidic libraries include mutations at non-core positions, e.g., variant amino acids at positions within a parent scaffold domain that are not part of the hydrophobic core of the structure. Structural motifs of scaffold domains of interest are depicted in FIGS. 1-30. Sequences of scaffolds of interest are shown in FIGS. 31-34.

A variety of scaffolded peptidic libraries of peptidic compounds are provided. For library diversity, both the positions of the mutations and the nature of the mutation at each variable position of the scaffold may be varied. In some instances, the mutations are included at non-core positions, although mutations at core positions may also be included. The mutations may confer different functions on the resulting peptidic compounds, such as specific binding to a target molecule. The mutations may be selected at positions of a scaffold domain of interest that are solvent exposed such that the variant amino acids at these positions can form part of a potential target molecule binding surface, although mutations at selected core and/or boundary positions may also be included. In a subject library, the mutations may be concentrated in a variable domain that defines one of several distinct potential binding surfaces of the underlying scaffold domain. Libraries of distinct peptidic compounds are provided that include distinct arrangements of mutations concentrated at a potential binding surface of the structural motif, for example, as depicted in FIGS. 1-30. In some embodiments, the peptidic scaffold is a small protein having a surface suitable for protein-protein interactions. In certain cases, the protein-protein interaction surface of the scaffold is a contiguous surface area having a size of about 500 square angstroms or more (e.g., about 500 to about 1800 square angstroms). The subject libraries may include compounds that specifically bind to a target molecule via a variable domain located at a potential target binding site of the underlying scaffold domain. Mutations may be included at the potential binding surface to provide for specific binding to a target molecule without significantly disrupting the underlying scaffolded peptidic structure.

In the subject methods, a scaffolded peptidic library is contacted with a target molecule to screen for a compound of the library that specifically binds to the target with high affinity. The subject methods and libraries find use in a variety of applications, including screening applications.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the various aspects of the invention, the structures and sequences of members of the various libraries are described first in greater detail, followed by a description of methods of screening and applications in which the libraries finds use.

Scaffolded Peptidic Libraries

As summarized above, aspects of the invention include libraries of scaffolded peptidic compounds where each peptidic compound has a scaffold domain of the same structural motif as the underlying parent scaffold of the library of interest. The peptidic compounds of the subject scaffolded libraries may include mutations at various positions of the structural motif, e.g., variant amino acids at non-core positions within a scaffold domain of interest. Structural motifs and sequences of scaffold domains of interest are depicted in FIGS. 1-34.

As used herein, the terms "scaffold", "scaffolded" and "scaffold domain" are used interchangeably and refer to an underlying peptidic framework (e.g., a consensus sequence or motif) from which a library of compounds arose, and against which the compounds are able to be compared (e.g., using sequence alignment and consensus sequence analysis). When a compound of a library arises from amino acid mutations at various positions within a scaffold, the amino acids at those positions are referred to as "variant amino acids." The underlying scaffold sequence includes those residues that are "fixed amino acids" (e.g., non-variant amino acids). Such variant amino acids may confer on the resulting peptidic compounds different functions, such as specific binding to a target protein. As used herein, the terms "scaffold domain", "scaffolded" and "scaffold" may be applied to a protein of interest (e.g., a protein of FIGS. 1-34) to refer to a peptidic library or compound. A scaffolded peptidic library and compounds thereof may have a structural motif similar to that of the underlying protein scaffold of interest (e.g., a protein of FIGS. 1-34). Such structural motifs may be characterized and compared structurally as a combination of particular secondary and tertiary structural elements (e.g., alpha helix, beta sheet, mixed alpha and beta, and monomers, dimers, trimers), or alternatively, as a comparable primary sequence of amino acid residues. Structural motifs of scaffold domains of interest are depicted in FIGS. 1-30. Amino acid sequences of scaffold domains of interest (e.g., the sequences of FIGS. 1-30 and sequences of scaffolds 1-70 of FIGS. 31-34) that may be employed herein as scaffold domains may also be found in the Protein Data Bank database (www.rcsb.org) or in NCBI's protein database. Scaffold domain sequences of interest include those proteins of interest described in FIGS. 1-34, native protein sequences of related family members of those proteins of interest, modified sequences of those proteins of interest that include a limited number (e.g., 10 or less, such as 1, 2, 3, 4, 5, 6, 7, 8, 9 or 10 residue modifications that do not adversely affect the structural motif) of pre-existing amino acid sequence modifications (such as additions, deletions and/or substitutions), or a fragment thereof, or an analogue thereof. A scaffold domain may be L-peptidic, D-peptidic or a mixture of L- and D-amino acid residues.

In some instances, the library is a phage display library that may be screened for binding to any convenient targets, such as L-target proteins and D-target proteins. In other instances, the library is comprised of D-peptidic compounds (e.g., chemically synthesized compounds). Such D-peptidic libraries may be screened for binding against any convenient targets, such as L-protein targets.

In some cases, a "scaffold domain" is referred to as a "parent amino acid sequence." As used herein, the terms "parent amino acid sequence", "parent scaffold" and "parent polypeptide" refer to a polypeptide comprising an amino acid sequence from which a variant peptidic compound arose and against which the variant peptidic compound is being compared. In some cases, the parent polypeptide lacks one or more of the modifications disclosed herein and differs in function compared to a variant peptidic compound as disclosed herein. The parent polypeptide may comprise a native protein sequence or other scaffold sequence with pre-existing amino acid sequence modifications (such as additions, deletions and/or substitutions).

A scaffold domain may be any convenient polypeptide, or fragment thereof that includes the structural motif of a parent scaffold of interest, whether naturally occurring or synthetic. Scaffold domains of interest include DiGeorge syndrome critical region 8 (DGCR8) dimerization domain; Get5 C-terminal domain; H-NS domain from *E. coli*; KorB c-terminal dimerization domain; Lsr2 dimerization domain; PKA-RI alpa dimerization/docking domain (bovine); UBA domain of p62; N-terminal domain of SpoVT; Collagen XI trimerization domain; Symfoil 4P trimer (designed beta-trefoil); C-terminal domain of RNA polymerase alpha subunit; EphA2 SAM domain; GRIP domain of Golgin245; SpoOB-Helix hairpin domain; C-terminal domain of Ku; CUE domain of Cue2 protein; DNA helicase RuvA domain; GA domain of protein G; Hirustasin; Thrombomodulin (EGF type domains); Coagulation factor VIIa; PEM-1 like protein; Fasciculin-2; CD46 extracellular domain; Nucleotide exchange factor C-terminal domain; Tudor domain of TDRD3; Transcription antitermination protein NusG; CCL2 chemokine; ThiS protein in complex with ThiF; Chymotrypsin inhibitor; Carboxypeptidase inhibitor; GYF domain of CD2bp2; Cdk regulatory subunit1; CN2 toxin; CHD4-PHD finger domain; GATA type zinc finger; Leech derived tryptase inhibitor; Rhodnin Kazal inhibitor; MHC ClassII p41 fragment; Anti-TRAP; TNF Receptor17 (BCMA); NZF zinc-finger domain; Amaranth alpha amylase inhibitor; Sac7d (Nanofitins); APPI Kunitz domain; Fyn SH3 domain (Fynomers); E3 ubiquitin-protein ligase UBR5; DNA repair endonuclease XPF; Chain B:rad23 hom.B, xpcb domain; Chain B:dsk2-uba domain; Chain C:LEM domain/emerin; Chain A:Protein YBL047C UBA domain; Chains A/B: PKA docking/dimerization domain; Chain C: GspC; Chain A: Phage IF1 attachment protein G3P; Chain A: cd2ap sh3; Chain B: micronemal protein 6, EGF-like domain; Chain B: colicin-A; Chain B: Rubredoxin 2; Chain E: EGF domain of LDLR; Chain I: engineered protease inhibitor, SGPI scaffold; Chain B: engineered hck sh3; N-terminal fragment: NTL9; Brazzein; Insulin growth factor binding protein (IGFBP); Turkey ovomucoid, third domain (OMTKY3); Viscotoxin A1; Chromobox protein homolog 5; Villin headpiece subdomain, Protein Z domain; and enantiomers thereof; and fragments thereof; and mimics thereof.

Figure 33:
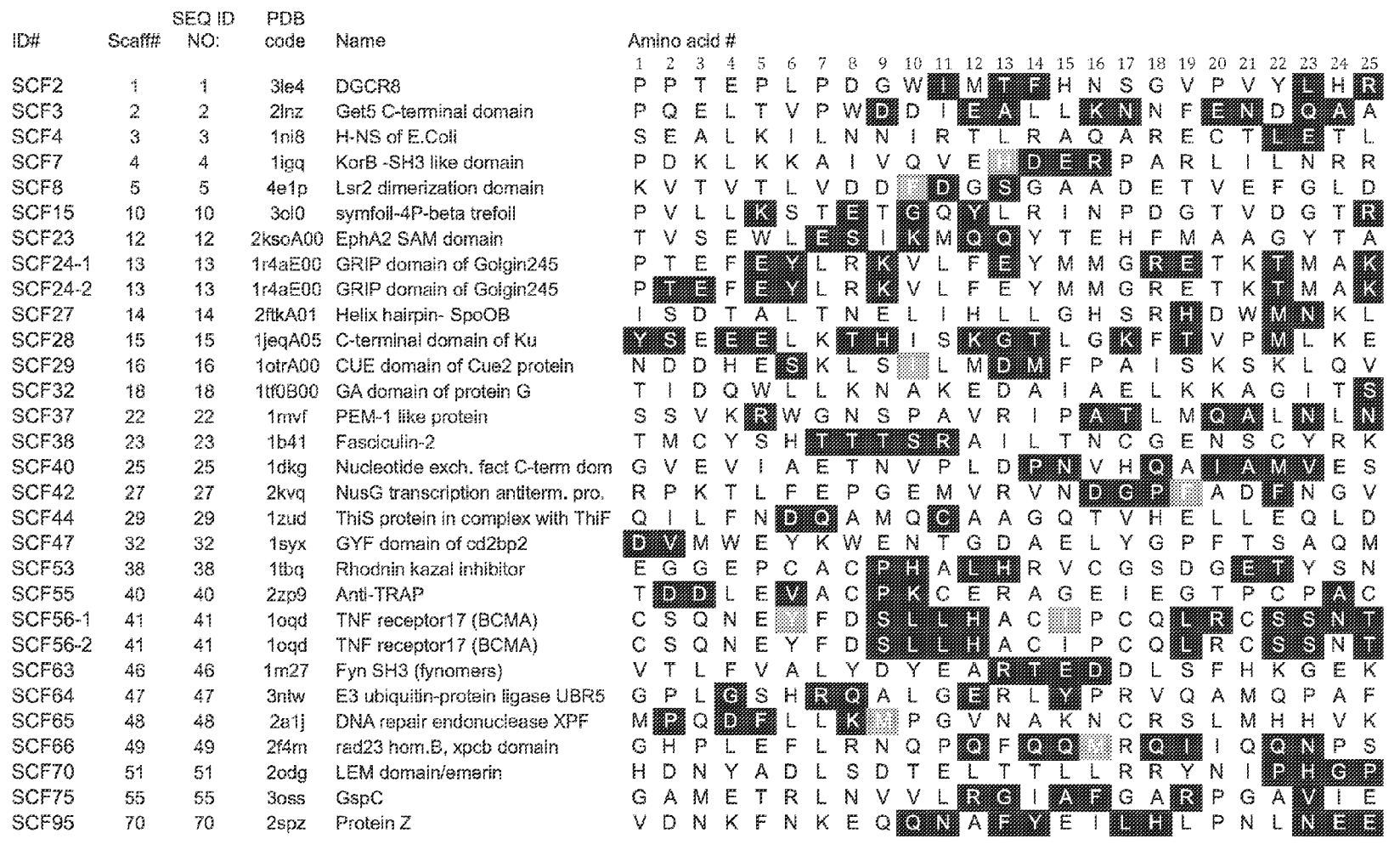
Figure 34:
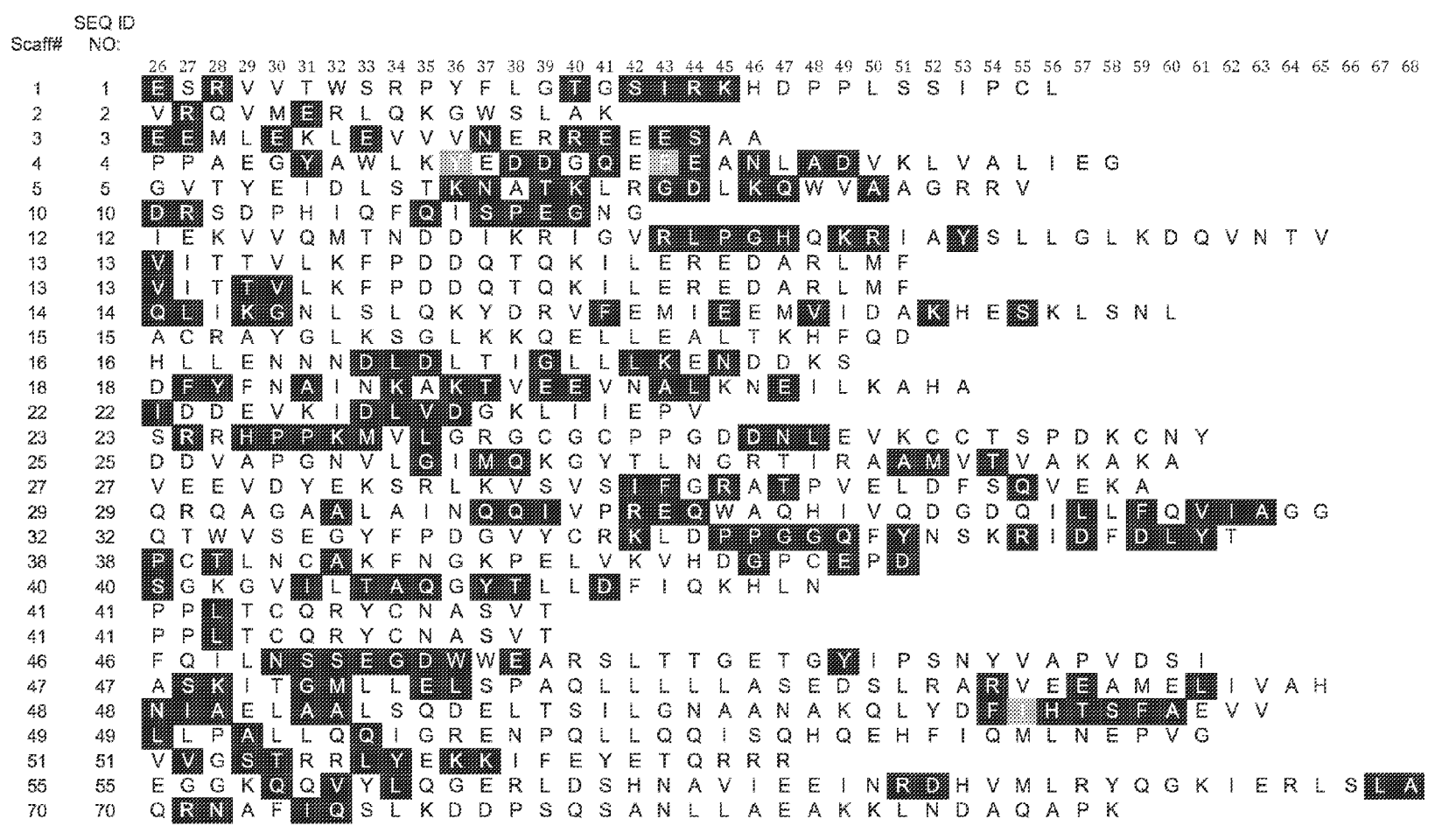

In some embodiments, the scaffolded peptidic library includes one of scaffolds #1-70 of FIGS. 31-32 as a scaffold domain. In certain embodiments, the scaffolded peptidic library includes one of scaffolds #1, 2, 3, 4, 5, 10, 12, 13, 14, 15, 16, 18, 22, 23, 25, 27, 29, 32, 38, 40, 41, 46, 47, 48, 49, 51, 55 and 70 of FIGS. 33-34 as a scaffold domain.

In certain embodiments, a scaffold domain includes an underlying sequence (e.g., a consensus sequence of fixed amino acid residues) having 60% or more amino acid sequence identity, such as 70% or more, 80% or more, 85% or more, 90% or more, 95% or more or 98% or more amino acid sequence identity to a corresponding amino acid sequence set forth in one of the sequences of FIGS. 1-34. A scaffold domain sequence may include 1 or more, such as 2 or more, 3 or more, 4 or more, 5 or more, 10 or more, 15 or more, or even 20 or more additional peptidic residues compared to a native parent protein sequence, e.g., in the form on a N-terminal or C-terminal extension sequence or in the form of an insertion mutation. In some cases, 30 or less additional peptidic residues, such as 1-20 residues, 2-10 residues, or even 2-5 additional peptidic residues are included in the scaffold domain sequence. Alternatively, a scaffold domain sequence may include fewer peptidic residues compared a native parent protein sequence, such as 1, 2, 3, 4, 5, 6, 7, 8, 9 or 10, or even fewer residues, e.g., by having deletions at the N-terminal and/or C-terminal, or modifications at locations in the sequence that do not adversely affect the structural motif.

A mutation in a scaffold domain may include a deletion, insertion, or substitution of an amino acid residue at any convenient position to produce a sequence that is distinct from the reference scaffold domain sequence. As used herein, the term "mutation" is a deletion, insertion, or substitution of an amino acid(s) residue or nucleotide(s) residue relative to a reference sequence or motif, such as a scaffold sequence or motif.

As used herein, the term "variable region" refers to a continuous sequence of residues that includes one or more variant amino acids. A variable region may also include one or more conserved amino acids at fixed positions. As used herein, the term "fixed region" refers to a continuous sequence of residues that does not include any mutations or variant amino acids, and is conserved across a library of compounds.

As used herein, the term "variable domain" refers to a domain that includes all of the variant amino acids of a particular scaffold. The variable domain may include one or more variable regions, and may encompass a continuous or a discontinuous sequence of residues. The variable domain may be part of the scaffold domain.

In some embodiments, the variable domain is located at one surface of the scaffold domain that is capable of participating in protein-protein interactions. As used herein, the term "protein-protein interaction region" refers to a region of the scaffold domain that forms a contiguous surface capable of participating in protein-protein interactions. In some instances the contiguous surface has a surface area of about 500 or more square angstroms. In certain instances, the "protein-protein interaction region" is located in a region of the scaffold domain that makes contact with protein ligands in complexes of the native scaffold protein.

As used herein, the term "core mutation" refers to an amino acid mutation of a peptidic compound that is located at a position in the structure where the sidechain of the residue is not solvent exposed and is part of the hydrophobic core of the structure. In some cases, such residues may be referred to as "buried" residues. Amino acid residues in the hydrophobic core of a peptidic compound are not significantly solvent exposed but rather tend to form intramolecular hydrophobic contacts. As used herein, the term "non-core mutation" refers to an amino acid mutation of a peptidic compound that is located at a position in the structure that is not part of the hydrophobic core of the structure. In some instances, "surface mutations" and "boundary mutations" are "non-core mutations."

As used herein, the term "surface mutation" refers to an amino acid mutation in a scaffold of interest that is located at a position in the scaffold structure that is solvent exposed. Such variant amino acid residues at surface positions of a peptidic compound are capable of interacting directly with a target molecule, whether or not such an interaction occurs.

As used herein, the term "boundary mutation" refers to an amino acid mutation of a scaffold of interest that is located at a position in the scaffold structure that is at the boundary between the hydrophobic core and the solvent exposed surface. Such variant amino acid residues at boundary positions of a peptidic compound may be in part contacting hydrophobic core residues and/or in part solvent exposed and capable of some interaction with a target molecule, whether or not such an interaction occurs. In some cases, such residues may be referred to as "partially buried" residues. One criteria for describing core, surface and boundary residues of a peptidic structure is described by Mayo et al. Nature Structural Biology, 5(6), 1998, 470-475. Such methods and criteria can be modified for use with a scaffold domain of interest.

Any convenient locations of the protein scaffolds of interest may be selected for any convenient number of mutations (e.g., 1, 2, 3, 4, 5 or more mutations). The mutations may be non-core mutations or core mutations, or mixtures thereof. Non-core mutations may include surface mutations and/or boundary mutations. In some cases, five or more of the mutations are non-core mutations. In certain cases, five or more of the mutations are surface mutations. In some embodiments, the scaffold domains of interest (e.g., as described herein) include five or more mutations located at five or more positions as depicted in FIGS. 1-34. In FIGS. 1-34, the sequence and structure locations of a number of variant amino acids of interest are shown (e.g., in red, blue, orange, yellow and magenta colors) in a variety of scaffold domains of interest. Five or more mutations may be introduced at any convenient five or more variant amino acid locations shown.

In some embodiments, each compound of a subject library includes five or more different non-core mutations. In certain cases, each compound of a subject library further includes one or more (e.g., 1, 2, 3, 4, 5, or even more) mutations at core positions. Such core mutations may be included in some cases to compensate for a disruption to the stability of the structural motif.

In some instances, each compound of a subject library includes five or more mutations, such as 6 or more, 7 or more, 8 or more, 9 or more, 10 or more, 11 or more, 12 or more, 13 or more, 14 or more, 15 or more, 16 or more mutations, e.g., at positions selected from those depicted in the scaffolded libraries of FIGS. 1-34. In certain instances, each compound of a subject library includes five or more mutations, such as 5, 6, 7, 8, 9, 10, 11, 12, 13, 14, 15, 16, 16, 18 mutations, e.g., at positions selected from those depicted in the scaffolded libraries of FIGS. 1-34. In certain cases, the five or more mutations are non-core mutations. In some instances, the five or more mutations are surface mutations. In other instances one or more (e.g., 1, 2, 3, 4 or 5) of the five or more mutations are core mutations.

The subject library may include any of the scaffolds set forth in FIGS. 31-32. For any of these scaffolds, mutations may be selected at any convenient positions. In some cases, the mutations of interest are selected from those mutations depicted as black or grey boxes in FIGS. 31-32. In some cases, the mutations of interest are selected from those mutations depicted as black or grey boxes in FIGS. 33-34. In some cases, all of the mutations depicted are included in the subject library. In certain cases, five or more (e.g., 6 or more, 7 or more, 8 or more, 9 or more, 10 or more, 11 or more, 12 or more, 13 or more, 14 or more, 15 or more, 16 or more) of the mutations depicted are included in the subject library. In certain cases, eight or more of the mutations depicted are included in the subject library. In certain cases, ten or more of the mutations depicted are included in the subject library.

In some embodiments, the library includes the scaffold SCF2, DGCR8 (DiGeorge syndrome critical region 8) dimerization domain. In certain embodiments, the SCF2 library includes five or more mutations from those mutations depicted in FIG. 1. In certain embodiments, the SCF2 library includes five or more mutations from those mutations depicted in FIGS. 31-32. In certain embodiments, the SCF2 library includes five or more mutations from those mutations depicted in FIGS. 33-34.

In some embodiments, the library includes the scaffold SCF3, Get5 C-terminal domain. In certain embodiments, the SCF3 library includes five or more mutations from those mutations depicted in FIG. 2. In certain embodiments, the SCF3 library includes five or more mutations from those mutations depicted in FIGS. 31-32. In certain embodiments, the SCF3 library includes five or more mutations from those mutations depicted in FIGS. 33-34.

In some embodiments, the library includes the scaffold SCF4, H-NS domain from *E. coli*. In certain embodiments, the SCF4 library includes five or more mutations from those mutations depicted in FIG. 3. In certain embodiments, the SCF4 library includes five or more mutations from those mutations depicted in FIGS. 31-32. In certain embodiments, the SCF4 library includes five or more mutations from those mutations depicted in FIGS. 33-34.

In some embodiments, the library includes the scaffold SCF7, KorB c-terminal dimerization domain. In certain embodiments, the SCF7 library includes five or more mutations from those mutations depicted in FIG. 4. In certain embodiments, the SCF7 library includes five or more mutations from those mutations depicted in FIGS. 31-32. In certain embodiments, the SCF7 library includes five or more mutations from those mutations depicted in FIGS. 33-34. In certain instances, the SCF7 library includes one or more (e.g., 1, 2 or 3) mutations selected from positions H13, Y36 and F43. In some cases, the H13, Y36 and/or F43 residue is mutated with a hydrophobic residue (e.g., Y, F, L and H).

In some embodiments, the library includes the scaffold SCF8, Lsr2 dimerization domain. In some instances, the first 6 residues of the scaffold may be truncated. In certain embodiments, the SCF8 library includes five or more mutations from those mutations depicted in FIG. 5. In certain embodiments, the SCF8 library includes five or more mutations from those mutations depicted in FIGS. 31-32. In certain embodiments, the SCF8 library includes five or more mutations from those mutations depicted in FIGS. 33-34. In certain instances, the SCF8 library includes a mutation at position F10. In some cases, the F10 residue is mutated with a hydrophobic residue (e.g., Y, F, L and H).

In some embodiments, the library includes the scaffold SCF15, Symfoil 4P trimer (designed beta-trefoil). In certain embodiments, the SCF15 library includes five or more mutations from those mutations depicted in FIG. 6. In certain embodiments, the SCF15 library includes five or more mutations from those mutations depicted in FIGS. 31-32. In certain embodiments, the SCF15 library includes five or more mutations from those mutations depicted in FIGS. 33-34.

In some embodiments, the library includes the scaffold SCF23, EphA2 SAM domain. In certain embodiments, the SCF23 library includes five or more mutations from those mutations depicted in FIG. 7. In certain embodiments, the SCF23 library includes five or more mutations from those mutations depicted in FIGS. 31-32. In certain embodiments, the SCF23 library includes five or more mutations from those mutations depicted in FIGS. 33-34.

In some embodiments, the library includes the scaffold SCF24, GRIP domain of Golgin245. In certain embodiments, the SCF24 library includes five or more mutations from those mutations depicted in either FIG. 8 (e.g., SCF24-1) or FIG. 9 (e.g., SCF24-2). In certain embodiments, the SCF24-1 library includes five or more mutations from those mutations depicted in FIGS. 31-32. In certain embodiments, the SCF24-1 library includes five or more mutations from those mutations depicted in FIGS. 33-34. In certain embodiments, the SCF24-2 library includes five or more mutations from those mutations depicted in FIGS. 31-32. In certain embodiments, the SCF24-2 library includes five or more mutations from those mutations depicted in FIGS. 33-34.

In some embodiments, the library includes the scaffold SCF27, SpoOB-Helix hairpin domain. In certain embodiments, the SCF27 library includes five or more mutations from those mutations depicted in FIG. 10. In certain embodiments, the SCF27 library includes five or more mutations from those mutations depicted in FIGS. 31-32. In certain embodiments, the SCF27 library includes five or more mutations from those mutations depicted in FIGS. 33-34.

In some embodiments, the library includes the scaffold SCF28, C-terminal domain of Ku. In certain embodiments, the SCF28 library includes five or more mutations from those mutations depicted in FIG. 11. In certain embodiments, the SCF28 library includes five or more mutations from those mutations depicted in FIGS. 31-32. In certain embodiments, the SCF28 library includes five or more mutations from those mutations depicted in FIGS. 33-34.

In some embodiments, the library includes the scaffold SCF29, CUE domain of Cue2 protein. In certain embodiments, the SCF29 library includes five or more mutations from those mutations depicted in FIG. 12. In certain embodiments, the SCF29 library includes five or more mutations from those mutations depicted in FIGS. 31-32. In certain embodiments, the SCF29 library includes five or more mutations from those mutations depicted in FIGS. 33-34. In certain instances, the SCF29 library includes a mutation at position I10. In some cases, the I10 residue is mutated with hydrophobic residues (e.g., F, I, L and V).

In some embodiments, the library includes the scaffold SCF32, GA domain of protein G. In certain embodiments, the SCF32 library includes five or more mutations from those mutations depicted in FIG. 13. In certain embodiments, the SCF32 library includes five or more mutations from those mutations depicted in FIGS. 31-32. In certain embodiments, the SCF32 library includes five or more mutations from those mutations depicted in FIGS. 33-34.

Any of the libraries described in FIGS. 1-30 may be described as including one or more mutations at the numbered positions listed in Figure in 35 which correspond to the sequences of FIGS. 1-30. Each of the libraries may include mutations at a mixture of any five or more of the numbered positions listed in FIG. 35. For example, in certain instances, the SCF32 library includes five or more mutations at positions 25, 27, 28, 31, 34, 36, 37, 39, 40, 43 and 44. For example, in certain instances, the SCF32 library includes eight or more mutations at positions 25, 27, 28, 31, 34, 36, 37, 39, 40, 43 and 44. For example, in certain instances, the SCF32 library includes ten or more mutations at positions 25, 27, 28, 31, 34, 36, 37, 39, 40, 43 and 44. For example, in certain instances, the SCF32 library includes mutations at all of positions 25, 27, 28, 31, 34, 36, 37, 39, 40, 43, 44 and 47. In certain instances, the SCF32 library includes mutations at positions 25, 27, 28, 31 and 34. In certain instances, the SCF32 library includes mutations at positions 39, 40, 43, 44 and 47. In certain instances, the SCF32 library includes mutations at positions 31, 34, 36, 37 and 39.

In some embodiments, the library includes the scaffold SCF37, PEM-1 like protein. In certain embodiments, the SCF37 library includes five or more mutations from those mutations depicted in FIG. 14. In certain embodiments, the SCF37 library includes five or more mutations from those mutations depicted in FIGS. 31-32. In certain embodiments, the SCF37 library includes five or more mutations from those mutations depicted in FIGS. 33-34.

In some embodiments, the library includes the scaffold SCF38, Fasciculin-2. In certain embodiments, the SCF38 library includes five or more mutations from those mutations depicted in FIG. 15. In certain embodiments, the SCF38 library includes five or more mutations from those mutations depicted in FIGS. 31-32. In certain embodiments, the SCF38 library includes five or more mutations from those mutations depicted in FIGS. 33-34.

In some embodiments, the library includes the scaffold SCF40, Nucleotide exchange factor C-terminal domain. In certain embodiments, the SCF40 library includes five or more mutations from those mutations depicted in FIG. 16. In certain embodiments, the SCF40 library includes five or more mutations from those mutations depicted in FIGS. 31-32. In certain embodiments, the SCF40 library includes five or more mutations from those mutations depicted in FIGS. 33-34.

In some embodiments, the library includes the scaffold SCF42, Transcription antitermination protein NusG. In certain embodiments, the SCF42 library includes five or more mutations from those mutations depicted in FIG. 17. In certain embodiments, the SCF42 library includes five or more mutations from those mutations depicted in FIGS. 31-32. In certain embodiments, the SCF42 library includes five or more mutations from those mutations depicted in FIGS. 33-34. In certain instances, the SCF42 library includes a mutation at position F19. In some cases, the F19 residue is mutated with a hydrophobic residue (e.g., Y, F, L and H). In some cases, the F19 residue is mutated with a hydrophobic residue (e.g., Y and F).

In some embodiments, the library includes the scaffold SCF44, ThiS protein in complex with ThiF. In certain embodiments, the SCF44 library includes five or more mutations from those mutations depicted in FIG. 18. In certain embodiments, the SCF44 library includes five or more mutations from those mutations depicted in FIGS. 31-32. In certain embodiments, the SCF44 library includes five or more mutations from those mutations depicted in FIGS. 33-34.

In some embodiments, the library includes the scaffold SCF47, GYF domain of CD2bp2. In certain embodiments, the SCF47 library includes five or more mutations from those mutations depicted in FIG. 19. In certain embodiments, the SCF47 library includes five or more mutations from those mutations depicted in FIGS. 31-32. In certain embodiments, the SCF47 library includes five or more mutations from those mutations depicted in FIGS. 33-34.

In some embodiments, the library includes the scaffold SCF53, Rhodnin Kazal inhibitor. In certain embodiments, the SCF53 library includes five or more mutations from those mutations depicted in FIG. 20. In certain embodiments, the SCF53 library includes five or more mutations from those mutations depicted in FIGS. 31-32. In certain embodiments, the SCF53 library includes five or more mutations from those mutations depicted in FIGS. 33-34.

In some embodiments, the library includes the scaffold SCF55, Anti-TRAP. In certain embodiments, the SCF55 library includes five or more mutations from those mutations depicted in FIG. 21. In certain embodiments, the SCF55 library includes five or more mutations from those mutations depicted in FIGS. 31-32. In certain embodiments, the SCF55 library includes five or more mutations from those mutations depicted in FIGS. 33-34.

In some embodiments, the library includes the scaffold SCF56, TNF Receptor 17 (BCMA). In certain embodiments, the SCF56 library includes five or more mutations from those mutations depicted in FIG. 22 (e.g., sub-library 1) or FIG. 23 (e.g., sub-library 2). In certain embodiments, the SCF56 library is SCF56-1 and includes five or more mutations from those mutations depicted in FIGS. 31-32. In certain embodiments, the SCF56 library is SCF56-1 and includes five or more mutations from those mutations depicted in FIGS. 33-34. In certain embodiments, the SCF56 library is SCF56-2 and includes five or more mutations from those mutations depicted in FIGS. 31-32. In certain embodiments, the SCF56 library is SCF56-2 and includes five or more mutations from those mutations depicted in FIGS. 33-34. In certain instances, the SCF56-1 library includes one or more (e.g., 1 or 2) mutations selected from positions Y6 and I15. In some cases, the Y6 and/or I15 residues are mutated to include a hydrophobic residue (e.g., F, I, L or V).

In some embodiments, the library includes the scaffold SCF63, Fyn SH3 domain (Fynomers). In certain embodiments, the SCF63 library includes five or more mutations from those mutations depicted in FIG. 24. In certain embodiments, the SCF63 library includes five or more mutations from those mutations depicted in FIGS. 31-32. In certain embodiments, the SCF63 library includes five or more mutations from those mutations depicted in FIGS. 33-34.

In some embodiments, the library includes the scaffold SCF64, E3 ubiquitin-protein ligase UBR5. In certain embodiments, the SCF64 library includes five or more mutations from those mutations depicted in FIG. 25. In certain embodiments, the SCF64 library includes five or more mutations from those mutations depicted in FIGS. 31-32. In certain embodiments, the SCF64 library includes five or more mutations from those mutations depicted in FIGS. 33-34.

In some embodiments, the library includes the scaffold SCF65, DNA repair endonuclease XPF. In certain embodiments, the SCF65 library includes five or more mutations from those mutations depicted in FIG. 26. In certain embodiments, the SCF65 library includes five or more mutations from those mutations depicted in FIGS. 31-32. In certain embodiments, the SCF65 library includes five or more mutations from those mutations depicted in FIGS. 33-34. In certain instances, the SCF65 library includes one or more (e.g., 1 or 2) mutations selected from positions M9 and I55. In some cases, the M9 and/or I55 residues are mutated to include a hydrophobic residue (e.g., F, I, L, M or V). In some cases, the M9 residue is mutated to include F, I, L and M. In some cases, the I55 residue is mutated to include F, I, L and V.

In some embodiments, the library includes the scaffold SCF66, Rad23 homologue B, xpcb domain. In certain embodiments, the SCF66 library includes five or more mutations from those mutations depicted in FIG. 27. In certain embodiments, the SCF66 library includes five or more mutations from those mutations depicted in FIGS. 31-32. In certain embodiments, the SCF66 library includes five or more mutations from those mutations depicted in FIGS. 33-34. In certain instances, the SCF56-1 library includes a mutation at positions M16. In some cases, the M16 residue is mutated to include a hydrophobic residue (e.g., F, I, L and M).

In some embodiments, the library includes the scaffold SCF70, LEM domain of emerin. In certain embodiments, the SCF70 library includes five or more mutations from those mutations depicted in FIG. 28. In certain embodiments, the SCF70 library includes five or more mutations from those mutations depicted in FIGS. 31-32. In certain embodiments, the SCF70 library includes five or more mutations from those mutations depicted in FIGS. 33-34.

In some embodiments, the library includes the scaffold SCF75, GspC. In certain embodiments, the SCF75 library includes five or more mutations from those mutations depicted in FIG. 29. In certain embodiments, the SCF75 library includes five or more mutations from those mutations depicted in FIGS. 31-32. In certain embodiments, the SCF75 library includes five or more mutations from those mutations depicted in FIGS. 33-34.

In some embodiments, the library includes the scaffold SCF95, Protein Z. In certain embodiments, the SCF95 library includes five or more mutations from those mutations depicted in FIG. 30. In certain embodiments, the SCF95 library includes five or more mutations from those mutations depicted in FIGS. 31-32. In certain embodiments, the SCF95 library includes five or more mutations from those mutations depicted in FIGS. 33-34.

For any of the libraries described above and depicted in FIGS. 1-30, the library of interest may include 6 or more of the mutations depicted in the figure. For any of the libraries described above and depicted in FIGS. 1-30, the library of interest may include 7 or more of the mutations depicted in the figure. For any of the libraries described above and depicted in FIGS. 1-30, the library of interest may include 8 or more of the mutations depicted in the figure. For any of the libraries described above and depicted in FIGS. 1-30, the library of interest may include 9 or more of the mutations depicted in the figure. For any of the libraries described above and depicted in FIGS. 1-30, the library of interest may include 10 or more of the mutations depicted in the figure. For any of the libraries described above and depicted in FIGS. 1-30, the library of interest may include 11 or more of the mutations depicted in the figure. For any of the libraries described above and depicted in FIGS. 1-30, the library of interest may include 12 or more of the mutations depicted in the figure. For any of the libraries described above and depicted in FIGS. 1-30, the library of interest may include all of the mutations depicted in the figure. FIG. 35 includes a compiled list of mutation position numbers of interest corresponding to the libraries of FIGS. 1-30.

The diversity of the subject libraries is designed to maximize diversity while minimizing structural perturbations of the scaffold domain of interest. The positions to be mutated are selected to ensure that the peptidic compounds of the subject libraries can maintain a folded state under physiological conditions. Another aspect of generating diversity in the subject libraries is the selection of amino acid positions to be mutated such that the amino acids can form a potential binding surface in the scaffold domain, whether or not the residues actually contact a target protein. Any convenient method may be used to determine whether an amino acid position is part of a potential binding surface.

The mutations may be found at positions in the scaffold domain of interest where the amino acid residue is at least in part solvent exposed. Solvent exposed positions can be determined using software suitable for protein modeling and three-dimensional structural information obtained from a crystal structure. The mutations of the scaffold domain of interest may be concentrated at one of several different potential binding surfaces of the scaffold domain. In some instances, the majority of the mutations are at non-core positions of the scaffold domain of interest (e.g., solvent exposed or boundary positions) however in some cases one or more mutations may be located at hydrophobic core positions. In certain embodiments, mutations at hydrophobic core positions may be tolerated without significantly disrupting the scaffold structural motif or scaffold structure.

In certain embodiments, mutations at boundary positions may also be tolerated without significantly disrupting the scaffold structure of interest. Mutations at such positions may confer desirable properties upon the resulting peptidic compound variants, such as stability, a certain structural property, or specific binding to a target molecule.

The positions of the mutations in the scaffold domains of interest may be described herein either by reference to a structural motif or region, or by reference to a position number in the primary sequence of the scaffold domain. FIGS. 1-34 illustrate the alignment of position numbering schemes for the scaffold domains relative to the mutations of certain libraries of the invention. Suitable alternate scaffold domain sequences may be substituted for an existing scaffold sequence from within a family of proteins using any convenient sequence alignment methods, and the positions of the mutations that define a subject library may be transferred from one scaffold to another. Alignment methods based on structural motifs such as beta-strands and alpha-helices may also be used to place an alternative scaffold domain sequence within the framework of the position numbering scheme of one of the scaffolds of interest depicted in FIGS. 1-34.

Another aspect of the diversity of the subject libraries is the size of the library, i.e., the number of distinct compounds of the library. In some embodiments, a subject library includes 5 or more distinct compounds (e.g., of differing amino acid sequence), such as 10 or more, 20 or more, 50 or more, 100 or more, 300 or more, $1 \times 10^3$ or more, $1 \times 10^4$ or more, $1 \times 10^5$ or more, $1 \times 10^6$ or more, $1 \times 10^7$ or more, $1 \times 10^8$ or more, $1 \times 10^9$ or more, $1 \times 10^{10}$ or more, $1 \times 10^{11}$ or more, or $1 \times 10^{12}$ or more, distinct compounds. In certain embodiments, the subject library includes about 50 to about $1 \times 10^5$ distinct compounds, such as about 50 to about $1 \times 10^4$, about 50 to about $1 \times 10^3$, about 50 to about 300 distinct compounds. In certain embodiments, the subject library includes about $1 \times 10^3$ to about $1 \times 10^{12}$ distinct compounds, such as about $1 \times 10^4$ to about $1 \times 10^{12}$, about $1 \times 10^5$ to about $1 \times 10^{12}$, about $1 \times 10^6$ to about $1 \times 10^{12}$, about $1 \times 10^7$ to about $1 \times 10^{12}$, about $1 \times 10^8$ to about $1 \times 10^{12}$, about $1 \times 10^9$ to about $1 \times 10^{12}$, about $1 \times 10^{10}$ to about $1 \times 10^{12}$ distinct compounds. In certain embodiments, the subject library is a phage display library having a theoretical diversity of $1 \times 10^3$ to $1 \times 10^{12}$ distinct compounds.

The peptidic sequences of the compounds of the subject libraries may be any of any convenient length. The length of the peptidic sequences may be defined by the length of the scaffold domain itself (e.g., the minimum consensus sequence that encompasses the structural motif of the scaffold), even if the core peptidic sequence of the compounds of the library are part of a larger sequence (e.g., in a fusion with a phage coat protein or conjugated to a N- or C-terminal peptidic tag). In some embodiments, each compound of the subject library includes a peptidic sequence of between 25 and 150 residues, such as between, 25 and 120 residues, 25 and 100 residues, 25 and 90 residues, 25 and 80 residues, 25 and 70 residues, 25 and 60 residues, 25 and 50 residues, 30 and 120 residues, 30 and 100 residues, 30 and 90 residues, 30 and 80 residues, 30 and 70 residues, 30 and 60 residues, 30 and 50 residues, 50 and 150 residues, 50 and 120 residues, 50 and 100 residues, 50 and 90 residues, 50 and 80 residues, 40 and 70 residues, 40 and 60 residues, 60 and 100 residues, 70 and 100 residues, 100 and 150 residues. It is understood that the number of residues comprised in each member of a subject library may vary according to the underlying scaffold, extension sequences, mutations included, etc.

In certain embodiments, each compound of the subject library includes a scaffold domain and a variable domain. The variable domain may be a part of the scaffold domain and may be either a continuous or a discontinuous sequence of residues. A variable domain that is defined by a discontinuous sequence of residues may include contiguous variant amino acids at positions that are arranged close in space relative to each other in the structure of the compound. The variable domain may form a potential binding interface of the compounds. The variable domain may define a binding surface area of a suitable size for forming protein-protein interactions. The variable domain may include a surface area of between 500 and 1800 Å$^2$, such as between about 500 and about 1600 Å$^2$, between about 500 and about 1400 Å$^2$, between about 500 and about 1200 Å$^2$, between about 500 and about 1000 Å$^2$, between about 500 and about 800 Å$^2$, between about 500 and about 700 Å$^2$, between about 600 and about 1600 Å$^2$, between about 600 and about 1400 Å$^2$, between about 600 and about 1200 Å$^2$, between about 600 and about 1000 Å$^2$, between about 600 and about 800 Å$^2$, between about 800 and about 1600 Å$^2$, between about 800 and about 1400 Å$^2$, between about 800 and about 1200 Å$^2$, between about 800 and about 1000 Å$^2$, between about 1000 and about 1600 Å$^2$, between about 1000 and about 1400 Å$^2$, between about 1000 and about 1200 Å$^2$. It is understood that the surface area of the variable domain varies depending on a variety of factors, e.g., the scaffold selected, the protein-protein interaction face, the number of mutations, etc. In some embodiments, the members of a library include five or more different mutations (e.g., core or non-core mutations, as described herein) located in a protein-protein interaction region of the scaffold domain.

In some instances, the library includes a variable domain located at the protein-protein interaction region that comprises a surface area of about 500 to about 1800 Å$^2$.

The individual sequences of the members of any one of the subject libraries can be determined as follows. Any scaffold as described herein (e.g., a scaffold of FIGS. 1-34) may be selected as a scaffold for a subject library. The positions of the mutations in the scaffold domain of interest may be selected as described herein, e.g., as depicted in FIGS. 1-34. The nature of the mutation at each variant amino acid position may be selected, e.g., substitution with any naturally occurring amino acid, or substitution with a limited number of representative amino acids that provide a reasonable diversity of physiochemical properties (e.g., hydrophobicity, hydrophilicity, size, solubility). Certain variant amino acid positions may be selected as positions where mutations can include the insertion or deletion of amino acids, e.g., the insertion of 1 or 2 amino acids where the variant amino acid position occurs in a loop or turn region of the scaffold. In certain embodiments, the mutations can include the insertion of amino acids at one or more positions (e.g., as described by mutations in FIGS. 1-34). After selection of the scaffold, selection of the positions of variant amino acids, and selection of the nature of the mutations at each position, the individual sequences of the members of the library can be determined.

In some embodiments, two or more, such as 3 or more, 4 or more, 5 or more, 10 or more, 20 or more, up to all of the subject libraries may be combined to produce a larger library. Any two or more convenient scaffolded libraries may be selected for inclusion in a combination library.

In some embodiments, the subject library is bifunctional in the sense that the peptidic compounds of the library have two potential binding surfaces. Such libraries can be screened to identify compounds having specific binding properties for two target molecules. In certain embodiments, the compounds may include a first potential binding surface for a first target molecule and a second potential binding surface for a second target molecule. In certain embodiments, the second potential binding surface is an inherent binding surface of the scaffold for a second target molecule. Variant amino acids may be introduced at locations on the second potential binding surface of the scaffold (e.g., using methods described herein) to screen for a desired binding property to a second target molecule. In certain embodiments, the first target molecule is a therapeutic target protein and the second target molecule is an endogenous protein or receptor (e.g., an IgG, FcRn, or serum albumin protein) that is capable of modulating the pharmacokinetic properties (e.g., in vivo half-life) of a peptidic compound upon recruitment. In some embodiments, any convenient endogenous protein target may be selected as one of the targets to be screened. In certain embodiments, the compounds of the library include two potential binding surfaces for the same target molecule, where the overall binding affinity of the compound may be modulated via an avidity effect.

In some embodiments, the inherent binding properties of the scaffold domain of interest are utilized to provide one potential binding surface of the subject bifunctional libraries. In certain embodiments, the bifunctional library includes compounds having a second binding surface that specifically binds an endogenous human protein.

Any suitable combinations of potential binding surfaces may be utilized to produce the subject bifunctional libraries. In some cases, the two potential binding surfaces of a bifunctional library are selected to minimize any potential steric interactions between the first and second target molecules, e.g., by binding the targets on opposite sides of the scaffold. The subject bifunctional library may include one or more variable domains on each of the potential binding surfaces of the library. In some embodiments, the subject bifunctional library includes 3 or more mutations, such as 4 or more, 5 or more, 6 or more, 7 or more, 8 or more, 10 or more, 12 or more or 14 or more mutations in the variable domain of a first surface, and 3 or more mutations, such as 4 or more, 5 or more, 6 or more, 7 or more, 8 or more, 10 or more, 12 or more or 14 or more mutations in the variable domain of a second surface. Any suitable mutations in the variable domains may be selected.

The subject bifunctional library may be screened for specific binding to first and second target molecules using a variety of strategies. For example, the libraries can be screened for binding to first and second target molecules using simultaneous screening, consecutive screening or convergent screening strategies. In some embodiments, the bifunctional library is screened for simultaneous binding of first and second targets to first and second surfaces, respectively. In some embodiments, a first library is screened for binding of a first target to a first surface to produce a second generation library based on a scaffold that binds the first target. In certain embodiments, such binding of a first target protein to a first surface is inherent in the scaffold, and does not require screening, although affinity maturation optimization of the binding of the first target may be performed. The second generation library based on the scaffold that binds the first target is then screened for binding to a second target at a second surface. In some embodiments, a convergent screening strategy is utilized where a first library is screened for binding to a first target and a second library is screened for binding to a second target. Utilizing the results of these screens, first and second binding surfaces are then incorporated into the same scaffold to produce bifunctional peptidic compounds. Such bifunctional compounds and libraries can be optimized by affinity maturation.

Also provided are affinity maturation libraries, e.g., second generation scaffolded peptidic libraries based on a parent peptidic compound that binds to a certain target molecule, where the libraries can be screened to optimize for binding affinity and specificity, or any desirable property, such as, protein folding, protease stability, thermostability, compatibility with a pharmaceutical formulation, etc.

In some embodiments, the affinity maturation library is a phage display library that may be screened for binding to a D-target or an L-target protein. In other embodiments, the affinity maturation library is a D-peptidic library of chemically synthesized compounds. Such D-peptidic libraries may be screened for binding to a L-target protein. In certain embodiments, the D-peptidic library has a scaffold domain corresponding to the sequence of a L-peptidic compound that is identified from screening a L-peptidic phage display library for binding to a D-target protein.

In some embodiments, the affinity maturation library is a scaffolded peptidic library as described herein, except that a fraction of the variant amino acid positions are held as fixed positions while the remaining variant amino acid positions define the new library. The mutations of these variant amino acids that define the affinity maturation library may include substitution with all 20 naturally occurring amino acids. The variant amino acids that are held as fixed become part of a new scaffold domain. In certain embodiments, the affinity maturation library is a scaffolded peptidic library described herein, where 70% or more of the variant amino acids, such as 75% or more, 80% or more, or 85% or more are held fixed. In certain embodiments, the affinity maturation library is a scaffolded peptidic library described herein, where 8 or more of the variant amino acids, such as 9 or more, 10 or more, or 11 or more, or 12 or more are held fixed. In some cases, the affinity maturation library includes 6 or less, such as 5 or less, 4 or less, or 3 or less variant amino acids. In certain embodiments, the affinity maturation library includes 4 remaining variant amino acids. In certain embodiments, the remaining variant amino acids are contiguous. In certain embodiments, the remaining variant amino acids form a continuous sequence of residues in the scaffold domain of interest. In certain embodiments, the affinity maturation library is based on one of the scaffolded peptidic libraries as described in FIGS. 1-34, where a fraction of the variant amino acid positions are held as fixed positions while the remaining variant amino acid positions define the new library.

In some instances, a peptidic compound that is identified after initial screening of a subject scaffolded peptidic library for binding to a certain target molecule may be selected as a scaffold for an affinity maturation library. Any convenient methods of affinity maturation may be used. In some cases, a number of affinity maturation libraries are prepared that include mutations at limited subsets of possible variant positions (e.g., mutations at 4 of the 12 or more variable positions), while the rest of the variant positions are held as fixed positions. The positions of the mutations may be tiled through the scaffold sequence to produce a series of libraries such that mutations at every variant position is represented and a diverse range of amino acids are substituted at every position (e.g., all 20 naturally occurring amino acids). Mutations that include deletion or insertion of one or more amino acids may also be included at variant positions of the affinity maturation libraries. An affinity maturation library may be prepared and screened using any convenient method, e.g., phage display library screening, to identify members of the library having an improved property, e.g., increased binding affinity for a target molecule, protein folding, protease stability, thermostability, compatibility with a pharmaceutical formulation, etc.

In some embodiments, in an affinity maturation library, most or all of the variant amino acid positions in the variable regions of the parent peptidic compound are held as fixed positions, and contiguous mutations are introduced at positions adjacent to these variable regions. Such mutations may be introduced at positions in the parent peptidic compound that were previously considered fixed positions in the original parent scaffold domain. Such mutations may be used to optimize the peptidic compound variants for any desirable property, such as protein folding, protease stability, thermostability, compatibility with a pharmaceutical formulation, etc.

Fusion polypeptides including peptidic compounds of interest can be displayed on the surface of a cell or virus in a variety of formats and multivalent forms. In one embodiment, a bivalent moiety, for example, a hinge and dimerization sequence from a Fab template, an anti-MBP (maltose binding protein) Fab scaffold is used for displaying peptidic compound variants on the surface of a phage particle. Optionally, other sequences encoding polypeptide tags useful for purification or detection such as a FLAG tag, can be fused at the 3' end of the nucleic acid sequence encoding the peptidic compound of interest.

Polynucleotide Libraries

Also provided is a library of polynucleotides that encodes a library of peptidic compounds as described above. In some embodiments, each polynucleotide of the library encodes a distinct peptidic compound that includes three or more, such as four or more or five or more mutations at non-core positions in a region of the scaffold domain.

In some embodiments, each polynucleotide of the library encodes a peptidic compound that includes 20 or more, such as 30 or more, 40 or more, or 50 or more, 60 or more, 70 or more, 80 or more, 90 or more, or even 100 or more amino acids. In some embodiments, each polynucleotide of the library encodes a peptidic compound that includes 150 or less, such as 120 or less, 100 or less, 80 or less 60 or less, 50 or less, 40 or less amino acid residues. In certain embodiments, each polynucleotide of the library encodes a peptidic compound that includes 20-150 amino acid residues, such as 20-40, 20-50, 30-60, 40-60, 40-50, 50-60, 60-90, 60-100, or 100-150 amino acids. It is understood that the number of residues comprised in each member of a subject library may vary according to the underlying scaffold, extension sequences, mutations included, etc. In some embodiments, each polynucleotide of the library encodes a peptidic compound where the compound includes three or more variant amino acids at non-core positions, and where each variant amino acid is encoded by a random codon. In certain embodiments, the random codon is selected from the group consisting of B1(HT) (e.g., as described herein), WTK (e.g., as described herein), NTT (e.g., as described herein), TWT (e.g., as described herein), NNK (where N=A, G, C and T, and K=G and T) and KHT (where K=G and T, and H=A, C and T).

In certain embodiments, the subject library of polynucleotides is a library of replicable expression vectors that includes a nucleic acid sequence encoding a gene fusion, where the gene fusion encodes a fusion protein including the peptidic compound of interest fused to all or a portion of a viral coat protein. Also included is a library of diverse replicable expression vectors comprising a plurality of gene fusions encoding a plurality of different fusion proteins including a plurality of the variable domains generated with diverse sequences as described above. The vectors can include a variety of components and can be constructed to allow for movement of the scaffold domain of interest between different vectors and/or to provide for display of the fusion proteins in different formats. Examples of vectors include phage vectors and ribosome display vectors. The phage vector has a phage origin of replication allowing phage replication and phage particle formation. In certain embodiments, the phage is a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Any convenient display methods may be used to display peptidic compounds encoded by the subject library of polynucleotides, such as cell-based display techniques and cell-free display techniques. In certain embodiments, cell-based display techniques include phage display, bacterial display, yeast display and mammalian cell display. In certain embodiments, cell-free display techniques include mRNA display and ribosome display.

In certain embodiments, the library of polynucleotides is a library that encodes 50 or more distinct peptidic compounds, such as 100 or more, 300 or more, $1 \times 10^3$ or more, $1 \times 10^4$ or more, $1 \times 10^5$ or more, $1 \times 10^6$ or more, $1 \times 10^7$ or more, 1×10⁸ or more, 1×10⁹ or more, 1×10¹⁰ or more, 1×10¹¹ or more, or 1×10¹² or more, distinct compounds, where each polynucleotide of the library encodes a peptide compound of interest that comprises three or more, such as four or more or five or more different non-core mutations. In certain embodiments, the library of polynucleotides is a library of replicable expression vectors.

In some embodiments, each polynucleotide of the library encodes a peptidic compound comprising five or more (e.g., 5, 6, 7, 8, 9, 10, 11, 12, 13, 14, 15, 16, 17 or 18) variant amino acids at non-core positions, wherein each variant amino acid is encoded by a random codon. In certain embodiments, the random codon is selected from the group consisting of (B1)HT, WTK, NNT, TWT, NNK and KHT. In some cases, the codon is (B1)HT.

Phage Display Libraries

The subject libraries may be prepared using any convenient methods, such as, methods that find use in the preparation of libraries of peptidic compounds, for example, phage display methods.

In some embodiments, the subject library is a phage display library. A utility of phage display is that large libraries of randomized protein variants can be rapidly and efficiently sorted for those sequences that bind to a target protein. Display of polypeptide libraries on phage may be used for screening for polypeptides with specific binding properties. Polyvalent phage display methods may be used for displaying polypeptides through fusions to either gene III or gene VIII of filamentous phage. Wells and Lowman (1992) Curr. Opin. Struct. Biol B:355-362 and references cited therein. In monovalent phage display, a polypeptide library is fused to a gene III or a portion thereof and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) Methods: A companion to Methods in Enzymology 3:205-216. In phage display, the phenotype of the phage particle, including the displayed polypeptide, corresponds to the genotype inside the phage particle, the DNA enclosed by the phage coat proteins.

In some embodiments, each peptidic compound of a subject library of interest is fused to at least a portion of a viral coat protein. Examples of viral coat proteins include infectivity protein PIII, major coat protein PVIII, p3, Soc, Hoc, gpD (of bacteriophage lambda), minor bacteriophage coat protein 6 (pVI) (filamentous phage; J. Immunol. Methods, 1999, 231(1-2):39-51), variants of the M13 bacteriophage major coat protein (P8) (Protein Sci 2000 Apr.; 9(4):647-54). The fusion protein can be displayed on the surface of a phage and suitable phage systems include M13KO7 helper phage, M13R408, M13-VCS, and Phi X 174, pJuFo phage system (J. Virol. 2001 August; 75(15): 7107-13), hyperphage (Nat. Biotechnol. 2001 Jan.; 19(1): 75-8). In certain embodiments, the helper phage is M13KO7, and the coat protein is the M13 Phage gene III coat protein. In certain embodiments, the host is E. coli or protease deficient strains of E. coli. Vectors, such as the fth1 vector (Nucleic Acids Res. 2001 May 15; 29(10):E50-0) can be useful for the expression of the fusion protein.

Display of Fusion Polypeptides

Any convenient methods for displaying fusion polypeptides including scaffolded peptidic compounds on the surface of bacteriophage may be used. For example methods as described in patent publication number WO 92/01047; WO 92/20791; WO 93/06213; WO 93/11236 and WO 93/19172.

The expression vector also can have a secretory signal sequence fused to the DNA encoding each scaffolded peptidic compound. This sequence may be located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:1931 (1983), MalE, PhoA and other genes. A prokaryotic signal sequence for practicing this invention is the E. coli heat-stable enterotoxin II (STII) signal sequence as described by Chang et al., Gene 55:189 (1987), and malE. In some cases, secretion signals for the fusion proteins may be achieved via either the StII signal sequence (secB pathway) or the TorA signal sequence (TAT pathway) (see, e.g., Muller et al. "Efficient phage display of intracellularly folded proteins mediated by the TAT pathway," Protein Engineering, Design & Selection vol. 24 no. 6 pp. 473-484, 2011).

The vector may also include a promoter to drive expression of the fusion protein. Promoters most commonly used in prokaryotic vectors include the lac Z promoter system, the alkaline phosphatase pho A promoter, the bacteriophage .gamma.-$_{PL}$ promoter (a temperature sensitive promoter), the tac promoter (a hybrid trp-lac promoter that is regulated by the lac repressor), the tryptophan promoter, and the bacteriophage T7 promoter. While these are the most commonly used promoters, other suitable microbial promoters may be used as well.

The vector can also include other nucleic acid sequences, for example, sequences encoding gD tags, c-Myc epitopes, FLAG tags, poly-histidine tags, fluorescent proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is fused to a scaffolded peptidic compound which is not fused to the viral coat protein. Nucleic acid sequences encoding, for example, a polyhistidine tag, are useful for identifying fusion proteins including peptidic compounds of interest that bind to a specific target using immunohistochemistry. Tags useful for detection of target binding can be fused to either a peptidic compound of interest not fused to a viral coat protein or a peptidic compound of interest fused to a viral coat protein.

Another useful component of the vectors used to practice this invention are phenotypic selection genes. The phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving peptidic compounds and libraries of interest between different vectors and expression systems. The suppressible stop codons are useful to control the level of expression of the fusion protein and to facilitate purification of peptidic compounds of interest. For example, an amber stop codon can be read as Gln in a supE host to enable phage display, while in a non-supE host it is read as a stop codon to produce soluble peptidic compounds of interest without fusion to phage coat proteins. These synthetic sequences can be fused to peptidic compounds of interest in the vector.

In some cases, vector systems that allow the nucleic acid encoding a peptidic compound of interest to be easily removed from the vector system and placed into another vector system, may be used. For example, appropriate restriction sites can be engineered in a vector system to facilitate the removal of the nucleic acid sequence encoding the peptidic compounds of interest. The restriction sequences are usually chosen to be unique in the vectors to facilitate efficient excision and ligation into new vectors. Peptidic compound domains of interest can then be expressed from vectors without extraneous fusion sequences, such as viral coat proteins or other sequence tags.

Between nucleic acid encoding peptidic compounds of interest (gene 1) and the viral coat protein (gene 2), DNA encoding a termination codon may be inserted, such termination codons including UAG (amber), UAA (ocher) and UGA (opel). (Microbiology, Davis et al., Harper & Row, New York, 1980, pp. 237, 245-47 and 374). The termination codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as E. coli suppressor strain (Bullock et al., BioTechniques 5:376-379 (1987)). Any acceptable method may be used to place such a termination codon into the mRNA encoding the fusion polypeptide.

The suppressible codon may be inserted between the first gene encoding the peptidic compounds of interest, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the peptidic compound domain of interest is synthesized substantially without fusion to the phage coat protein due to termination at the inserted suppressible triplet UAG, UAA, or UGA. In the non-suppressor cell the peptidic compound domain of interest is synthesized and secreted from the host cell due to the absence of the fused phage coat protein which otherwise anchored it to the host membrane.

Methods of Screening

Also provided are methods of screening scaffolded peptidic libraries of compounds, e.g., as described above, for binding to a target protein. In addition, the libraries may be selected for improved binding affinity to a certain target protein, e.g., as described above, for the preparation and screening of affinity maturation libraries. The target proteins may include any type of protein of interest in research or therapeutic applications. Aspects of these screening methods may include determining whether a compound of the subject libraries specifically binds to a target protein of interest. Screening methods may include screening for inhibition of a biological activity. Such methods may include: (i) contacting a sample containing a target protein with a library of the invention; and (ii) determining whether a compound of the library specifically binds to the target protein.

The determining step may be carried out by any one or more of a variety a protocols for characterizing the specific binding or the inhibition of binding.

For example, screening may be a cell-based assay, an enzyme assay, a ELISA assay or other related biological assay for assessing specific binding or the inhibition of binding, and the determining or assessment step suitable for application in such assays are well known and involve routine protocols.

Screening may also include in silico methods, in which one or more physical and/or chemical attributes of compounds of the library of interest are expressed in a computer-readable format and evaluated by any one or more of a variety of molecular modeling and/or analysis programs and algorithms suitable for this purpose. In some embodiments, the in silico method includes inputting one or more parameters related to the target protein (e.g., a D- or an L-target protein), such as but not limited to, the three-dimensional coordinates of a known X-ray crystal structure of the target protein. In some embodiments, the in silico method includes inputting one or more parameters related to the compounds of the peptidic library, such as but not limited to, the three-dimensional coordinates of a known X-ray crystal structure of a parent scaffold domain of the library. In some instances, the in silico method includes generating one or more parameters for each compound in a peptidic library in a computer readable format, and evaluating the capabilities of the compounds to specifically bind to the target protein. The in silico methods include, but are not limited to, molecular modelling studies, biomolecular docking experiments, and virtual representations of molecular structures and/or processes, such as molecular interactions. The in silico methods may be performed as a pre-screen (e.g., prior to preparing a L-peptidic library and performing in vitro screening), or as a validation of binding compounds identified after in vitro screening.

Thus the screening methods of the invention can be carried out in vitro or in vivo. For example, when the compound is in a cell, the cell may be in vitro or in vivo, and the determining of whether the compound is capable of specifically binding to a target protein in the cell includes: (i) contacting the cell with a library of the invention; and (ii) assessing whether a compound of the library specifically binds to the target protein.

As such, determining whether a peptidic compound of a subject library of interest is capable of specifically binding a target protein may be carried out by any number of methods, as well as combinations thereof.

In some embodiments, the subject method includes:

(a) contacting a target protein with a scaffolded library of distinct peptidic compounds, where each compound of the library comprises a distinct variable domain and a peptidic scaffold domain, wherein the peptidic scaffold domain is selected from the group consisting of: DiGeorge syndrome critical region 8 (DGCR8) dimerization domain; Get5 C-terminal domain; H-NS domain from E. coli; KorB c-terminal dimerization domain; Lsr2 dimerization domain; PKA-RI alpa dimerization/docking domain (bovine); UBA domain of p62; N-terminal domain of SpoVT; Collagen XI trimerization domain; Symfoil 4P trimer (designed beta-trefoil); C-terminal domain of RNA polymerase alpha subunit; EphA2 SAM domain; GRIP domain of Golgin245; SpoOB-Helix hairpin domain; C-terminal domain of Ku; CUE domain of Cue2 protein; DNA helicase RuvA domain; GA domain of protein G; Hirustasin; Thrombomodulin (EGF type domains); Coagulation factor VIIa; PEM-1 like protein; Fasciculin-2; CD46 extracellular domain; Nucleotide exchange factor C-terminal domain; Tudor domain of TDRD3; Transcription antitermination protein NusG; CCL2 chemokine; ThiS protein in complex with ThiF; Chymotrypsin inhibitor; Carboxypeptidase inhibitor; GYF domain of CD2bp2; Cdk regulatory subunit1; CN2 toxin; CHD4-PHD finger domain; GATA type zinc finger; Leech derived tryptase inhibitor; Rhodnin Kazal inhibitor; MHC ClassII p41 fragment; Anti-TRAP; TNF Receptor17 (BCMA); NZF zinc-finger domain; Amaranth alpha amylase inhibitor; Sac7d (Nanofitins); APPI Kunitz domain; Fyn SH3 domain (Fynomers); E3 ubiquitin-protein ligase UBR5; DNA repair endonuclease XPF; Chain B:rad23 hom.B, xpcb domain; Chain B:dsk2-uba domain; Chain C:LEM domain/emerin; Chain A:Protein YBL047C UBA domain; Chains A/B: PKA docking/dimerization domain; Chain C: GspC; Chain A: Phage IF1 attachment protein G3P; Chain A: cd2ap sh3; Chain B: micronemal protein 6, EGF-like domain; Chain B: colicin-A; Chain B: Rubredoxin 2; Chain E: EGF domain of LDLR; Chain I: engineered protease inhibitor, SGPI scaffold; Chain B: engineered hck sh3; N-terminal fragment: NTL9; Brazzein; Insulin growth factor binding protein (IGFBP); Turkey ovomucoid, third domain (OMTKY3); Viscotoxin A1; Chromobox protein homolog 5; Protein Z; and Villin headpiece subdomain; and (b) identifying a compound of the library that specifically binds to the target protein.

In some embodiments, in the subject method, the target protein is a D-protein. In some embodiments, in the subject method, the target protein is a L-protein.

Phage Display Screening Methods

Screening for the ability of a fusion polypeptide including a peptidic compound of a subject library of interest to bind a target molecule can also be performed in solution phase. For example, a target protein can be attached with a detectable moiety, such as biotin. Phage that bind to the target molecule in solution can be separated from unbound phage by a molecule that binds to the detectable moiety, such as streptavidin-coated beads where biotin is the detectable moiety. Affinity of binders (e.g., peptidic compound fusions that bind to target protein) can be determined based on concentration of the target protein used, using any convenient formulas and criteria.

In some embodiments, the target protein may be attached to a suitable matrix such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by any convenient methods, e.g., methods as described in Methods in Enzymology, 44 (1976). After attachment of the target protein to the matrix, the immobilized target is contacted with the library expressing the peptidic compound of interest containing fusion polypeptides under conditions suitable for binding of at least a portion of the phage particles with the immobilized target. In some instances, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the higher affinity binders. Binders may be dissociated from the immobilized target by a variety of methods. These methods include competitive dissociation using the wild-type ligand, altering pH and/or ionic strength, and methods known in the art. Selection of binders may involve elution from an affinity matrix with a ligand. Elution with increasing concentrations of ligand should elute displayed binding peptidic compounds of increasing affinity.

The binders can be isolated and then reamplified or expressed in a host cell and subjected to another round of selection for binding of target molecules. Any number of rounds of selection or sorting can be utilized. One of the selection or sorting procedures can involve isolating binders that bind to an antibody to a polypeptide tag such as antibodies to the gD protein, FLAG or polyhistidine tags. Another selection or sorting procedure can involve multiple rounds of sorting for stability, such as binding to a target protein that specifically binds to folded peptidic compound of interest containing polypeptide and does not bind to unfolded polypeptide followed by selecting or sorting the stable binders for binding to a target protein.

In some cases, suitable host cells are transfected with genes encoding the binders and helper phage, and the host cells are cultured under conditions suitable for amplification of the phagemid particles. The phagemid particles are then collected and the selection process is repeated one or more times until binders having the desired affinity for the target molecule are selected. In certain embodiments, two or more rounds of selection are conducted.

After binders are identified by binding to the target protein, the nucleic acid can be extracted. Extracted DNA can then be used directly to transform E. coli host cells or alternatively, the encoding sequences can be amplified, for example using PCR with suitable primers, and then inserted into a vector for expression.

Any convenient strategy may be used to select for high affinity binders to a target protein. In certain embodiments, the process of screening is carried out by automated systems to allow for high-throughput screening of library candidates.

In certain embodiments, compounds of the subject peptidic library specifically bind to a target protein with high affinity, e.g., as determined by an SPR binding assay or an ELISA assay. The compounds of the subject peptidic library may exhibit an affinity for a target protein of 1 uM or less, such as 300 nM or less, 100 nM or less, 30 nM or less, 10 nM or less, 5 nM or less, 2 nM or less, 1 nM or less, 300 pM or less, 100 pM or less, 30 pM or less, 10 pM or less, or even less. The compounds of the subject peptidic libraries may exhibit a specificity for a target protein, e.g., as determined by comparing the affinity of the compound for the target protein with that for a reference protein (e.g., an albumin protein), that is 5:1 or more 10:1 or more, such as 30:1 or more, 100:1 or more, 300:1 or more, 1000:1 or more, or even more.

Target Molecules

Once the subject libraries are prepared they can be selected and/or screened for binding to one or more target molecules. In addition, the libraries may be selected for improved binding affinity to certain target molecule. The target molecules may be any type of protein-binding or antigenic molecule, such as proteins, nucleic acids, carbohydrates or small molecules. In certain embodiments, the target molecule is a therapeutic target molecule or a diagnostic target molecule, or a fragment thereof, or a mimic thereof.

As used herein, the term "a target protein" refers to all members of the target family, and fragments and enantiomers thereof, and protein mimics thereof. The target proteins of interest that are described herein are intended to include all members of the target family, and fragments and enantiomers thereof, and protein mimics thereof, unless explicitly described otherwise. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially, as well as fusion proteins containing a target molecule, as well as synthetic L- or D-proteins.

As used herein, the term "protein mimic" refers to a peptidic compound that mimics a binding property of a protein of interest, e.g., a target protein. In general terms, the target protein mimic includes an essential part of the original target protein (e.g., an epitope or essential residues thereof) that is necessary for forming a potential binding surface, such that the target protein mimic and the original target protein are each capable of binding specifically to a binding moiety of interest, e.g., an antibody or a D-peptidic compound. In some embodiments, the part(s) of the original target protein that is essential for binding is displayed on a scaffold such that potential binding surface of the original target protein is mimicked. Any suitable scaffold for displaying the minimal essential part of the target protein may be used, including but not limited to antibody scaffolds, scFv, anticalins, non-antibody scaffolds, mimetics of protein secondary and tertiary structures. In some embodiments, a target protein mimic includes residues or fragments of the original target protein that are incorporated into a protein scaffold, where the scaffold mimics a structural motif of the target protein. For example, by incorporating residues of the target protein at desirable positions of a convenient scaffold, the protein mimic may present a potential binding surface that mimics that of the original target protein. In some embodiments, the native structure of the fragments of the original target protein are retained using methods of conformational constraint. Any convenient methods of conformationally constraining a peptidic compound may be used, such as but not limited to, bioconjugation, dimerization (e.g., via a linker), multimerization, or cyclization.

In certain embodiments, the target molecule is a hormone, a growth factor, a receptor, an enzyme, a cytokine, an osteoinductive factor, a colony stimulating factor or an immunoglobulin.

In certain embodiments, the target molecule may be one or more of the following: growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, Her-2, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins (e.g., a IL-4, IL-8, IL-1-a, IL-6, IL-12, IL-13, IL-17 or IL-23 protein), growth factor blockers (VEGF-A, -D, PDGF-B), a bi-specific blocker (e.g., VEGF-A+PDGF-B), a receptor agonist (e.g., Robo4), bone morphogenetic proteins, LIF, SCF, FLT-3 ligand, kit-ligand, SH3 domain, apoptosis protein, hepatocyte growth factor, hepatocyte growth factor receptor, neutravidin, maltose binding protein, angiostatin, aFGF, bFGF, TGF-alpha, TGF-beta, HGF, TNF-alpha, angiogenin, IL-8, thrombospondin, the 16-kilodalton N-terminal fragment of prolactin and endostatin.

In certain embodiments, the target molecule may be a therapeutic target protein for which structural information is known, such as, but not limited to: Raf kinase (a target for the treatment of melanoma), Rho kinase (a target in the prevention of pathogenesis of cardiovascular disease), nuclear factor kappaB (NF-.kappa.B, a target for the treatment of multiple myeloma), vascular endothelial growth factor (VEGF) receptor kinase (a target for action of antiangiogenetic drugs), Janus kinase 3 (JAK-3, a target for the treatment of rheumatoid arthritis), cyclin dependent kinase (CDK) 2 (CDK2, a target for prevention of stroke), FMS-like tyrosine kinase (FLT) 3 (FLT-3; a target for the treatment of acute myelogenous leukemia (AML)), epidermal growth factor receptor (EGFR) kinase (a target for the treatment of cancer), protein kinase A (PKA, a therapeutic target in the prevention of cardiovascular disease), p21-activated kinase (a target for the treatment of breast cancer), mitogen-activated protein kinase (MAPK, a target for the treatment of cancer and arthritis), c-Jun NH.sub.2-terminal kinase (JNK, a target for treatment of diabetes), AMP-activated kinase (AMPK, a target for prevention and treatment of insulin resistance), lck kinase (a target for immunosuppression), phosphodiesterase PDE4 (a target in treatment of inflammatory diseases such as rheumatoid arthritis and asthma), Abl kinase (a target in treatment of chronic myeloid leukemia (CML)), phosphodiesterase PDE5 (a target in treatment of erectile dysfunction), a disintegrin and metalloproteinase 33 (ADAM33, a target for the treatment of asthma), human immunodeficiency virus (HIV)-1 protease and HIV integrase (targets for the treatment of HIV infection), respiratory syncytial virus (RSV) integrase (a target for the treatment of infection with RSV), X-linked inhibitor of apoptosis (XIAP, a target for the treatment of neurodegenerative disease and ischemic injury), thrombin (a therapeutic target in the treatment and prevention of thromboembolic disorders), tissue type plasminogen activator (a target in prevention of neuronal death after injury of central nervous system), matrix metalloproteinases (targets of anticancer agents preventing angiogenesis), beta secretase (a target for the treatment of Alzheimer's disease), src kinase (a target for the treatment of cancer), fyn kinase, lyn kinase, zeta-chain associated protein 70 (ZAP-70) protein tyrosine kinase, extracellular signal-regulated kinase 1 (ERK-1), p38 MAPK, CDK4, CDK5, glycogen synthase kinase 3 (GSK-3), KIT tyrosine kinase, FLT-1, FLT-4, kinase insert domain-containing receptor (KDR) kinase, and cancer osaka thyroid (COT) kinase.

In certain embodiments, the target molecule is a target protein that is selected from the group consisting of a VEGF protein (e.g., VEGF-A, VEGF-C or VEGF-D), a RANKL protein, a NGF protein, a TNF-alpha protein, a SH2 domain containing protein, a SH3 domain containing protein, an IgE protein a BLyS protein (Oren et al., "Structural basis of BLyS receptor recognition", Nature Structural Biology 9, 288-292, 2002), a PCSK9 protein (Ni et al., "A proprotein convertase subtilisin-like/kexin type 9 (PCSK9) C-terminal domain antibody antigen-binding fragment inhibits PCSK9 internalization and restores low density lipoprotein uptake", J. Biol. Chem. 2010 Apr. 23; 285(17):12882-91), a DLL4 protein (Garber, "Targeting Vessel Abnormalization in Cancer", JNCI Journal of the National Cancer Institute 2007 99(17):1284-1285), an Ang2 (Angiopoietin-2) protein, a *Clostridium difficile* Toxin A or B protein (e.g., Ho et al., "Crystal structure of receptor-binding C-terminal repeats from *Clostridium difficile* toxin A", (2005) Proc. Natl. Acad.

Sci. Usa 102: 18373-18378), a CTLA4 protein (Cytotoxic T-Lymphocyte Antigen 4), and fragments thereof. In certain embodiments, the target protein is a VEGF protein. In certain embodiments, the target protein is a SH2 domain containing protein (e.g., a 3BP2 protein) or a SH3 domain containing protein (e.g., a ABL or a Src protein).

In some instances, the target molecule is selected from PDGF-B, Robo4, Htra1, hemagglutinin, Nav1.7, CD5, CD19, CD38, CD40, IGF-1R, GM-CSF, PCSK9, BlyS, Ang2, EGFR, HER2, Robo4, Htra1, CXCL5, Sclerostin, R-Spondin, MD-2, an Influenza HA hemagglutinin protein or a coiled coil mimic thereof, HCV, an HIV protein.

Utility

The libraries of the invention, e.g., as described above, find use in a variety of applications. Applications of interest include, but are not limited to, screening applications and research applications.

The screening methods, e.g., as described above, find use in a variety of applications, including selection and/or screening of the subject libraries in a wide range of research and therapeutic applications, such as therapeutic lead identification and affinity maturation, identification of diagnostic reagents, development of high throughput screening assays, development of drug delivery systems for the delivery of toxins or other therapeutic moieties. The subject screening methods may be exploited in multiple settings.

In some cases, the subject libraries may find use as research tools to analyze the roles of proteins of interest in modulating various biological processes, e.g., angiogenesis, inflammation, cellular growth, metabolism, regulation of transcription and regulation of phosphorylation. For example, antibody libraries have been useful tools in many such areas of biological research and lead to the development of effective therapeutic agents, see Sidhu and Fellhouse, "Synthetic therapeutic antibodies," Nature Chemical Biology, 2006, 2(12), 682-688.

The subject libraries may be exploited as research tools in the development of clinical diagnostics, e.g., in vitro diagnostics (e.g., for targeting various biomarkers), or in vivo tumor imaging agents. The screening of libraries of binding molecules (e.g., aptamers and antibodies) has found use in the development of such clinical diagnostics, see for example, Jayasena, "Aptamers: An Emerging Class of Molecules That Rival Antibodies in Diagnostics," Clinical Chemistry. 1999; 45:1628-1650.

The following examples are offered by way of illustration and not by way of limitation.

EXPERIMENTAL

Example 1

A. Preparation of Scaffolded Peptidic Libraries
1. Cloning and Display of Scaffolds on M13 Filamentous Phage The secB export pathway may be utilized for phage display where the protein is exported to the periplasm in the unfolded form and folding occurs in the periplasm. This format of display is convenient for proteins that require oxidizing conditions for folding (i.e. proteins with disulfide bonds). Alternatively, the TAT pathway may be utilized to export proteins that are well folded in the cytoplasm and has quality control mechanisms to eliminate misfolded and aggregated proteins (Waraho-Zhmayev et al., "A microbial sensor for discovering structural probes of protein misfolding and aggregation," *Prion* 7; DeLisa et al. (2003) "Folding quality control in the export of proteins by the bacterial twin-arginine translocation pathway," *Proc Natl Acad Sci USA* 100, 6115-20).

Formats for display of peptidic scaffolds include N-terminal fusion of the scaffold to phage coat proteins p3 or p8. In addition, the secretion signals for the fusion proteins are varied with either the StII signal sequence (secB pathway) or the TorA signal sequence (TAT pathway). Four vectors were constructed based on a standard phagemid with ampicillin resistance, LaqIq repressor and ptac promoter. The open reading frames (partial) are shown below.

The sequences below show open reading frames (ORFs) and p3-StII and p8-StII vectors that scaffolds of interest were cloned into for phage display. The scaffolds were synthesized with a N-terminal FLAG tag followed by a BamHI cut site and gene sequence and cloned in using NsiI and SacI cut sites.

```
p3-StII vector
                                                     NsiI
ATGAAAAAGAATATCGCATTTCTTCTTGCATCTATGTTCGTTTTTTCTATTGCTACAAATGCCTATGCATCTTCTCATGTAGC
 M  K  K  N  I  A  F  L  L  A  S  M  F  V  F  S  I  A  T  N  A  Y  A  S
                         StII signal sequence SacI
TCTCATGTAGCGGGAGCTCTGGAGACAAAACTCACACATGCGGCCGGCCCTCTGGTTCCGGTGATTTTGATTATGAAAAGATG . . .
        G  S  S  G  D  K  T  H  T  C  G  R  P  S  G  S  G  D  F  D  Y  E  K  M . . .
                      Fab dimerization                     Gene 3 (C-terminal domain)

(SEQ ID NO: 257)
(SEQ ID NO: 258)

p8-StII vector
                                                     NsiI
ATGAAAAAGAATATCGCATTTCTTCTTGCATCTATGTTCGTTTTTTCTATTGCTACAAATGCCTATGCATCTTCTCATGTAGC
 M  K  K  N  I  A  F  L  L  A  S  M  F  V  F  S  I  A  T  N  A  Y  A  S
                         StII signal sequence SacI
TCTCATGTAGCGGGAGCTCTGGAGCCGAGGGTGACGATCCCGCAAAAGCGGCCTTTAACTCC . . . (SEQ ID NO: 259)
        G  S  S  G  A  E  G  D  D  P  A  K  A  A  F  N  S . . . (SEQ ID NO: 260)
                              Gene 8
```

-continued p3-TorA vector
```
ATGAACAATAACGATCTCTTTCAGGCATCACGTCGGCGTTTTCTGGCACAACTCGGCGGCTTAACCGTCGCCGGGATGCTGGGG
 M   N   N   N   D   L   F   Q   A   S   R   R   R   F   L   A   Q   L   G   G   L   T   V   A   G   M   L   G
                                        TorA signal sequence NsiI
CCGTCATTGTTAACGCCGCGTCGTGCGACTGCGGCGCAAGCGGCGACTGATGCATCTTCTCATGTAGCTCTCATGTAGC
 P   S   L   L   T   P   R   R   A   T   A   A   Q   A   A   T   D   A   S SacI
GGGAGCTCTGGAGACAAAACTCACACATGCGGCCGGCCCTCTGGTTCCGGTGATTTTGATTATGAAAAGATG (SEQ ID NO: 71)
 G   S   S   G   D   K   T   H   T   C   G   R   P   S   G   S   G   D   F   D   Y   E   K   M ... (SEQ ID NO: 72)
                 Fab dimerization                        Gene 3 (C-terminal domain)
``` p8-TorA vector
```
ATGAACAATAACGATCTCTTTCAGGCATCACGTCGGCGTTTTCTGGCACAACTCGGCGGCTTAACCGTCGCCGGGATGCTGGGG
 M   N   N   N   D   L   F   Q   A   S   R   R   R   F   L   A   Q   L   G   G   L   T   V   A   G   M   L   G
                                        TorA signal sequence NsiI
CCGTCATTGTTAACGCCGCGTCGTGCGACTGCGGCGCAAGCGGCGACTGATGCATCTTCTCATGTAGCTCTCATGTAGC
 P   S   L   L   T   P   R   R   A   T   A   A   Q   A   A   T   D   A   S SacI
GGGAGCTCTGGAGCCGAGGGTGACGATCCCGCAAAAGCGGCCTTTAACTCC ... (SEQ ID NO: 73)
 G   S   S   G   A   E   G   D   D   P   A   K   A   A   F   N   S ... (SEQ ID NO: 74)
                          Gene 8
```

Above is depicted a system for cloning scaffolds of interest into p3-TorA and p8-TorA vectors for phage display.

and SacI sites. A exemplary reading open reading frame (ORF) is shown below:

```
ATGAAAAAGAATATCGCATTTCTTCTTGCATCTATGTTCGTTTTTTCTATTGCTACAAAT
 M   K   K   N   I   A   F   L   L   A   S   M   F   V   F   S   I   A   T   N
                       StII secretion signal NsiI                                                BamHI
GCCTATGCATCCGATTATAAAGATGATGATGATAAAGGCGGATCCACCTGTGGTGGTGAA
 A   Y   A   S   D   Y   K   D   D   D   D   K   G   G   S   T   C   G   G   E
                       FLAG tag ACTTGTTCCGCTGCGCAGGTATGCCTGAAAGGTAAATGCGTGTGCAACGAGGTTCACTGC
 T   C   S   A   A   Q   V   C   L   K   G   K   C   V   C   N   E   V   H   C
                                    Scaffold CGCATCCGTTGTAAATACGGCCTGAAAAAGGACGAAAATGGCTGCGAATATCCGTGTTCT
 R   I   R   C   K   Y   G   L   K   K   D   E   N   G   C   E   Y   P   C   S
                                    Scaffold SacI
TGCGCAAAAGGGAGCTCTGGAGCCGAGGGEGACGATCCCGCAAAAGCGGCC ... (SEQ ID NO: 261)
 C   A   K   G   S   S   G   A   E   G   D   D   P   A   K   A   A ... (SEQ ID NO: 262)
                          Gene 8
```

The quality control mechanisms of the TAT secretion pathway negatively select for misfolded and aggregated proteins. Non-disulfide bonded scaffolds of interest were cloned into p3-TorA and p8-TorA vectors with the ORFs shown using NsiI and SacI cut sites.

These vectors are designed with the same restriction sites (NsiI and SacI) to allow easy transfer of scaffolds and peptidic compounds to other display formats and expression vectors. For the TorA signal sequence vectors four additional residues (ATDA) from TorA protein are added at the N-terminus as residues near the cleavage site are important for specificity of TAT pathway export (Tullman-Ercek et al. (2007). Export pathway selectivity of *Escherichia coli* twin arginine translocation signal peptides. *J Biol Chem* 282, 8309-16). For the p3-vectors, a dimerization sequence derived from antibody fragments is used to improve phage recovery during selections.

The genes for the scaffolds are codon-optimized for bacterial expression, synthesized with an N-terminal FLAG tag and cloned into p3-StII and p8-StII vectors using NsiI A BamHI restriction site is included between the FLAG tag and scaffold to facilitate transfer of protein to expression vectors without the FLAG tag.

Scaffolds without disulfide bonds are transferred to p3-TorA and p8-TorA display vectors. The following primers are used to amplify the scaffold DNA from p3-StII vector Forward Primer (Anneals in signal sequence)
(SEQ ID NO: 263)
GCTACAAATGCCTATGCATCC Reverse Primer (Anneals in dimerization sequence)
(SEQ ID NO: 264)
GTTTTGTCTCCAGAGCTCCC The PCR fragments are digested with NsiI and SacI, purified and ligated into the target vectors.

All the plasmids are transformed into chemically competent OmniMax T1R cells. Starting from single colonies, phage supernatants are prepared in 96 well boxes using previously described protocols (Fellouse & Sidhu (2007)

*Making antibodies in bacteria.* Making and using antibodies (Howard, G. C. & Kaser, M. R., Eds.), CRC Press, Boca Raton, Fla.). The display levels of the scaffolds are then compared by the signals in an anti-FLAG ELISA. The presence of a N-terminal FLAG tag ensures that the full-length protein is displayed on phage. The ELISA is performed according to previously described protocols (Fellouse, F. A. & Sidhu, S. S. (2007). *Making antibodies in bacteria.* Making and using antibodies (Howard, G. C. & Kaser, M. R., Eds.), CRC Press, Boca Raton, Fla.; Sidhu et al. (2007). Identifying specificity profiles for peptide recognition modules from phage-displayed peptide libraries. *Nat Protoc* 2, 1368-86) as briefly described below 1. The phage supernatant is diluted 3 fold in PBT buffer and added to ELISA plates (Nunc Maxisorp plates coated with 3 ug/ml Anti-FLAG antibody (Sigma-Aldrich) and blocked with BSA) and bound for 1 hr at room temperature.
2. The plates are washed 3× with PT buffer and incubated with 1:5000 dilution of Anti-M13 HRP antibody (GE Healthcare) in PBT buffer for 30 min.
3. The plates are washed 3× with PT buffer and developed with TMB substrate (KPL Biosciences).

Library Design and Randomization

The following protocol is one exemplary method that may be adapted for use in the production of the subject libraries. A set of variant residues of a scaffold of interest are selected (e.g., 8-16 residues) for mutagenesis. One convenient strategy is to allow all 20 amino acids in the randomized positions (e.g., using the degenerate codon NNK). In some cases, the theoretical diversity of the sequence space vastly exceeds the experimental diversity that can be generated using convenient protocols). An alternative approach is to restrict and bias the randomization of variant amino acid residues (e.g., residues that tend to predominate in protein-protein interactions), thereby enabling better sampling of the sequence space in the libraries. Below is one codon of interest that uses a restricted set of amino acids and generates a bias towards residues of interests:

X encodes (a custom mix of trimer phophoramidites (Glen Research, Inc)) 25% Y, 15% R, 15% W, 10% V, 10% S, 10% A, 5% F, 5% H.

Residues of interest for such restricted sets of amino acids include, but are not limited to, aromatic residues (e.g., Tyr, Trp), Arg, small residues (e.g., Ser, Ala) and Asp, and the like.

Library Selections Against Target Protein and Negative Selection with BSA

The selection procedure as described in previous protocols (Fellhouse & Sidhu, 2007) may be adapted for use in screening the subject libraries. Although the method below is described for L-VEGF, the method can be adapted to screen for binding to any target.

1. Coat NUNC Maxisorp plate wells with 100 µl of L-VEGF (5 µl in PBS) for 2 h at room temperature. Coat 5 wells for selection and 1 well for phage pool ELISA.
2. Remove the coating solution and block for 1 h with 200 µl of PBS, 0.2% BSA. At the same time, block an uncoated well as a negative control for pool ELISA. Also block 7 wells for pre-incubation of library on a separate plate.
3. Remove the block solution from the pre-incubation plate and wash four times with PT buffer.
4. Add 100 µl of library phage solution (precipitated and resuspended in PBT buffer) to each blocked wells. Incubate at room temperature for 1 h with gentle shaking.
5. Remove the block solution from selection plate and wash four times with PT buffer.
6. Transfer library phage solution from pre-incubation plate to selection plate (5 selection wells+2 controls for pool ELISA)
7. Remove the phage solution and wash 8-10 times with PT buffer (increased based on pool ELISA signal from previous round).
8. To elute bound phage from selection wells, add 100 µl of 100 mM HCl. Incubate 5 min at room temperature. Transfer the HCl solution to a 1.5-ml microfuge tube. Adjust to neutral pH with 11 µl of 1.0 M Tris-HCl, pH 11.0.
9. In the meantime add 100 µl of anti-M13 HRP conjugate (1:5000 dilution in PBT buffer) to the control wells and incubate for 30 min.
10. Wash control wells four times with PT buffer. Add 100 µl of freshly prepared TMB substrate. Allow color to develop for 5-10 min.
11. Stop the reaction with 100 µl of 1.0 M $H_3PO_4$ and read absorbance at 450 nm in a microtiter plate reader. The enrichment ratio can be calculated as the ratio of signal from coated vs uncoated well.
12. Add 250 µl eluted phage solution to 2.5 ml of actively growing *E. coli* XL1-Blue ($OD_{600}$<0.8) in 2 YT/tet medium. Incubate for 20 min at 37° C. with shaking at 200 rpm.
13. Add M13KO7 helper phage to a final concentration of $10^{10}$ phage/ml. Incubate for 45 min at 37° C. with shaking at 200 rpm.
14. Transfer the culture from the antigen-coated wells to 25 volumes of 2 YT/carb/kan medium and incubate overnight at 37° C. with shaking at 200 rpm.
15. Isolate phage by precipitation with PEG/NaCl solution, resuspend in 1.0 ml of PBT buffer
16. Repeat the selection cycle for 4 rounds.

Negative Selection with GST Tagged Protein

A more stringent negative selection procedure is as follows. The selection process is essentially the same as described above except that:

i) For Rounds 1 and 2 the libraries are pre-incubated on GST coated (10 µg/ml in PBS) and blocked wells.
ii) For Rounds 3 and 4, the libraries are pre-incubated with 0.2 mg/ml GST in solution for 1 hr before transfer to selection wells
iii) The control wells for pool ELISA are coated with GST (5 µg/ml in PBS)

Selections of Libraries Against Anti-FLAG

Misfolded proteins are degraded in the periplasm and will not be displayed on phage (Missiakas & Raina, "Protein misfolding in the cell envelope of *Escherichia coli*: new signaling pathways," Trends in Biochemical Sciences, 1997, 22, 59-63). The TAT pathway secretion signals allows exclusion of misfolded proteins from display on phage. Stably folded proteins can therefore be selected for display of the N-terminal FLAG tag.

The selections are performed by a method similar to the one described above except that the library is directly added to selection wells coated with anti-FLAG antibody (5 µg/ml diluted in PBT) and there is no preincubation step.

Analysis of Single-Clones by Direct Binding ELISA

The following protocol is an adapted version of previous protocols (Fellouse & Sidhu 2007; Tonikian et al., "Identifying specificity profiles for peptide recognition modules from phage-displayed peptide libraries," Nat. Protoc., 2007, 2, 1368-86):

1. Inoculate 450 µl aliquots of 2 YT/carb/KO7 medium in 96-well microtubes with single colonies harboring phagemids and grow for 21 hrs at 37° C. with shaking at 200 rpm.
2. Centrifuge at 4,000 rpm for 10 min and transfer phage supernatants to fresh tubes.
3. Coat 3 wells of a 384 well NUNC maxisorb plate per clone, with 2 µg/ml of L-VEGF, Neutravidn, Erbin-GST respectively and leave one well uncoated. Incubate for 2 hrs at room temperature and block the plates (all 4 well).
4. Wash the plate four times with PT buffer.
5. Transfer 30 µl of phage supernatant to each well and incubate for 2 hrs at room temperature with gentle shaking.
6. Wash four times with PT buffer.
7. Add 30 µl of anti-M13-HRP conjugate (diluted 1:5000 in PBT buffer). Incubate 30 min with gentle shaking.
8. Wash four times with PT buffer
9. Add 30 µl of freshly prepared TMB substrate. Allow color to develop for 5-10 min.
10. Stop the reaction with 100 µl of 1.0 M $H_3PO_4$ and read absorbance at 450 nm in a microtiter plate reader.

Example 2

A. Cloning and Display of Scaffolds

A diverse set of small protein scaffolds was selected. The genes for the scaffolds were codon-optimized for bacterial expression and synthesized with an N-terminal FLAG tag and cloned into phagemid vector p8-StII (vector sequences attached) using NsiI and SacI sites by a vendor (Biobasic Inc., Markham, ON, Canada). A typical ORF is shown below The display of the scaffold on phage particles was verified by binding to anti-FLAG. The ELISA was performed according to conventional protocols (see e.g., Fellouse, F. A. & Sidhu, S. S. (2007). Making antibodies in bacteria. Making and using antibodies (Howard, G. C. & Kaser, M. R., Eds.), CRC Press, Boca Raton, Fla.; and Tonikian, R., Zhang, Y., Boone, C. & Sidhu, S. S. (2007). Identifying specificity profiles for peptide recognition modules from phage-displayed peptide libraries. Nat Protoc 2, 1368-86) which are briefly described below:

1. The phage supernatant is diluted 3 fold in PBT buffer and added to ELISA plates (Nunc Maxisorp plates coated with 3 ug/ml Anti-FLAG antibody (Sigma-Aldrich, Cat #F1804) and blocked with BSA) and bound for 1 hr at room temperature.
2. The plates are washed 3× with PT buffer and incubated with 1:5000 dilution of Anti-M13 HRP antibody (GE Healthcare, Cat#) in PBT buffer for 30 min.
3. The plates are washed 3× with PT buffer and developed with TMB substrate (KPL).

B. Library Design

Solvent exposed surface area (SASA) analysis of individual residues in the scaffolds were generated using GETarea online software (see e.g., Fraczkiewicz, R. & Braun, W. (1998). Exact and efficient analytical calculation of the accessible surface areas and their gradients for macromolecules. Journal of Computational Chemistry 19, 319-333). A set of surface exposed residues that form a contiguous patch of surface on the scaffold was selected for mutagenesis.

In general:

i. To generate high-affinity binding interfaces, 8-16 residues were selected to generate a binding interface of greater than 500 A°2.
ii. Where a crystal structure of the scaffold in complex with an interaction partner was available, the interface residues were identified using SASA analysis of bound and free forms.

While a strategy of allowing all 20 amino acids in the randomized positions (using the degenerate codon NNK)

```
ATGAAAAAGAATATCGCATTTCTTCTTGCATCTATGTTCGTTTTTTCTATTGCTACAAAT
 M   K   K   N   I   A   F   L   L   A   S   M   F   V   F   S   I   A   T   N
                        StII secretion signal GCCTATGCATCCGATTATAAAGATGATGATGATAAAGGCGGATCCCCACCGACCGAACCG
 A   Y   A   S   D   Y   K   D   D   D   D   K   G   G   S   P   P   T   E   P
                        Flag tag CTGCCGGATGGCTGGATTATGACTTTCCATAACTCCGGCGTGCCGGTTTATCTGCACCGC
 L   P   D   G   W   I   M   T   F   H   N   S   G   V   P   V   Y   L   H   R
                        Scaffold GAGTCCCGTGTAGTCACCTGGAGCCGTCCGTACTTTCTGGGTACGGGTTCTATCCGTAAA
 E   S   R   V   V   T   W   S   R   P   Y   F   L   G   T   G   S   I   R   K CACGACCCGCCGCTGTCTTCTATCCCTTGCCTGGGGAGCTCTGGAGCCGAGGGTGACGAT
 H   D   P   P   L   S   S   I   P   C   L   G   S   S   G   A   E   G   D   D CCCGCAAAAGCGGCCTTTAACTCCCTGCAAGCCTCAGCGACCGAATATATCGGTTATGCG
 P   A   K   A   A   F   N   S   L   Q   A   S   A   T   E   Y   I   G   Y   A
                        Gene 8

TGGGCGATGGTTGTTGTCATTGTCGGCGCAACTATCGGTATCAAGCTGTTTAAGAAATTC
 W   A   M   V   V   V   I   V   G   A   T   I   G   I   K   L   F   K   K   F

ACCTCGAAAGCAAGCTGATAA (SEQ ID NO: 265)
 T   S   K   A   S   *   *   (SEQ ID NO: 266)
``` may be used, in some cases, this strategy is not optimal as the theoretical diversity of the sequence space may exceed the experimental diversity that can be generated using conventional protocols. An alternative approach is to restrict and bias the randomization to those residues that are usually enriched in protein-protein interactions, thereby enabling better sampling of the sequence space in the libraries. For these libraries the following codon was used for randomization (except as otherwise noted):

(B1)HT encoding 16.6% Y, 16.6% S, 16.6% F, 8.3% L, 8.3% P, 8.3% H, 8.3% V, 8.3% A, 8.3% D; where B1 is a custom mix of 25% C, 25% G and 50% T, H is a degenerate mix of A/C/T C. Library Construction and Quality Control The libraries were constructed according to conventional protocols (see e.g., Fellouse, F. A. & Sidhu, S. S. (2007). Making antibodies in bacteria. Making and using antibodies (Howard, G. C. & Kaser, M. R., Eds.), CRC Press, Boca Raton, Fla.; and Tonikian, R., Zhang, Y., Boone, C. & Sidhu, S. S. (2007). Identifying specificity profiles for peptide recognition modules from phage-displayed peptide libraries. Nat Protoc 2, 1368-86). The list of oligonucleotides used for each library is shown in FIG. 38-42. Up to 4 electroporations were performed for each library and pooled together to improve library diversity.

12-24 random clones from each library were plated and anti-FLAG ELISA was performed as described in Section A. The same clones were sequenced to estimate the % of unique sequences.

Table 1 summarizes the data from library construction and characterization. The number of transformants obtained after electroporation is an indicator of the sequence diversity in the library. Sequence diversity is estimated by multiplying the number of transformants by the fraction of sequences with desired mutations. A FLAG positive variant is defined as a clone from the library that binds to anti-FLAG antibody with an ELISA signal of at least 5 times the background. The functional diversity, an estimate of expression of diverse clones on phage, is obtained by multiplying the fraction of FLAG positive variants with the sequence diversity.

D. Library Panning Against D-VEGFA

A subset of 8 libraries was pooled together and the following panning procedure was used:

1. 100 ul of 5 ug/ml D-VEGFA (in PBS buffer) was added to 6 wells of Nunc Maxisorp 96 well plates and incubated at room temperature for 2 hrs on a plate shaker.
2. The antigen-coated plate was blocked with 200 ul BSA (2 mg/ml in PBS buffer) along with 6 uncoated wells for negative selection. The plates were incubated for 1 hr at room temperature.
3. 100 ul of library was added to the negative selection plate and incubated for 1 hr to screen against non-specific binders.
4. The library was then transferred to selection plate and incubated for 2 hrs at room temperature.
5. Following binding the plate was washed 8-12 times with PT buffer (1×PBS buffer, 0.05% Tween20) and the wells were eluted with 100 ul of 100 mM HCl and neutralized with 11 ul of 1M Tris-HCl pH 11.0
6. Following neutralization, the eluted phage was again added to BSA blocked Maxisorp plates to further screen out non-specific binders. The eluted phage was incubated for 1 hr at room temperature.
7. 300 ul of cleared elute was added to 3 ml of OmniMax cells at O.D. 0.6 and incubated at 37° C. for 30 min, shaking at 200 rpm. 3 ul of M13Ko7 (1×1013 cfu/ml) was added to the culture and incubated for 45 min at 37° C. with shaking.
8. The culture was transferred to 30 ml of 2 YT/carb/kan media and grown overnight at 37° C.

TABLE 1

Summary of Quality Control Data for selected libraries

| ID # | Number of transformants | Fraction correct sequence | Fraction of FLAG positive variants | Sequence Diversity (×10^9) | Functional Diversity (×10^9) |
|---|---|---|---|---|---|
| SCF2 | $9 \times 10^9$ | 0.58 | 0.93 | $5.3 \times 10^9$ | $4.9 \times 10^9$ |
| SCF3 | $1.55 \times 10^{10}$ | 0.78 | 0.89 | $1.2 \times 10^{10}$ | $1 \times 10^{10}$ |
| SCF4 | $9 \times 10^9$ | 0.71 | 0.76 | $6.4 \times 10^9$ | $4.9 \times 10^9$ |
| SCF7 | $1.3 \times 10^{10}$ | 0.79 | 0.62 | $1 \times 10^{10}$ | $6.3 \times 10^9$ |
| SCF8 | $8 \times 10^9$ | 0.78 | 0.85 | $6.2 \times 10^9$ | $5.3 \times 10^9$ |
| SCF15 | $1.1 \times 10^{10}$ | 0.88 | 0.86 | $9.7 \times 10^9$ | $8.4 \times 10^9$ |
| SCF23 | $4.25 \times 10^9$ | 0.96 | 0.68 | $4 \times 10^9$ | $2.8 \times 10^9$ |
| SCF24-Lib1 | $8 \times 10^9$ | 0.83 | 0.53 | $6.7 \times 10^9$ | $3.5 \times 10^9$ |
| SCF24-Lib2 | $9 \times 10^9$ | 0.94 | 0.76 | $8.5 \times 10^9$ | $6.5 \times 10^9$ |
| SCF27 | $4.75 \times 10^9$ | 0.83 | 0.89 | $3.9 \times 10^9$ | $3.5 \times 10^9$ |
| SCF28 | $1.7 \times 10^{10}$ | 0.70 | 0.69 | $1.2 \times 10^{10}$ | $8.1 \times 10^9$ |
| SCF29 | $1.2 \times 10^{10}$ | 0.83 | 0.84 | $9.9 \times 10^9$ | $8.3 \times 10^9$ |
| SCF32 | $1.33 \times 10^{10}$ | 0.83 | 0.95 | $1.1 \times 10^{10}$ | $1 \times 10^{10}$ |
| SCF37 - lib.1 | $8.5 \times 10^9$ | 0.70 | 0.81 | $5.9 \times 10^9$ | $4.8 \times 10^9$ |
| SCF38 - lib.1 | $6.8 \times 10^9$ | 0.58 | 1.00 | $4 \times 10^9$ | $4 \times 10^9$ |
| SCF53 | $7.5 \times 10^9$ | 0.42 | 1.00 | $3.1 \times 10^9$ | $3.1 \times 10^9$ |
| SCF75 | $4.3 \times 10^9$ | 0.54 | 0.69 | $2.3 \times 10^9$ | $1.6 \times 10^9$ |
| SCF42 | $5.1 \times 10^9$ | 0.70 | 1.00 | $3.5 \times 10^9$ | $3.5 \times 10^9$ |
| SCF47 | $1 \times 10^{10}$ | 0.75 | 0.78 | $7.1 \times 10^9$ | $5.5 \times 10^9$ |
| SCF63 | $6.75 \times 10^9$ | 0.88 | 0.71 | $5.9 \times 10^9$ | $4.2 \times 10^9$ |
| SCF56-Lib1 | $5.8 \times 10^9$ | 0.80 | 1.00 | $4.6 \times 10^9$ | $4.6 \times 10^9$ |
| SCF56-Lib2 | $3.25 \times 10^9$ | 0.67 | 1.00 | $2.2 \times 10^9$ | $2.2 \times 10^9$ |
| SCF95 | $9.3 \times 10^9$ | 0.48 | 1.00 | $4.4 \times 10^9$ | $4.4 \times 10^9$ |
| SCF96 | $6.9 \times 10^9$ | 0.78 | 1.00 | $5.4 \times 10^9$ | $5.4 \times 10^9$ |
| SCF55-Lib.1 | $5.6 \times 10^9$ | 0.79 | 0.95 | $4.4 \times 10^9$ | $4.2 \times 10^9$ |
| SCF65 | $1.8 \times 10^{10}$ | 0.83 | 0.80 | $1.5 \times 10^{10}$ | $1.2 \times 10^{10}$ |
| SCF66 | $1.75 \times 10^{10}$ | 0.73 | 1.00 | $1.3 \times 10^{10}$ | $1.3 \times 10^{10}$ |
| SCF70 | $2 \times 10^{10}$ | 0.82 | 0.89 | $1.6 \times 10^{10}$ | $1.5 \times 10^{10}$ |
| SCF40 | $2.37 \times 10^{10}$ | 0.92 | 0.91 | $2.2 \times 10^{10}$ | $2 \times 10^{10}$ |
| SCF44 | $1.72 \times 10^{10}$ | 0.64 | 1.00 | $1.1 \times 10^{10}$ | $1.1 \times 10^{10}$ |
| SCF64 | $1.17 \times 10^{10}$ | 0.70 | 0.71 | $8.2 \times 10^9$ | $5.8 \times 10^9$ |

9. For second round of selection, the phage from overnight culture was harvested and suspended in 1 ml of PBT buffer and the steps 1 to 8 were repeated.
10. Due high phage titers in elute, for 3rd and 4th round of selections the overnight phage supernatant was directly added to selection wells following pH adjustment with 10× PBS pH7.4.

The enrichment of phage pool during selections for specific binders to D-VEGFA was monitored using ELISA.

Individual clones from 4th round phage pool were screened for specific binding to D-VEGFA by ELISA and sequenced.

E. Affinity Maturation of Selected Clones

Affinity maturation libraries of selected clones were constructed and panned in a similar manner as described above. Since a crystal structure is unavailable, the same residues that were mutated in the naïve library were mutated again, with a biased codon to allow the current amino acid in that position to remain the same with a 50% probability while allowing the occurrence of all other 19 amino acids.

TABLE 2

Oligos for library synthesis of Example 2
The codon used for mutation is (B1)HT where B1 is a mix of 25% C, 25% G, 50% T. This is denoted in various equivalent formats: (B1), (B1: 00252550), [00-25-25-50] in the ordered oligos due to different vendors

| Oligo # | SEQ ID NO: | Oligo sequences |
| --- | --- | --- |
| MU-SCF2-1 | 200 | CTGCCGGATGGCTGG (B1: 00252550)HT ATG (B1)HT (B1)HT CATAACTCCGGCGTGCCGGTTTAT (B1)HT CAC (B1)HT (B1)HT TCC (B1)HT GTAGTCACCTGGAGC |
| MU-SCF2-2 | 201 | CGTCCGTACTTTCTGGGT (B1: 00252550)HT GGT (B1)HT (B1)HT (B1)HT (B1)HT CACGACCCGCCGCTG |
| MU-SCF3 | 202 | CTGACCGTACCGTGG (B1: 00252550)HT GACATC (B1)HT (B1)HT CTGCTG (B1)HT (B1)HT AACTTC (B1)HT (B1)HT GAC (B1)HT (B1)HT GCTGTG (B1)HT CAGGTTATG (B1)HT CGCCTGCAGAAAGGT |
| MU-SCF4 | 203 | GCGCGTGAATGCACT (B1: 00252550)HT (B1)HT ACGCTG (B1)HT (B1)HT ATGCTG (B1)HT AAGCTG (B1)HT GTTGTGGTA (B1)HT GAGCGC (B1)HT (B1)HT GAA (B1)HT (B1)HT GCTGCCTAGGGGAGC |
| MU-SCF7-1 | 204 | ATCGTGCAAGTTGAA YWT (B1: 00252550)HT (B1)HT (B1)HT CCTGCTCGTCTGATC |
| MU-SCF7-2 | 205 | CCACCGGCAGAAGGT (B1: 00252550)HT GCGTGGCTGAAA YWT GAA (B1)HT (B1)HT GGC (B1)HT GAG YWT (B1)HT GCG (B1)HT CTG (B1)HT (B1)HT GTCAAACTGGTAGCT |
| MU-SCF8-1 | 206 | ACCCTGGTGGACGAC YWT (B1: 00252550)HT GGT (B1)HT GGTGCTGCCGATGAA |
| MU-SCF8-2 | 207 | ATCGACCTGTCCACT (B1: 00252550)HT (B1)HT GCG (B1)HT (B1)HT CTGCGC (B1)HT (B1)HT CTG (B1)HT (B1)HT TGGGTT (B1)HT GCGGGTCGTCGTGTG |
| MU-SCF15-1 | 208 | TCCCCTGTGCTGCTG (B1: 00252550)HT TCTACG (B1)HT ACC (B1)HT CAA (B1)HT CTGCGCATCAACCCAGAC |
| MU-SCF15-2 | 209 | GGCACCGTTGACGGTACT (B1: 00252550)HT (B1)HT (B1)HT AGCGATCCGCACATTCAGTTC (B1)HT ATC (B1)HT (B1)HT (B1)HT (B1)HT AATGGTTAGGGGAGC |
| MU-SCF23-1 | 210 | GTCTCTGAATGGCTG (B1: 00252550)HT (B1)HT ATC (B1)HT ATG (B1)HT (B1)HT TATACCGAGCACTTC |
| MU-SCF23-2 | 211 | AAACGCATTGGTGTT (B1: 00252550)HT (B1)HT (B1)HT (B1)HT (B1)HT CAA (B1)HT (B1)HT ATTGCT (B1)HTTCCCTGCTGGGCCTG |
| MU-SCF24-Lib1 | 212 | TCCCCAACCGAATTC (B1: 00252550)HT (B1)HT CTGCGT (B1)HT GTTCTGTTC (B1)HT TACATGATGGGT (B1)HT (B1)HT ACTAAA (B1)HT ATGGCG (B1)HT (B1)HT ATCACCACTGTGCTG |
| MU-SCF24-Lib2-1 | 213 | AAAGGCGGATCCCCA (B1: 00252550)HT (B1)HT TTC (B1)HT (B1)HT CTGCGT (B1)HT GTTCTGTTCGAATACATG |
| MU-SCF24-Lib2-2 | 214 | ATGGGTCGTGAGACTAAA (B1: 00252550)HT ATGGCG (B1)HT (B1)HT ATCACC (B1)HT (B1)HT CTGAAATTCCCGGAC |
| MU-SCF27-1 | 215 | CTGGGTCACTCTCGC (B1: 00252550)HT GATTGG (B1)HT (B1)HT AAACTG (B1)HT (B1)HT ATC (B1)HT (B1)HT AACCTGAGCCTGCAG |
| MU-SCF27-2 | 216 | AAATACGACCGTGTT (B1: 00252550)HT GAGATGATC (B1)HT GAAATG (B1)HT ATCGACGCG (B1)HT CACGAA (B1)HT AAGCTGTCCAACCTG |
| SCF28-Lib4 | 217 | GATAAAGGCGGATCC (B1: 00252550)HT (B1)HT GAA (B1)HT (B1)HT CTGAAA (B1)HT (B1)HT ATCTCC (B1)HT (B1)HT (B1)HT CTGGGC (B1)HT TTC (B1)HT GTTCCG (B1)HT CTGAAAGAAGCATGC |
| MU-SCF29-1 | 218 | AACGACGACCACGAG (B1: 00252550)HT AAACTGAGC NTT CTGATG (B1)HT (B1)HT TTCCCGGCGATTTCC |
| MU-SCF29-2 | 219 | CTGGAAAACAACAAC (B1: 00252550)HT (B1)HT (B1)HT (B1)HT CTGACCATC (B1)HT CTGCTG (B1)HT (B1)HT GAA (B1)HT GATGATAAGTCTGGG |
| SCF32-Lib4 | 220 | AAGGCTGGTATCACC (B1: 00252550)HT GAC (B1)HT (B1)HT TTCAAC (B1)HT ATCAAT (B1)HT GCG (B1)HT (B1)HT GTG (B1)HT (B1)HT GTTAAC (B1)HT (B1)HT AAGAAC (B1)HT ATCCTGAAAGCTCAC |

TABLE 2-continued

Oligos for library synthesis of Example 2
The codon used for mutation is (B1)HT where B1 is a mix of 25% C, 25% G, 50% T. This is denoted in various equivalent formats: (B1), (B1: 00252550), [00-25-25-50] in the ordered oligos due to different vendors

| Oligo # | SEQ ID NO: | Oligo sequences |
|---|---|---|
| MU-SCF37-1 | 221 | TCCTCTTCCGTAAAA[0-25-25-50]HTTGGGGTAACAGCCCT |
| MU-SCF37-2 | 222 | GCAGTTCGCATTCCA[0-25-25-50]HT[0-25-25-50]HTCTGATG[0-25-25-50]HT[0-25-25-50]HTCTG[0-25-25-50]HTCTG[0-25-25-50]HT[0-25-25-50]HTGATGATGAAGTGAAGATC[0-25-25-50]HT[0-25-25-50]HT[0-25-25-50]HT[0-25-25-50]HTGGCAAACTGATCATC |
| MU-SCF38-Lib1-1 | 223 | ATGTGCTACTCTCAT[0-25-25-50]HT[0-25-25-50]HT[0-25-25-50]HT[0-25-25-50]HT[0-25-25-50]HTGCGATCCTGACTAAC |
| MU-SCF38-Lib1-2 | 224 | TGCTATCGCAAGTCT[0-25-25-50]HTCGT[0-25-25-50]HT[0-25-25-50]HT[0-25-25-50]HT[0-25-25-50]HT[0-25-25-50]HTGTG[0-25-25-50]HTGGTCGTGGCTGCGGT |
| MU-SCF38-Lib1-3 | 225 | TGTCCTCCGGGCGAT[0-25-25-50]HT[0-25-25-50]HT[0-25-25-50]HTGAAGTTAAATGTTGC |
| MU-SCF40-1 | 226 | AACGTTCCGCTGGAC [0-25-25-50]HT [0-25-25-50]HT GTTCAC [0-25-25-50]HT [0-25-25-50]HT [0-25-25-50]HT [0-25-25-50]HT [0-25-25-50]HT [0-25-25-50]HT GAATCTGATGACGTTGCG |
| MU-SCF40-2 | 227 | CCTGGCAACGTTCTG [0-25-25-50]HT ATC [0-25-25-50]HT [0-25-25-50]HT AAGGGTTACACTCTGAATG |
| MU-SCF40-3 | 228 | GTCGTACCATTCGCGCT [0-25-25-50]HT [0-25-25-50]HT GTG [0-25-25-50]HT GTGGCAAAAGCTAAAG |
| MU-SCF42-1 | 229 | ATGGTTCGTGTTAAT[0-25-25-50]HT[0-25-25-50]HT[0-25-25-50]HTTWCGCTGAC[0-25-25-50]HTAACGGCGTGGTTGAA |
| MU-SCF42-2 | 230 | AAAGTCTCCGTATCT[0-25-25-50]HT[0-25-25-50]HTGGT[0-25-25-50]HTGCG[0-25-25-50]HTCCGGTTGAACTGGATTTTAGC[0-25-25-50]HTGTAGAAAAAGCAGGG |
| MU-SCF44-1 | 231 | CAAATCCTGTTCAAC [0-25-25-50]HT [0-25-25-50]HT GCGATGCAATGCGCG |
| MU-SCF44-2 | 232 | CGTCAGGCCGGTGCA [0-25-25-50]HT CTGGCTATCAAT [0-25-25-50]HT [0-25-25-50]HT [0-25-25-50]HT GTGCCG [0-25-25-50]HT [0-25-25-50]HT [0-25-25-50]HT TGGGCTCAGCACATTGTC |
| MU-SCF44-3 | 233 | CAGGACGGTGACCAGATC [0-25-25-50]HT CTG [0-25-25-50]HT CAG [0-25-25-50]HT [0-25-25-50]HT [0-25-25-50]HTGGCGGCGGGAGCTCT |
| MU-SCF47-1 | 234 | GATAAAGGCGGATCC[0-25-25-50]HT[0-25-25-50]HT[0-25-25-50]HTATGTGGGAGTATAAA |
| MU-SCF47-2 | 235 | GGCGTTTACTGCCGT[0-25-25-50]HTCTGGAC[0-25-25-50]HT[0-25-25-50]HT[0-25-25-50]HT[0-25-25-50]HT[0-25-25-50]HT[0-25-25-50]HTTTC[0-25-25-50]HTAACTCCAAG[0-25-25-50]HTATC[0-25-25-50]HTTTTC[0-25-25-50]HT[0-25-25-50]HT[0-25-25-50]HTACGGGGAGCTCTGGA |
| MU-SCF53-1 | 236 | GAGCCATGCGCTTGC[0-25-25-50]HT[0-25-25-50]HTGCA[0-25-25-50]HT[0-25-25-50]HT[0-25-25-50]HTGTTTGTGGCTCTGATGGC[0-25-25-50]HT[0-25-25-50]HTTAC[0-25-25-50]HTAAC[0-25-25-50]HTTGC[0-25-25-50]HTCTGAACTGT[0-25-25-50]HTAAGTTCAATGGCAAA |
| MU-SCF53-2 | 237 | GTAAAAGTGCACGAC[0-25-25-50]HTCCGTGC[0-25-25-50]HTCCG[0-25-25-50]HTGGGAGCTCTGGAGCC |
| SCF55-Lib4-1 | 238 | AAAGGCGGATCCACT (B1: 00252550)HT (B1)HT CTGGAA (B1)HT GCTTGC (B1)HT (B1)HT TGCGAGCGTGCGGGT |
| SCF55-Lib4-2 | 239 | GGTACCCCGTGTCCG (B1: 00252550)HT TGT (B1)HT GGCAAAGGTGTG (B1)HT CTG (B1)HT (B1)HT (B1)HT GGT (B1)HT (B1)HT CTGCTG (B1)HT TTCATCCAGAAGCAC |
| MU-SCF56-Lib1 | 240 | TGCTCTCAGAATGAANTTTTCGAC[0-25-25-50]HT[0-25-25-50]HT[0-25-25-50]HT[0-25-25-50]HTGCGTGTNTTCCGTGCCAA[0-25-25-50]HT[0-25-25-50]HTTGC[0-25-25-50]HT[0-25-25-50]HT[0-25-25-50]HT[0-25-25-50]HTCCTCCA[0-25-25-50]HTACGTGTCAGCGTTAC |
| MU-SCF56-Lib2 | 241 | AATGAATATTTCGAC[0-25-25-50]HT[0-25-25-50]HT[0-25-25-50]HT[0-25-25-50]HTGCGTGTATCCCGTGCCAA[0-25-25-50]HTCGCTGC[0-25-25-50]HTAAC[0-25-25-50]HTCCTCCA[0-25-25-50]HTACGTGTCAGCGTTAC |
| MU-SCF63-1 | 242 | TATGACTACGAAGCC[0-25-25-50]HT[0-25-25-50]HT[0-25-25-50]HTGACCTGAGCTTCCACAAAGGC |
| MU-SCF63-2 | 243 | GAAAAGTTCCAGATCCTG[0-25-25-50]HT[0-25-25-50]HT[0-25-25-50]HT[0-25-25-50]HT[0-25-25-50]HT[0-25-25-50]HTTGG[0-25-25-50]HTGCTCGTTCTCTGACC |
| MU-SCF63-3 | 244 | ACGGGTGAAACCGGT[0-25-25-50]HTATCCCAAGCAATTAC |

TABLE 2-continued

Oligos for library synthesis of Example 2
The codon used for mutation is (B1)HT where B1 is a mix of 25% C, 25% G, 50% T. This is denoted in various equivalent formats: (B1), (B1: 00252550), [00-25-25-50] in the ordered oligos due to different vendors

| Oligo # | SEQ ID NO: | Oligo sequences |
|---|---|---|
| MU-SCF64-1 | 245 | GGATCCGGTCCACTG [0-25-25-50]HT TCTCAT [0-25-25-50]HT [0-25-25-50]HT GCTCTGGGT [0-25-25-50]HTCGTCTG [0-25-25-50]HT CCGCGCGTGCAGGCA |
| MU-SCF64-2 | 246 | CAGCCTGCATTCGCG [0-25-25-50]HT [0-25-25-50]HT ATTACC [0-25-25-50]HT [0-25-25-50]HT CTGCTG [0-25-25-50]HT [0-25-25-50]HT TCTCCGGCTCAGCTG |
| MU-SCF64-3 | 247 | GACTCCCTGCGTGCC [0-25-25-50]HT GTAGAA [0-25-25-50]HT GCGATGGAA [0-25-25-50]HT ATCGTTGCGCACGGG |
| MU-SCF65-1 | 248 | AAAGGCGGATCCATG [0-25-25-50]HT CAA [0-25-25-50]HT [0-25-25-50]HT CTGCTG [0-25-25-50]HT WTKCCGGGTGTGAATGCT |
| MU-SCF65-2 | 249 | ATGCACCACGTCAAG [0-25-25-50]HT [0-25-25-50]HT [0-25-25-50]HT GAACTG [0-25-25-50]HT [0-25-25-50]HTCTGTCTCAGGATGAG |
| MU-SCF65-3 | 250 | AAACAGCTGTACGAC [0-25-25-50]HT NTT [0-25-25-50]HT [0-25-25-50]HT [0-25-25-50]HT [0-25-25-50]HT [0-25-25-50]HT GAAGTAGTTGGGAGC |
| MU-SCF66 | 251 | CTGCGCAATCAGCCA [0-25-25-50]HT TTT [0-25-25-50]HT [0-25-25-50]HT WTK CGT [0-25-25-50]HT [0-25-25-50]HTATCCAG [0-25-25-50]HT [0-25-25-50]HT CCGTCC [0-25-25-50]HT CTGCCG [0-25-25-50]HT CTGCTCCAG [0-25-25-50]HT ATCGGTCGTGAAAAC |
| MU-SCF70 | 252 | CGTCGTTACAATATC [0-25-25-50]HT [0-25-25-50]HT [0-25-25-50]HT [0-25-25-50]HT GTG [0-25-25-50]HT GGT [0-25-25-50]HT [0-25-25-50]HT CGTCGC [0-25-25-50]HT [0-25-25-50]HT GAA [0-25-25-50]HT [0-25-25-50]HTATTTTCGAATACGAG |
| MU-SCF75-1 | 253 | <u>CTGAATGTGGTTCTG</u>[0-25-25-50]HT[0-25-25-50]HTATC[0-25-25-50]HT[0-25-25-50]HTGGCGCT[0-25-25-50]HTCCGGGTGCC[0-25-25-50]HTATTGAGGAAGGTGGCAAC[0-25-25-50]HTCAG[0-25-25-50]HTTAC[0-25-25-50]HT<u>CAGGGTGAGCGTCTG</u> |
| MU-SCF75-2 | 254 | <u>ATCGAAGAAATCAAC</u>[0-25-25-50]HT[0-25-25-50]HT<u>CACGTGATGCTGCGT</u> |
| MU-SCF75-3 | 255 | <u>ATTGAACGTCTGTCT</u>[0-25-25-50]HT[0-25-25-50]HT<u>GGGAGCTCTGGAGCC</u> |
| SCF95-Lib4 | 256 | TTCAATAAAGAACAA (B1: 00252550)HT (B1)HT GCA (B1)HT (B1)HT GAAATC (B1)HT (B1)HT CTGCCGAACCTG (B1)HT (B1)HT (B1)HT CAG (B1)HT (B1)HT GCATTT (B1)HT (B1)HT AGTCTGAAAGATGAC |

TABLE 3

Oligos for library synthesis of Example 1
Polynucleotide sequences that encompass the variable domain of one embodiment of libraries 1-69, where X marks the locations of mutation where codons of interest may be included. There are multiple sequences shown for some libraries that reflect a discontinuous variable domain.

| Oligo # | SEQ ID NO: | Sequence |
|---|---|---|
| SCF2-1 | 75 | <u>CTGCCGGATGGCTGG</u> X ATG X TTCCATAACTCCGGCGTGCCGGTTTAT X CAC X X TCC X <u>GTAGTCACCTGGAGC</u> |
| SCF2-2 | 76 | <u>CGTCCGTACTTTCTGGGT</u> X GGT X X X X <u>CACGACCCGCCGCTG</u> |
| SCF3-1 | 77 | <u>CTGACCGTACCGTGG</u> X GACATC X X CTGCTG X X AACTTC X X GAC X X GCTGTG X CAGGTTATG X <u>CGCCTGCAGAAAGGT</u> |
| SCF4-1 | 78 | <u>GCGCGTGAATGCACT</u> X X ACGCTG X X ATGCTG X AAGCTG X GTTGTGGTA X GAGCGC X X GAA X X <u>GCTGCCTAGGGGAGC</u> |
| SCF7-1 | 79 | <u>ATCGTGCAAGTTGAA</u> X X X X <u>CCTGCTCGTCTGATC</u> |
| SCF7-2 | 80 | <u>CCACCGGCAGAAGGT</u> X GCGTGGCTGAAA X X X X GGC X GAG X X GCG X CTG X X <u>GTCAAACTGGTAGCT</u> |
| SCF8-1 | 81 | <u>ACCCTGGTGGACGAC</u> X X GGT X GGT X GCC X <u>GAAACCGTAGAGTTC</u> |
| SCF8-2 | 82 | <u>TACGAAATCGACCTG</u> X X X X GCG X X CTGCGC X X CTG X X TGGGTT X <u>GCGGGTCGTCGTGTG</u> |

TABLE 3-continued

Oligos for library synthesis of Example 1
Polynucleotide sequences that encompass the variable domain of one embodiment of libraries 1-69, where X marks the locations of mutation where codons of interest may be included. There are multiple sequences shown for some libraries that reflect a discontinuous variable domain.

| Oligo # | SEQ ID NO: | Sequence |
|---|---|---|
| SCF9-1 | 83 | AAAGGCGGATCCTCT X CGTGAATGC X CTGTAC X CAGAAACACAACATC X X CTG X X GACTCC X X CAACTGTGTACCGCT |
| SCF10-1 | 84 | GCAGATCCGCGCCTG X X TCTCTGTCT X ATGCTG X X GGT X TCCGATGAAGGTGGT |
| SCF10-2 | 85 | CAGACCAAAAACTAT X ATC X GCTGCG X X ACTATCCAG X AGCAAG X GGGAGCTCTGGAGCC |
| SCF12-1 | 86 | GTTCGTCGTATTGAT X X GGCCGCGTTGTGATCCCT X GAAATC X X ACCCTG X ATT X X GGTGACCCACTGGAA |
| SCF14-1 | 87 | ATGCTGCAGAAAGCG X X GTT X X GGCACGTTCATCTACCTG X X X ACTGAGTTTTTCATC X GTG X X GGTTGGAAAAAGCTGCAA |
| SCF14-2 | 88 | CTGGGTGAACTGATTCCG X CCA X TAGGGGAGCTCTGGA |
| SCF15-1 | 89 | TCCCCTGTGCTGCTG X TCTACG X ACC X CAA X CTGCGCATCAACCCAGAC |
| SCF15-2 | 90 | GGCACCGTTGACGGTACT X X X AGCGATCCGCACATTCAGTTC X ATC X X X X AATGGTTAGGGGAGC |
| SCF22-1 | 91 | AAAGTGCTGGAAATG X ATT X X CTG X CTG X X X TCT X X TGCCTG X X GCA X ATC X ACGGTACAGGAGCTG |
| SCF23-1 | 92 | GTCTCTGAATGGCTG X X ATC X ATG X X TATACCGAGCACTTC |
| SCF23-2 | 93 | AAACGCATTGGTGTT X X X X CAA X X ATTGCT X TCCCTGCTGGGCCTG |
| SCF24-1 | 94 | TCCCCAACCGAATTC X X CTGCGT X X CTGTTC X TACATGATGGGT X X ACTAAA X X GCG X X ATCACC X X CTGAAATTCCCGGAC |
| SCF27-1 | 95 | CTGGGTCACTCTCGC X GATTGG X X AAACTG X X ATC X X AACCTGAGCCTGCAG |
| SCF27-2 | 96 | AAATACGACCGTGTT X GAGATGATC X GAAATG X ATCGACGCG X CACGAA X AAGCTGTCCAACCTG |
| SCF28-1 | 97 | GATAAAGGCGGATCC X X GAA X X CTGAAA X X ATCTCC X X X CTGGGC X TTC X GTTCCG X CTGAAA X GCATGCCGTGCGTAT |
| SCF29-1 | 98 | GAGTCTAAACTGAGC X CTGATG X X TTCCCGGCGATTTCC |
| SCF29-2 | 99 | CTGGAAAACAACAAC X X X X ACCATC X CTGCTG X X GAA X GATGATAAGTCTGGG |
| SCF31-1 | 100 | TCTGAAGCAGCTGAA X GCGGTT X X CTGGCG X CTG X X AAAGAGGCGCAGGCT |
| SCF31-2 | 101 | AACCCGAAAGCACGT X X GACCTG X X GAGGCG X X CGTCTGCGCGGGAGC |
| SCF32-1 | 102 | AAGGCTGGTATCACC X GAC X X TTCAAC X ATCAAT X GCG X X GTG X X GTTAAC X X AAGAAC X ATCCTGAAAGCTCAC |
| SCF33-1 | 103 | GGTAAATGCGTGTGC X X X X TGC X X X TGT X X X X AAA X GACGAAAAT X TGC X TATCCGTGTTCTTGC |
| SCF35-1 | 104 | GACCCAAATACCCAG X X TGT X TGCCCGGAAGGCTAC X X X X GGC X ATCTGC X GAC X X GAGTGC X X GGCGGTTTTTGTTCT |
| SCF36-1 | 105 | GGCAGCTGTAAGGAC X X CAGTCTTAC X TGC X TGCCTG X GCGTTT X X X AACTGC X ACCCAC X GACGAT X GGGAGCTCTGGAGCC |
| SCF37-1 | 106 | GCAGTTCGCATTCCA X X X ATG X X CTG X CTGAACATTGATGATGAAGTGAAG X X X X X AAACTGATCATCGAG |
| SCF38-1 | 107 | ATGTGCTACTCTCAT X X X TCC X GCGATCCTGACTAAC |
| SCF38-2 | 108 | TGCTATCGCAAGTCT X CGT X X X X X X X GGTCGTGGCTGCGGTTGTCCTCCGGGC X X X X GAAGTTAAATGTTGC |
| SCF39-1 | 109 | GAGGCGATGGAACTG X X AAGCCGAAACCGTAT |
| SCF39-2 | 110 | TACGAGATCGGTGAA X GTG X TAC X TGCAAA X X TAT X X X X X CTG X X X ACCATCTGCGACCGT |
| SCF40-1 | 111 | GAGACGAACGTTCCG X X X X GTTCAC X X X X X X GAATCTGATGACGTT |

TABLE 3-continued

Oligos for library synthesis of Example 1
Polynucleotide sequences that encompass the variable domain of one embodiment of libraries 1-69, where X marks the locations of mutation where codons of interest may be included. There are multiple sequences shown for some libraries that reflect a discontinuous variable domain.

| Oligo # | SEQ ID NO: | Sequence |
|---|---|---|
| SCF40-2 | 112 | AACGTTCTGGGCATC X X AAGGGTTACACTCTGAAT |
| SCF40-3 | 113 | GGTCGTACCATTCGCGCT X X GTG X X GCAAAAGCTAAAGCA |
| SCF41-1 | 114 | GAATGCTTTGCCCTG X X X X X TTC X CGTGCGGAAGTGGAA |
| SCF41-2 | 115 | GTAGTCAAATTCATT X X GGC X TAC X GAGGTTCTGCTGTCC |
| SCF42-1 | 116 | ATGGTTCGTGTTAAT X X X X GCTGAC X AACGGCGTGGTTGAA |
| SCF42-2 | 117 | AAAGTCTCCGTATCT X X GGT X GCG X X X X CTGGATTTTAGC X GTAGAAAAAGCAGGG |
| SCF43-1 | 118 | GGCGGATCCCCAGTA X TGCTGT X X TTT X X X AAG X X GTCCAG X CTGGCTTCTTATCGC |
| SCF43-2 | 119 | AGCTCCAAATGTCCG X GAAGCGGTT X TTCAAA X ATC X GCC X X X TGCGCAGACCCTAAA |
| SCF44-1 | 120 | GATCAGCGTCAGGCC X GCA X CTG X ATCAAT X X X GTGCCG X X X TGGGCTCAGCACATTGTC |
| SCF44-2 | 121 | CAGGACGGTGACCAGATC X CTG X CAG X X X GGCGGCGGGAGCTCT |
| SCF45-1 | 122 | GGCGGATCCATGAAA X X TGGCCGGAACTG X GGCAAATCTGTTGAA |
| SCF45-2 | 123 | ATCGTGCTGCCTGTG X X X X X X X X ATCGATCGTGTCCGC |
| SCF45-3 | 124 | CTGGATAACATTGCT X X CCA X GTAGGTGGGAGCTCT |
| SCF46-1 | 125 | CCGGATGAATCCTTT X TGC X CAGCCGGACCAA X TGTGCATTCATCTGC |
| SCF46-2 | 126 | CTGCCGTCTGAGGGT X TGT X CCACACCCGACC X X X GCG X X GGCGCCGTGGAATGG |
| SCF46-3 | 127 | TGCCGTACGACTTGC X CCG X X GGGAGCTCTGGAGCC |
| SCF47-1 | 128 | GATAAAGGCGGATCC X X ATGTGGGAGTATAAA |
| SCF47-2 | 129 | GGCGTTTACTGCCGT X CTGGAC XXX X X TTC X AACTCCAAG X X X TTC X X X ACGGGGAGCTCTGGA |
| SCF48-1 | 130 | AAAGATATTGCGAAG X GTTCCG X X X X ATG X X X X TGG X X CTGGGTGTA X CAGTCT X X TGGGTCCACTATATG |
| SCF49-1 | 131 | GAGGGCTATCTGGTG X AAAAAC X GGCTGC X X X TGT X X X GGTGAT X GAC X TGCCTG X X TGCAAGCAGCAGTAC |
| SCF49-2 | 132 | GCGGGTGGTTACTGT X X X X TGCTGGTGCACCCAC |
| SCF50-1 | 133 | GATAAAGGCGGATCC X X X ATG X TTCTGCCGCGTTTGTAAG X X X X CTGCTG X TGT X ACCTGCCCGTCTTCC |
| SCF50-2 | 134 | AATCCACCGCTGCCG X X CCT X X X TGGCTGTGTCCGCGT |
| SCF51-1 | 135 | TGTACCAATTGCTTC X X X ACT X CTGTGGCGCCGTAACCCT |
| SCF51-2 | 136 | GAAGGTCAACCACTGTGC X X TGTGGC X X CTGAAA X X GGT X GTT X X X X X GGGAGCTCTGGAGCC |
| SCF52-1 | 137 | GATAAAGGCGGATCC X AAA X TGT X TGC X X X X X CCTGTTTGTGGTTCC |
| SCF52-2 | 138 | GACGGTCGTACTTAC X X TCCTGC X GCACGCTGC X GGTGTGAGCATCAAA |
| SCF53-1 | 139 | GAGCCATGCGCTTGC X X X X X GTTTGTGGCTCTGATGGC X X X X X TGC X CTGAACTGT X AAGTTCAATGGCAAA |
| SCF53-2 | 140 | GTAAAAGTGCACGAC X CCGTGC X CCG X GGGAGCTCTGGAGCC |
| SCF54-1 | 141 | GTCTCTCACATCCCG X X X X X TCCTTT X CCG X TGCGACGAAAACGGCAAC |
| SCF54-2 | 142 | TACCTGCCGCTGCAATGC X X X X X TGTTGGTGCGTATTC |
| SCF54-3 | 143 | GAGGTTCCAAACACT X TCC X X X X AATTGTTCTGAAAGC |
| SCF55-1 | 144 | AAAGGCGGATCCACT X X CTGGAA X GCTTGC X X TGCGAGCGTGCGGGT |

TABLE 3-continued

Oligos for library synthesis of Example 1
Polynucleotide sequences that encompass the variable domain of one embodiment of libraries 1-69, where X marks the locations of mutation where codons of interest may be included. There are multiple sequences shown for some libraries that reflect a discontinuous variable domain.

| Oligo # | SEQ ID NO: | Sequence |
|---|---|---|
| SCF55-2 | 145 | GGTACCCCGTGTCCG X TGT X GGCAAAGGTGTG X CTG X X X GGT X X CTGCTG X TTCATCCAGAAGCAC |
| SCF56-1 | 146 | TGCTCTCAGAATGAA X TTCGAC X X X X GCGTGT X CCGTGCCAA X X TGC X X X X CCTCCA X ACGTGTCAGCGTTAC |
| SCF57-1 | 147 | GATAAAGGCGGATCC X X GGTGCA X TGG X TGTACCGCTTGT X X X AAT X CCA X X ATCCGTTGC X X TGCGAGATGCCGCGC |
| SCF58-1 | 148 | GGCGGATCCTGTATC X X X X X TGTGGTCCTAAG X X GGCGTTCCATGCTGC |
| SCF58-2 | 149 | GAACCGTATACCTGC X X GAC X X X X TGC X GGGAGCTCTGGAGCC |
| SCF60-1 | 150 | GTTAAAGTAAAATTC X X X GGCGAAGAGAAGGAGGTG |
| SCF60-2 | 151 | GACACGTCCAAAATC X X GTC X CGC X GGTAAA X GTG X TTT X TATGACGACAACGGCAAA X GGT X GGT X GTT X GAAAAGATGCCCCG |
| SCF62-1 | 152 | TGTAGCGAACAGGCA X X X X TGC X X X X X CGTTGGTATTTCGAT |
| SCF62-2 | 153 | AAATGCGCTCCGTTC X TACGGT X TGT X GGCAACCGCAACAAT |
| SCF63-1 | 154 | TATGACTACGAAGCC X X X X X CTGAGCTTCCACAAAGGC |
| SCF63-2 | 155 | GAAAAGTTCCAGATCCTG X X X X X X TGG X GCTCGTTCTCTGACC |
| SCF63-3 | 156 | ACGGGTGAAACCGGT X ATCCCAAGCAATTAC |
| SCF64-1 | 157 | GGATCCGGTCCACTG X TCTCAT X X GCTCTGGGT X CGTCTG X CCGCGCGTGCAGGCA |
| SCF64-2 | 158 | CAGCCTGCATTCGCG X X ATTACC X X CTGCTG X X TCTCCGGCTCAGCTG |
| SCF64-3 | 159 | GACTCCCTGCGTGCC X GTAGAA X GCGATGGAA X ATCGTTGCGCACGGG |
| SCF65-1 | 160 | AAAGGCGGATCCATG X CAA X X CTGCTG X X CCGGGTGTGAATGCT |
| SCF65-2 | 161 | ATGCACCACGTCAAG X X X GAACTG X X CTGTCTCAGGATGAG |
| SCF65-3 | 162 | AAACAGCTGTACGAC X X X X X X GAAGTAGTTGGGAGC |
| SCF66-1 | 163 | GAATTCCTGCGCAAT X CCA X TTT X X X CGT X X ATCCAG X X CCGTCC X CTGCCG X X CTCCAG X ATCGGTCGTGAAAAC |
| SCF69-1 | 164 | CCGGAAGAGCGCTAC X X X CTG X X CTGAAC X X GGCTTCTTCGACTTT |
| SCF69-2 | 165 | CGTCGTTCCGGTGGC X X X X GCTCTG X AGCCTG X AATGGTGACGTTGGG |
| SCF70-1 | 166 | TCTGACACCGAACTG X ACTCTGCTGCGTCGTTACAAT X X X X X X GGT X X CGTCGC X X GAA X X ATTTTCGAATACGAG |
| SCF71-1 | 167 | ACTACGCCGAAGTCT X GCTGTTGAA X CTGAGC X X GGCTTCACCGAAGAA |
| SCF71-2 | 168 | GAGAAATGCAACTGG X X X GCGGCC X X TTTCTG X X TCCGCAGGGAGCTCT |
| SCF72-1 | 169 | GATAAAGGCGGATCC X CAA X CCACCGGGC X GAACTG X X GGTTACACT X GAAGTA X X CAGCAGCCTCCGGAC |
| SCF75-1 | 170 | CTGAATGTGGTTCTG X X ATC X X GGC X X CCG X GCC X ATT X GAAGGTGGC X X X X TAC X CAGGGTGAGCGTCTG |
| SCF75-2 | 171 | ATCGAAGAAATCAAC X X CACGTGATGCTGCGT |
| SCF75-3 | 172 | ATTGAACGTCTGTCT X X GGGAGCTCTGGAGCC |
| SCF76-1 | 173 | AGCAAACCGGCTTTC X GGT X CTG X AACGTGTGGAAGGAA |
| SCF76-2 | 174 | TGCATCTACGAGCTG X X X GGT X GGC X X X X X X TGG X GGC X TGGACCCCAGTTCGC |
| SCF77-1 | 175 | CAATGCAAAGTCCTG X GAATACATCCCA X X X X GAACTGGAGCTGAAA |
| SCF77-2 | 176 | GATATTAACGAGGAA X X X X TGGTGGTCTGGTACTCTG |

TABLE 3-continued

Oligos for library synthesis of Example 1
Polynucleotide sequences that encompass the variable domain of one embodiment of libraries 1-69, where X marks the locations of mutation where codons of interest may be included. There are multiple sequences shown for some libraries that reflect a discontinuous variable domain.

| Oligo # | SEQ ID NO: | Sequence |
|---|---|---|
| SCF77-3 | 177 | AACAATAAACTGGGC X TTTCCGAGC X X GTTAAAGAACTGGAA |
| SCF78-1 | 178 | GCCGCAGGTACTTGC X GAA X X X GGC X X TGT X TGCAACCAGGGTTAT X X TCC X GACGGC X X AAT X ACCTGTATTGTTCGT |
| SCF79-1 | 179 | AAACCGGGTGATAGC X AACACCCCTTGGGGTAAGGTCATC X AACGCAGCG X CAG X ACCATGAACGGCACC |
| SCF79-2 | 180 | GCTGACAATAGCTCT X GTTCCG X GGC X GGT X X X GTGCTGAACTCCCTG |
| SCF80-1 | 181 | TCCATGCGTAAGTGG X TGT X X TGC X TTTATCTACGATGAG |
| SCF80-2 | 182 | ATTCCTGCGGACTGG X TGTCCGGACTGC X X X AAA X X TTC X ATGATCGAGATCGCC |
| SCF81-1 | 183 | GGCGCGATGGGTACC X GAGTGC X X X X GGCGGCTGCTCT X X TGC X X X X ATCGGTTACGAATGT X TGTCCGGACGGTTTT |
| SCF82-1 | 184 | GTTACTTGTGAACCG X ACC X TTC X X AAGTGCAAC X TGT X TGC X X X GGTAAA X GCG X TGC X X X X TGCAATCAGGGGAGC |
| SCF83-1 | 185 | ATCGTTGTGGCGCTG X X TAC X TCT X X X X GATCTGTCTTTCCAG |
| SCF83-2 | 186 | CTGGAGGAATCCGGT X X TGGAAAGCACGCTCCCTG |
| SCF83-3 | 187 | GCCACCCGTAAGGAAGGT X ATTCCAAGC X X GTAGCTCGTGTGGAC |
| SCF89-1 | 188 | AAAGGCGGATCCATG X GTAATCTTCCTGAAAGACGTT X GGCAAAGGTAAA X GGT X X X X GTGGCCGATGGTTAC |
| SCF89-2 | 189 | GCAACCCCGGCAAAC X X GCGCTG X GCTCAG X X AAAGAA X CGTGGGAGCTCTGGA |
| SCF90-1 | 190 | CCGGTTTCTAAATGT X X X CAATGT X X GATTGC X CTGGATAAACACGCT X TCCGGT X TGTTTCTATGACGAA |
| SCF90-2 | 191 | ATCTGCGACTACTGC X X GGGAGCTCTGGAGCC |
| SCF91-1 | 192 | GGCCAATCCTGCGGT X X ACC X X TGTGCTCAGGGTCTG X TGT X CCACGTCAGGACGAA X X CCG X X GCC X X X GGTCGTGGCGTGTGC |
| SCF92-1 | 193 | GATAAAGGCGGATCC X X TGTTCC X X CCG X X X TGT X X X X X X CTGTGCGGCTCTGAC |
| SCF92-2 | 194 | AAAACCTACGGCAAC X TGC X TTCTGCAACGCGGTG |
| SCF92-3 | 195 | CTGACCCTGAGCCAC X GGTAAATGCGGGAGC |
| SCF93-1 | 196 | AAAAGCTGCTGCCCT X X X GGTCGC X X TACAAC X TGTCGT X X GGT X TCTCGTGAA X TGTGCT X X AGCGGCTGCAAGATT |
| SCF94-1 | 197 | GATAAAGGCGGATCC X X X X GTAGAAAAGGTCCTG |
| SCF94-2 | 198 | TATCTGCTGAAATGG X X X TCCGAAGAACACAACACCTGG X CCAGAG X X CTG X TGC X X X ATCTCT X TTCATGAAAGGGAGC |
| SCF73-1 | 199 | TCTGATGAGGACTTC X X GTTTTC X X X CGT X X TTTGCG X X X CTG X X CAGCAA X CTGAAAAAG X AAAGGTCTGTTCGGG |

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A library of distinct peptidic compounds, wherein the compounds of the library comprise one of following:
   a) a peptidic scaffold domain that is Chain C:LEM domain/emerin (SCF70) having a variable domain comprising 5 or more mutations at positions selected from 22, 23, 24, 25, 27, 29, 30, 33, 34, 36 and 37;
   b) a peptidic scaffold domain that is Transcription antitermination protein NusG (SCF42) having a variable domain comprising 5 or more mutations at positions selected from 16, 17, 18, 19, 22, 42, 43, 45, 47 and 55;
   c) a peptidic scaffold domain that is GYF domain of CD2bp2 (SCF47) having a variable domain comprising 5 or more mutations at positions selected from 42, 45, 46, 47, 48, 49, 51, 55, 57, 59, 60 and 61;
   d) a peptidic scaffold domain that is C-terminal domain of Ku (SCF28) having a variable domain comprising 5 or more mutations at positions selected from 1, 2, 4, 5, 8, 9, 12, 13, 14, 17, 19 and 22;
   e) a peptidic scaffold domain that is Fyn SH3 domain (Fynomers) (SCF63) having a variable domain comprising 5 or more mutations at positions selected from 13, 14, 15, 16, 30, 31, 32, 33, 34, 35, 36, 38 and 49; and
   f) a peptidic scaffold domain that is Chain C: GspC (SCF75) having a variable domain comprising 5 or more mutations at positions selected from 12, 13, 15, 16, 19, 23, 30, 32, 34, 51, 52, 67 and 68.

2. The library of claim 1, wherein the mutations are selected from amino acid residues encoded by a B1(HT) random codon.

3. The library of claim 1, wherein the mutations are selected from amino acid residues encoded by a NNK random codon.

4. The library of claim 1, wherein the peptidic scaffold domain has an underlying sequence selected from one of SEQ ID NO: 15, 27, 32, 46, 51 and 55.

5. The library of claim 1, wherein the five or more different mutations are 6 or more mutations.

6. The library of claim 1, wherein the five or more different mutations are 7 or more mutations.

7. The library of claim 1, wherein the five or more different mutations are 8 or more mutations.

8. The library of claim 1, wherein the five or more different mutations are 9 or more mutations.

9. The library of claim 1, wherein the five or more different mutations are 10 or more mutations.

10. The library of claim 1, wherein the library comprises 50 or more distinct compounds.

11. The library of claim 1, wherein the library is a phage display library and each compound of the library is fused to at least a portion of a viral coat protein.

12. The library of claim 1, wherein the viral coat protein is selected from the group consisting of protein pIII, major coat protein pVIII, Soc, Hoc, gpD, pv1 and variants thereof.

13. A library of polynucleotides that encodes a library according to claim 1.

14. The library of claim 13, wherein the library is a library of replicable expression vectors.

15. The library of claim 13, wherein each polynucleotide encodes a peptidic compound comprising:
   a scaffold domain having an underlying sequence selected from one of SEQ ID NO: 15, 27, 32, 46, 51 and 55.

16. A method of screening, comprising:
   contacting a target protein with a library according to claim 1; and
   identifying a compound of the library that specifically binds to the target protein.

17. The method of claim 16, wherein the target protein is selected from the group consisting of a hormone, a growth factor, a receptor, an enzyme, a cytokine, an osteoinductive factor, a colony stimulating factor or an immunoglobulin.

18. The method of claim 16, wherein the target protein is selected from the group consisting of a VEGF protein, a RANKL protein, a NGF protein, a TNF-alpha protein, a SH2 domain containing protein, a SH3 domain containing protein, a BLyS protein, a PCSK9 protein, a DLL4 protein, an Ang2 protein, a CTLA-4 protein and a *Clostridium difficile* Toxin A or B protein, a PDGF-B protein, a Robo4 protein, a Htra1 protein, a hemagglutinin protein, a Nav1.7 protein, a CD5 protein, a CD19 protein, a CD38 protein, a CD40 protein, a IGF-1R protein, a GM-CSF protein, a PCSK9 protein, a BlyS protein, a Ang2 protein, an EGFR protein, a HER2 protein, a Robo4 protein, a Htra1 protein, a CXCL5 protein, a Sclerostin protein, a R-Spondin protein, a MD-2 protein, an Influenza HA hemagglutinin protein or a coiled coil mimic thereof, an HCV protein and an HIV protein.

19. The method of claim 16, wherein the target protein is a D-protein.

20. The method of claim 5, wherein the target protein is a L-protein.

* * * * *